US012152074B2

(12) United States Patent
Nicosia et al.

(10) Patent No.: US 12,152,074 B2
(45) Date of Patent: Nov. 26, 2024

(54) ANTAGONISTIC PD-1, PD-L1 AND LAG-3 BINDING PROTEINS

(71) Applicant: KEIRES AG, Basel (CH)

(72) Inventors: Alfredo Nicosia, Naples (IT); Nicola Zambrano, Casavatore (IT); Emanuele Sasso, Pollena Trocchia (IT); Claudia De Lorenzo, Naples (IT)

(73) Assignee: CeingeBiotecnologie Avanzate Franco Salvatore Scarl, Naples (IT)

( * ) Notice: Subject to any disclaimer, the term of this patent is extended or adjusted under 35 U.S.C. 154(b) by 380 days.

(21) Appl. No.: 16/980,666

(22) PCT Filed: Mar. 22, 2019

(86) PCT No.: PCT/EP2019/057239
§ 371 (c)(1),
(2) Date: Sep. 14, 2020

(87) PCT Pub. No.: WO2019/180201
PCT Pub. Date: Sep. 26, 2019

(65) Prior Publication Data
US 2020/0407447 A1    Dec. 31, 2020

(30) Foreign Application Priority Data

Mar. 22, 2018 (EP) .................................. 18163432

(51) Int. Cl.
*C07K 16/28* (2006.01)
*A61P 35/00* (2006.01)
*A61K 39/00* (2006.01)

(52) U.S. Cl.
CPC .......... *C07K 16/2818* (2013.01); *A61P 35/00* (2018.01); *C07K 16/2803* (2013.01);
(Continued)

(58) Field of Classification Search
CPC ............ C07K 16/2818; C07K 16/2803; C07K 16/2827; C07K 2317/21; C07K 2317/622;
(Continued)

(56) References Cited

U.S. PATENT DOCUMENTS 7,084,257 B2 * 8/2006 Deshpande .......... C07K 16/249
424/85.5
2016/0222120 A1   8/2016 Narwal et al.
2016/0272708 A1   9/2016 Chen

FOREIGN PATENT DOCUMENTS

WO    WO 2010/019570      2/2010
WO    WO 2013/181634     12/2013
(Continued)

OTHER PUBLICATIONS

Sznol and Chen Antagonist Antibodies to PD-1 and B7-H1 (PD-L1) in the Treatment of Advanced Human Cancer. Clin Cancer Res (2013) 19 (5): 1021-1034 (Year: 2013).*
(Continued)

*Primary Examiner* — Joanne Hama
*Assistant Examiner* — Pratik Thapa
(74) *Attorney, Agent, or Firm* — Knobbe, Martens, Olson & Bear, LLP

(57) ABSTRACT

The present invention relates to antagonistic antigen binding proteins, a nucleic acid encoding the antagonistic binding protein, a recombinant expression vector comprising the nucleic acid molecule, a host cell comprising the vector, a method of making the antagonistic antigen binding protein, an antagonistic binding protein produced by the method and a pharmaceutical composition comprising the antagonistic binding protein, the nucleic acid or the vector. The present invention further relates to a kit comprising the pharmaceu-
(Continued)

Figure 1:
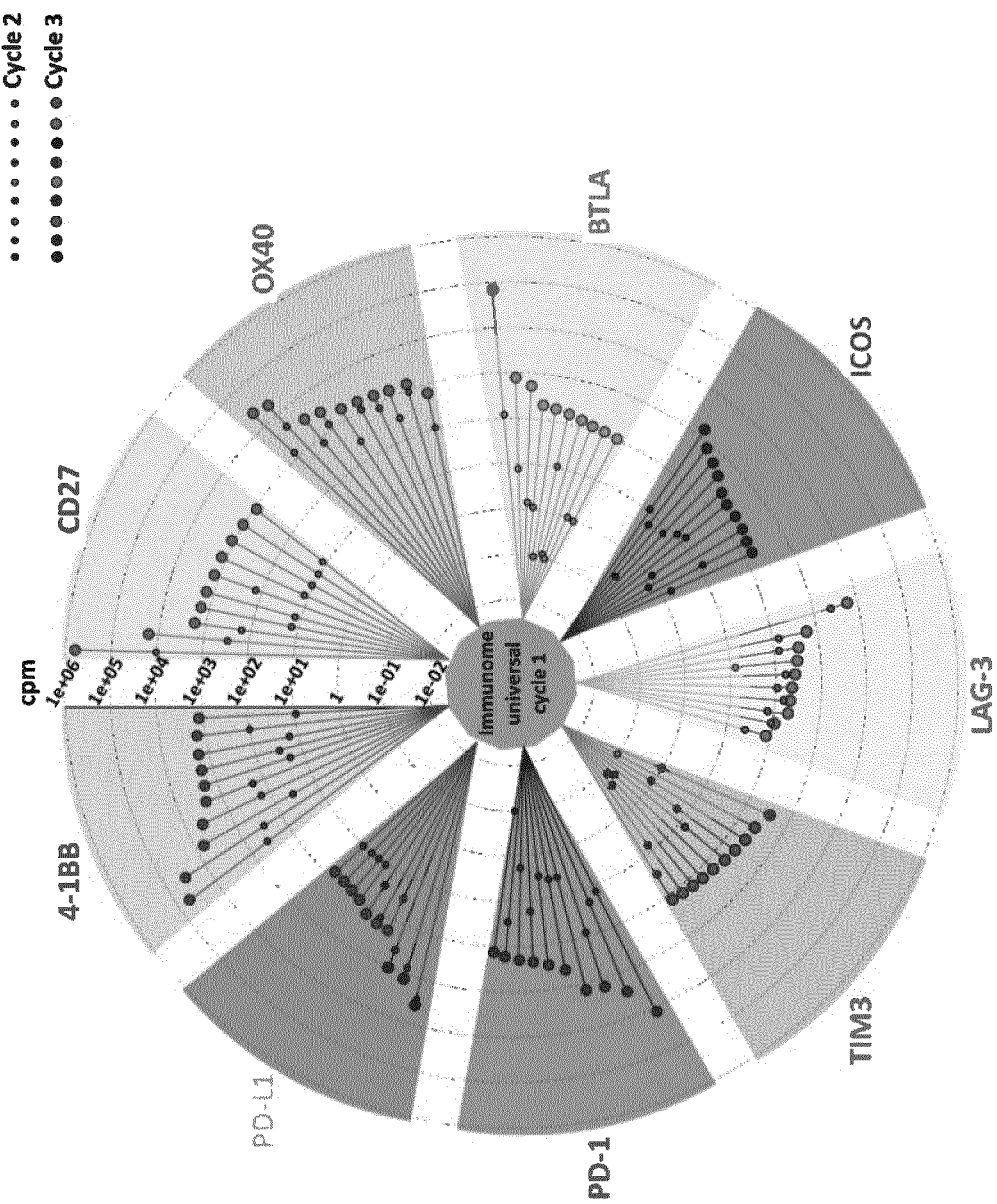

tical composition and use of the antagonistic binding protein in the treatment of cancer and/or chronic infectious diseases.

14 Claims, 10 Drawing Sheets

Specification includes a Sequence Listing.

(52) U.S. Cl.
CPC .... *C07K 16/2827* (2013.01); *A61K 2039/505* (2013.01); *C07K 2317/21* (2013.01); *C07K 2317/622* (2013.01); *C07K 2317/76* (2013.01)

(58) Field of Classification Search
CPC ............ C07K 2317/76; C07K 2317/73; C07K 2317/92; C07K 2317/565; A61P 35/00; A61K 2039/505
See application file for complete search history.

(56) References Cited

FOREIGN PATENT DOCUMENTS

| WO | WO 2014/194302 | 12/2014 |
| WO | WO 2014/194302 A2 | 12/2014 |
| WO | WO 2014/206107 | 12/2014 |
| WO | WO 2015/112800 | 7/2015 |
| WO | WO 2015/112800 A1 | 7/2015 |
| WO | WO 2015/116539 | 8/2015 |
| WO | WO 2016/020856 | 2/2016 |
| WO | WO 2016/020856 A2 | 2/2016 |
| WO | WO 2016/089873 | 6/2016 |
| WO | WO 2016/137985 | 9/2016 |
| WO | WO 2017/015560 | 1/2017 |
| WO | WO 2017/025051 | 2/2017 |
| WO | WO 2017/025051 A1 | 2/2017 |
| WO | WO 2017/062888 | 4/2017 |
| WO | WO 2017/132562 | 8/2017 |
| WO | WO 2019/180201 | 9/2019 |

OTHER PUBLICATIONS

Al Qaraghuli et al. Antibody-protein binding and conformational changes: identifying allosteric signaling pathways to engineer a better effector response. Scientific Reports (2020) 10:13696 (Year: 2020).*

Hummer et al Advances in computation structure-based antibody design Current Opinion in Structural Biology 2022, 74:102379 (Year: 2022).*

Friedman R, Boye K, Flatmark K. Molecular modelling and simulations in cancer research. Biochim Biophys Acta. Aug. 2013;1836(1):1-14. doi: 10.1016/j.bbcan.2013.02.001. Epub Feb. 14, 2013. PMID: 23416097. (Year: 2013).*

Morris, G.M., Lim-Wilby, M. (2008). Molecular Docking. In: Kukol, A. (eds) Molecular Modeling of Proteins. Methods Molecular Biology™, vol. 443. Humana Press. https://doi.org/10.1007/978-1-59745-177-2_19 (Year: 2008).*

Yan, et al. "A fully human monoclonal antibody targeting PD-L1 with potent anti-tumor activity", International Immunopharmacology vol. 31, Jan. 12, 2016, 248-256.

Alsaab, et al. "PD-1 and PD-L1 Checkpoint Signaling Inhibition for Cancer Immunotherapy: Mechanism, Combinations, and Clinical Outcome" frontiers in Pharmacology, Aug. 23, 2017, vol. 8 in 15 pages.

Shin, et al. "The evolution of checkpoint blockade as a cancer therapy: what's here, what's next?" Current Opinion in Immunology, www.sciencedirect.com, Apr. 1, 2015, vol. 33 pp. 23-35.

Gibbons, et al "Efficacy, safety and tolerability of MED14736 (durvalumab [D], a human lgG1 anti-programmed cell death-ligand-1 (PD-L1) antibody, combined with gefitinib (G): A phase I expansion in TKI-naïve patients (pts) with EGFR mutant NSCLC", Journal of Thoracic Oncology vol. 11, Suppl. 4S (2016), in 1 page.

International Search Report and Written Opinion for Int. Application No. PCT/EP2019/057239, dated Nov. 8, 2019 in 29 pages.

* cited by examiner

LAG-3

PD-L1

PD-1

ANTAGONISTIC PD-1, PD-L1 AND LAG-3 BINDING PROTEINS

The present invention relates to antagonistic antigen binding proteins, a nucleic acid encoding the antagonistic binding protein, a recombinant expression vector comprising the nucleic acid molecule, a host cell comprising the vector, a method of making the antagonistic antigen binding protein, an antagonistic binding protein produced by the method and a pharmaceutical composition comprising the antagonistic binding protein, the nucleic acid or the vector. The present invention further relates to a kit comprising the pharmaceutical composition and use of the antagonistic binding protein in the treatment of cancer and/or chronic infectious diseases.

INCORPORATION BY REFERENCE OF MATERIAL IN SEQUENCE LISTING FILE

The present application is being filed along with a Sequence Listing in electronic format. The Sequence Listing is provided as a file entitled ZSP004.001APC_ST25.txt, which was created on Sep. 4, 2020, which is 64,524 bytes in size. The information in the electronic Sequence Listing is hereby incorporated by reference in its entirety.

BACKGROUND OF THE INVENTION

Activation and proliferation of immune cells involved in anti-tumor responses is regulated by multiple stimulatory and inhibitory pathways that can be targeted by mAbs that either inhibit immunosuppressive receptors or activate co-stimulatory modulators expressed on the surface of T and B lymphocytes or NK cells (collectively named Immune Checkpoints) to enhance their tumor specific responses.

Translation of this concept into the clinic has led to the development of novel effective immunotherapies. To date, three classes of human or humanized monoclonal antibodies targeting immunosuppressive receptors such as CTLA4 (Ipilimumab), PD-1 (Nivolumab and Pembrolizumab), and PD-L1 (Atezolizumab, Durvalumab and Avelumab) have been approved for the treatment of several tumors including melanoma, NSCLC, RCC, Head and Neck Squamous Cell Carcinoma, Hodgkin Lymphoma, Urothelial Carcinoma, MSI CRC and Merkell-cell carcinoma.

Spurred by the remarkable success of these immunotherapies many more antibodies against other immunomodulatory receptors have been brought to the clinic with the expectation to find more efficacious treatments by targeting novel immune pathways. In fact, despite their success, the currently approved antibodies against Immune Checkpoints (hence collectively named Checkpoint Inhibitors; CI) are effective in only about 20%-30% of the patients. Among the new targets there are co-inhibitory receptors such as Lymphocyte Activation Gene 3 (LAG3), an immunosuppressive receptor expressed on activated T lymphocytes and T-regulatory lymphocytes, T cell Immunoglobulin 3 (TIM-3), T cell Imunoglobulin and ITIM domain (TIGIT) which are expressed on exhausted CD8+ T cells in cancer. Besides improving CD8 T cell function, Lag-3, TIM-3, and TIGIT blockade is expected to affect tumor tissue Treg cells and IL-10-producing Tr1 cells. B- and T-lymphocyte attenuator (BTLA) is another co-inhibitory receptor whose expression is induced during activation of T cells leading to inhibition of human CD8+ cancer-specific T cells. BTLA interacts with a B7 homolog, B7H4, but unlike PD-1 and CTLA-4, BTLA displays T-Cell inhibition via interaction with tumor necrosis family receptors (TNF-R), not just the B7 family of cell surface receptors.

Similarly, agonistic antibodies recognizing co-stimulatory receptors have reached the clinical stage such as OX40, a secondary co-stimulatory immune checkpoint molecule which prevents premature death of activated lymphocytes, and 41BB expressed on activated CD4 and CD8 T lymphocytes. Other co-stimulatory proteins which are considered good targets for antibody-mediated immunotherapy are Inducible T-cell costimulator (ICOS), which is an immune checkpoint protein belonging to the CD28-superfamily, and CD27, a member of the tumor necrosis factor receptor superfamily.

Cancer immunotherapy based on immunomodulatory antibodies is becoming a mainstay of modern oncology. Checkpoint Inhibitors (i.e.: anti-PD-1, anti-PD-L1 and anti-CTLA4) have been shown to achieve unprecedented efficacy with long lasting clinical benefit. Perhaps most importantly, these antibodies have an extremely wide range of applications with the currently approved ones used for the treatment of several tumors. This notwithstanding, treatment efficacy with CI is still limited to 20%-30% of the population, and could not be shown in highly prevalent cancer types such as Colon and Rectal cancer, Breast Cancer and Prostate Cancer. However, the recent enrichment of armory of monoclonal antibodies against new targets with agonistic or antagonistic activity for co-stimulatory or inhibitory receptors, respectively, allow to design new combination therapies to enhance the potential of the immune-based cancer therapy.

Antibodies against different immune checkpoint receptors can also be combined to achieve additive or synergistic activity, potentially translating into a better efficacy. Proof of concept for this approach was provided by the finding of increased efficacy of the Ipilimumab and Nivolumab combination versus monotherapy in the treatment of metastatic melanoma.

Currently, over one thousand clinical trials with already approved or novel antibodies against immunomodulatory receptors used in monotherapy or in combination with other biologics or small molecules are being carried out. Because large sets of antibodies against the different immune checkpoints are not available in a single lab, most of these trials are being developed without pre-clinical head-to-head comparison to allow for prediction of the most effective treatments.

The present inventors have generated a large repertoire of fully human mAbs against several immune-regulatory checkpoints using a strategy for rapid, parallel screening of phage displayed antibody libraries by directly panning on activated human lymphocytes. It was demonstrated that the thus selected mAbs are endowed with high binding affinity for their targets and improved functional activity on lymphocytes.

SUMMARY OF THE INVENTION

In a first aspect, the present invention provides an antagonistic antigen binding protein that specifically binds to PD-1, wherein said antigen binding protein competes for binding to PD-1 with an antibody
  (i) comprising a heavy chain variable region of the amino acid sequence in SEQ ID NO: 2; and a light chain variable region of the amino acid sequence in SEQ ID NO: 3; or (ii) comprising a heavy chain variable region of the amino acid sequence in SEQ ID NO: 11; and a light chain variable region of the amino acid sequence in SEQ ID NO: 12.

In a second aspect, the present invention relates to an antagonistic antigen binding protein that specifically binds to PD-L1, wherein said antigen binding protein competes for binding to PD-L1 with an antibody
(i) comprising a heavy chain variable region of the amino acid sequence in SEQ ID NO: 20; and a light chain variable region of the amino acid sequence in SEQ ID NO: 21; or
(ii) comprising a heavy chain variable region of the amino acid sequence in SEQ ID NO: 29; and a light chain variable region of the amino acid sequence in SEQ ID NO: 30;
(iii) comprising a heavy chain variable region of the amino acid sequence in SEQ ID NO: 83; and a light chain variable region of the amino acid sequence in SEQ ID NO: 84; or
(iv) comprising a heavy chain variable region of the amino acid sequence in SEQ ID NO: 92; and a light chain variable region of the amino acid sequence in SEQ ID NO: 93; or
(v) comprising a heavy chain variable region of the amino acid sequence in SEQ ID NO: 101; and a light chain variable region of the amino acid sequence in SEQ ID NO: 102.

In a third aspect, the present invention relates to an antagonistic antigen binding protein that specifically binds to LAG-3, wherein said antigen binding protein competes for binding to LAG-3 with an antibody
(i) comprising a heavy chain variable region of the amino acid sequence in SEQ ID NO: 38; and a light chain variable region of the amino acid sequence in SEQ ID NO: 39;
(ii) comprising a heavy chain variable region of the amino acid sequence in SEQ ID NO: 47; and a light chain variable region of the amino acid sequence in SEQ ID NO: 48;
(iii) comprising a heavy chain variable region of the amino acid sequence in SEQ ID NO: 56; and a light chain variable region of the amino acid sequence in SEQ ID NO: 57;
(iv) comprising a heavy chain variable region of the amino acid sequence in SEQ ID NO: 65; and a light chain variable region of the amino acid sequence in SEQ ID NO: 66; or
(v) comprising a heavy chain variable region of the amino acid sequence in SEQ ID NO: 74; and a light chain variable region of the amino acid sequence in SEQ ID NO: 75.

In a fourth aspect, the present invention relates to an antagonistic antigen binding protein that specifically binds to PD-1, wherein said antigen binding protein comprises either
(i) a combination of a light chain variable domain and a heavy chain variable domain selected from the group of combinations consisting of:
  a light chain variable domain having a sequence with at least 90% identity to SEQ ID NO: 3 and a heavy chain variable domain having a sequence with at least 90% identity to SEQ ID NO: 2;
  a light chain variable domain having a sequence with at least 90% identity to SEQ ID NO: 12 and a heavy chain variable domain having a sequence with at least 90% identity to SEQ ID NO: 11;
(ii) a combination of a complementarity determining region 3 of the heavy chain (CDRH3) and a complementarity determining region 3 of the light chain (CDRL3) selected from the group of combinations consisting of:
  a CDRH3 comprising or consisting of the amino acid sequence of SEQ ID NO: 8 and
  a CDRL3 comprising or consisting of the amino acid sequence of SEQ ID NO: 9;
  a CDRH3 comprising or consisting of the amino acid sequence of SEQ ID NO: 17 and
  a CDRL3 comprising or consisting of the amino acid sequence of SEQ ID NO: 18.

In a fifth aspect, the present invention relates to an antagonistic antigen binding protein that specifically binds to PD-L1, wherein said antigen binding protein comprises either (i) a combination of a light chain variable domain and a heavy chain variable domain selected from the group of combinations consisting of:
  a light chain variable domain having a sequence with at least 90% identity to SEQ ID NO: 21 and
  a heavy chain variable domain having a sequence with at least 90% identity to SEQ ID NO: 20;
  a light chain variable domain having a sequence with at least 90% identity to SEQ ID NO: 30 and
  a heavy chain variable domain having a sequence with at least 90% identity to SEQ ID NO: 29;
  a light chain variable domain having a sequence with at least 90% identity to SEQ ID NO: 84 and
  a heavy chain variable domain having a sequence with at least 90% identity to SEQ ID NO: 83;
  a light chain variable domain having a sequence with at least 90% identity to SEQ ID NO: 93 and
  a heavy chain variable domain having a sequence with at least 90% identity to SEQ ID NO: 92;
  a light chain variable domain having a sequence with at least 90% identity to SEQ ID NO: 102 and
  a heavy chain variable domain having a sequence with at least 90% identity to SEQ ID NO: 101;
(ii) a combination of a complementarity determining region 3 of the heavy chain (CDRH3) and a complementarity determining region 3 of the light chain (CDRL3) selected from the group of combinations consisting of:
  a CDRH3 comprising or consisting of the amino acid sequence of SEQ ID NO: 26 and
  a CDRL3 comprising or consisting of the amino acid sequence of SEQ ID NO: 27;
  a CDRH3 comprising or consisting of the amino acid sequence of SEQ ID NO: 35 and
  a CDRL3 comprising or consisting of the amino acid sequence of SEQ ID NO: 36;
  a CDRH3 comprising or consisting of the amino acid sequence of SEQ ID NO: 89 and
  a CDRL3 comprising or consisting of the amino acid sequence of SEQ ID NO: 90;
  a CDRH3 comprising or consisting of the amino acid sequence of SEQ ID NO: 98 and
  a CDRL3 comprising or consisting of the amino acid sequence of SEQ ID NO: 99;
  a CDRH3 comprising or consisting of the amino acid sequence of SEQ ID NO: 107 and
  a CDRL3 comprising or consisting of the amino acid sequence of SEQ ID NO: 108.

In a sixth aspect, the present invention relates to an antagonistic antigen binding protein that specifically binds to LAG-3, wherein said antigen binding protein comprises either (i) a combination of a light chain variable domain and a heavy chain variable domain selected from the group of combinations consisting of:
   a light chain variable domain having a sequence with at least 90% identity to SEQ ID NO: 39 and
   a heavy chain variable domain having a sequence with at least 90% identity to SEQ ID NO: 38;
   a light chain variable domain having a sequence with at least 90% identity to SEQ ID NO: 48 and
   a heavy chain variable domain having a sequence with at least 90% identity to SEQ ID NO: 47;
   a light chain variable domain having a sequence with at least 90% identity to SEQ ID NO: 57 and
   a heavy chain variable domain having a sequence with at least 90% identity to SEQ ID NO: 56;
   a light chain variable domain having a sequence with at least 90% identity to SEQ ID NO: 66 and
   a heavy chain variable domain having a sequence with at least 90% identity to SEQ ID NO: 65;
   a light chain variable domain having a sequence with at least 90% identity to SEQ ID NO: 75 and
   a heavy chain variable domain having a sequence with at least 90% identity to SEQ ID NO: 74;

(ii) a combination of a complementarity determining region 3 of the heavy chain (CDRH3) and a complementarity determining region 3 of the light chain (CDRL3) selected from the group of combinations consisting of:
   a CDRH3 comprising or consisting of the amino acid sequence of SEQ ID NO: 44 and
   a CDRL3 comprising or consisting of the amino acid sequence of SEQ ID NO: 45;
   a CDRH3 comprising or consisting of the amino acid sequence of SEQ ID NO: 53 and
   a CDRL3 comprising or consisting of the amino acid sequence of SEQ ID NO: 54;
   a CDRH3 comprising or consisting of the amino acid sequence of SEQ ID NO: 62 and
   a CDRL3 comprising or consisting of the amino acid sequence of SEQ ID NO: 63;
   a CDRH3 comprising or consisting of the amino acid sequence of SEQ ID NO: 71 and
   a CDRL3 comprising or consisting of the amino acid sequence of SEQ ID NO: 72;
   a CDRH3 comprising or consisting of the amino acid sequence of SEQ ID NO: 80 and
   a CDRL3 comprising or consisting of the amino acid sequence of SEQ ID NO: 81.

In a seventh aspect, the present invention relates to a nucleic acid encoding the antagonistic antigen binding protein of any one of aspects 1 to 6 of the present invention.

In an eighth aspect, the present invention relates to a recombinant expression vector comprising a nucleic acid molecule according to the seventh aspect.

In a ninth aspect, the present invention relates to a host cell comprising the vector of the eighth aspect of the present invention.

In a tenth aspect, the present invention relates to a method of making the antagonistic antigen binding protein of any one of aspects 1 to 6 of the present invention comprising the step of preparing said antigen binding protein from a host cell expressing said antigen binding protein.

In an eleventh aspect, the present invention relates to an antagonistic antigen binding protein produced by the expression of recombinant DNA in the host cell of the ninth aspect of the present invention.

In a twelfth aspect, the present invention relates to a pharmaceutical composition comprising at least one antagonistic antigen binding protein according to any one of aspects 1 to 6 of the present invention, the nucleic acid according to the seventh aspect of the present invention or the vector according to the eighth aspect of the present invention and a pharmaceutically acceptable carrier.

In a thirteenth aspect, the present invention relates to a kit comprising the pharmaceutical composition according to the twelfth aspect of the present invention and optionally at least one further active agent.

In a fourteenth aspect, the present invention relates to the antagonistic antigen binding protein according to any one of aspects 1 to 6 of the present invention, the nucleic acid of the seventh aspect of the present invention, the vector of the eighth aspect of the present invention or the pharmaceutical composition of the twelfth aspect of the present invention for use in the treatment of cancer and/or chronic infectious disease.

LIST OF FIGURES

In the following, the content of the figures comprised in this specification is described. In this context please also refer to the detailed description of the invention above and/or below.

FIG. 1: Immunome screening. The screening procedure started from a universal cycle, common to the different targets, performed by panning the unselected library on activated PBMCs (inner circle). Each divergent circle sector describes the enrichment profiles for the best ten scFv clones of the indicated targets, scored according to their counts per million value. The lines within each sector connect the individual enrichments, obtained after cycle 2 (small circles) and cycle 3 (large circles). Cycles 2 and 3 were both performed on the recombinant proteins.

Figure 2:
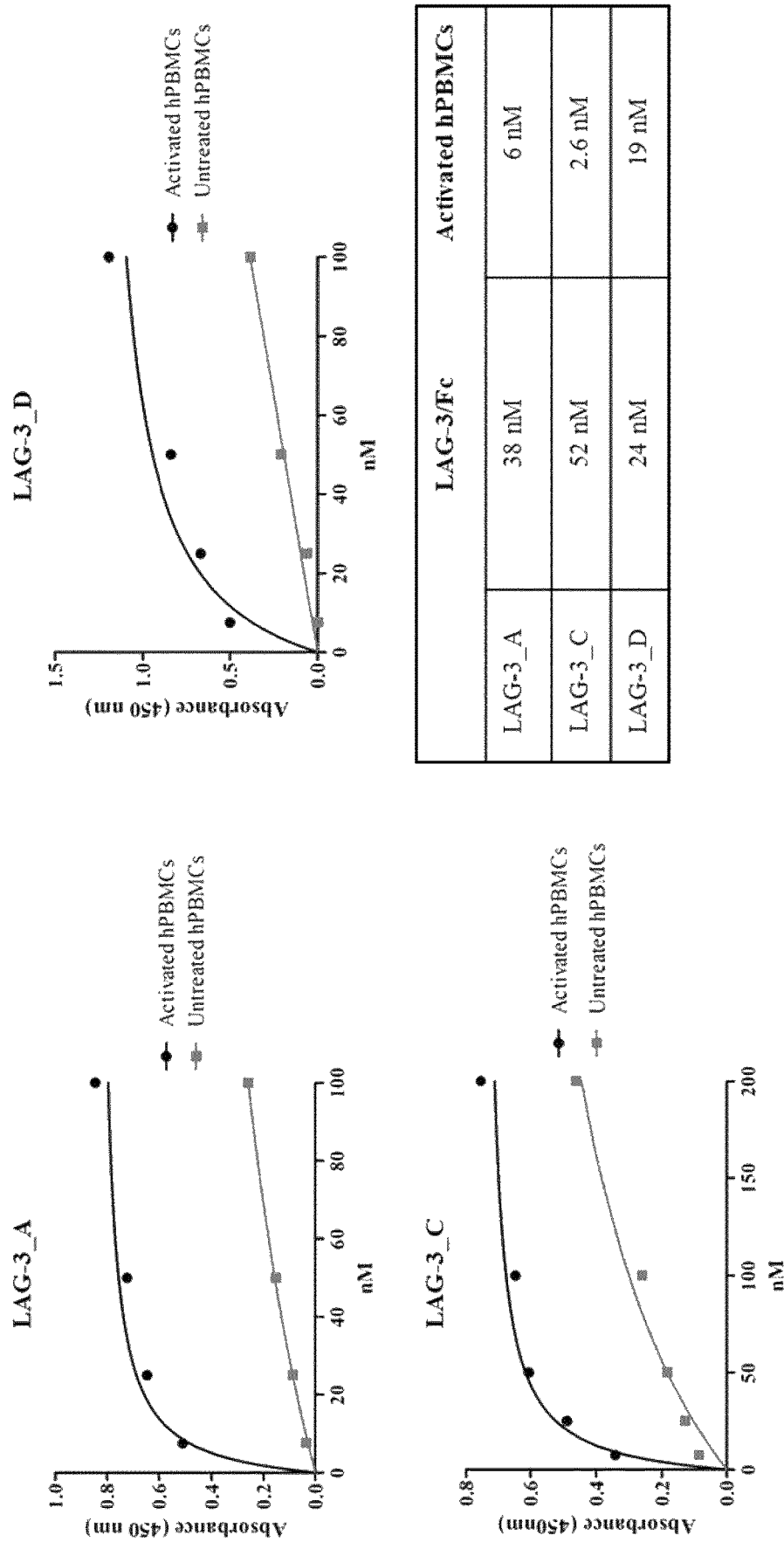
Figure 2:
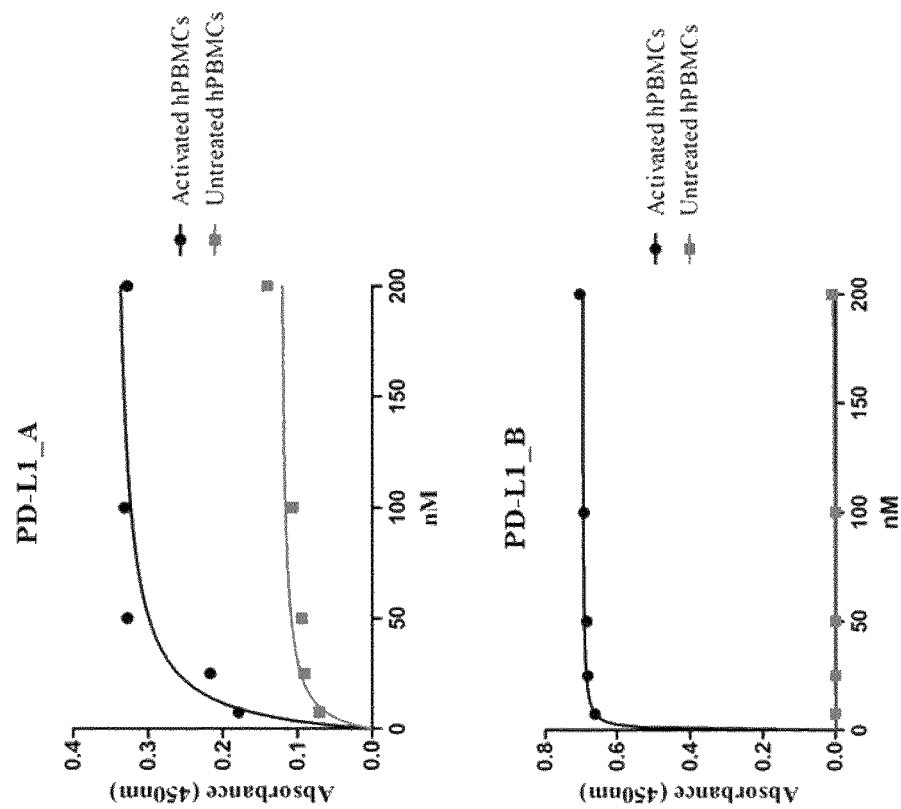
Figure 2:
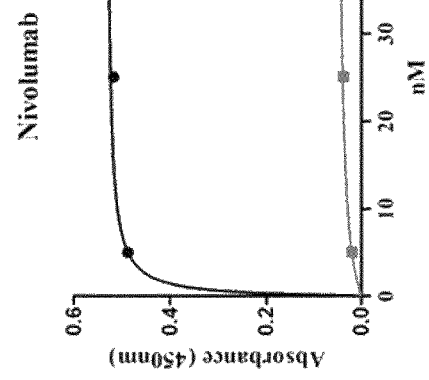
Figure 2:
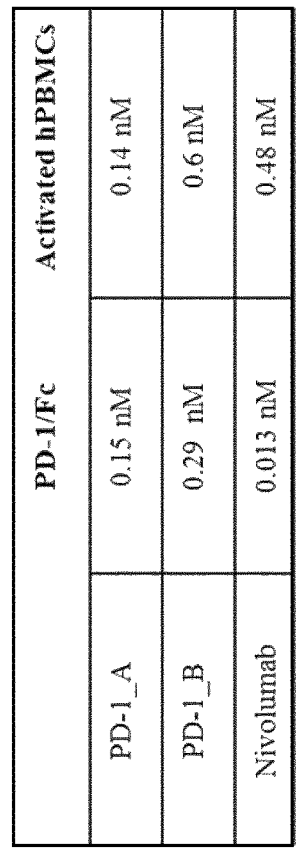
Figure 2:
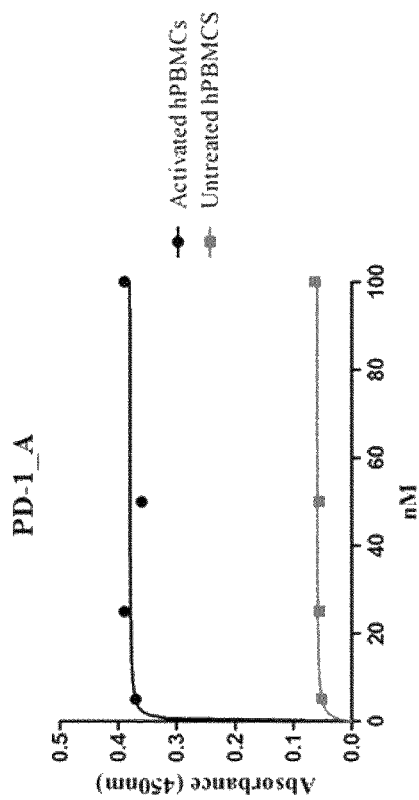
Figure 2:
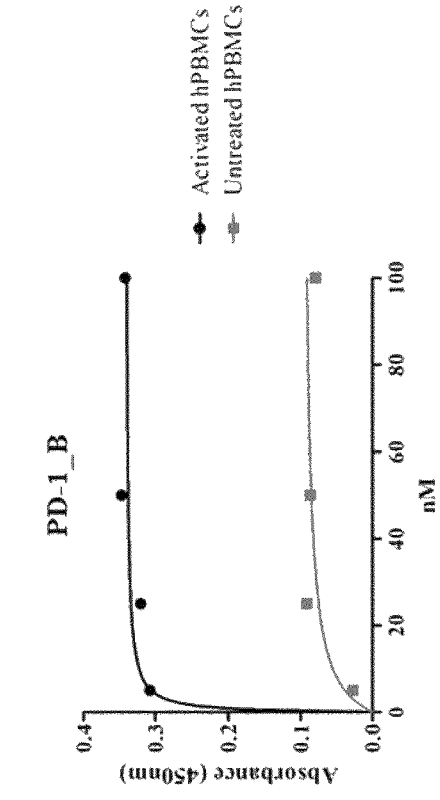

FIG. 2: Binding affinity of the selected antibodies for lymphocytes. The ELISA assays were performed with mAbs used at increasing concentrations (7.5 nM, 25 nM, 50 nM, 100 nM) on activated hPBMCs (black curves) or untreated hPBMCs (grey curves). The antibodies were tested by ELISA assays at increasing concentrations also on each recombinant protein/Fc and the Kd values are reported in the tables.

Figure 3:
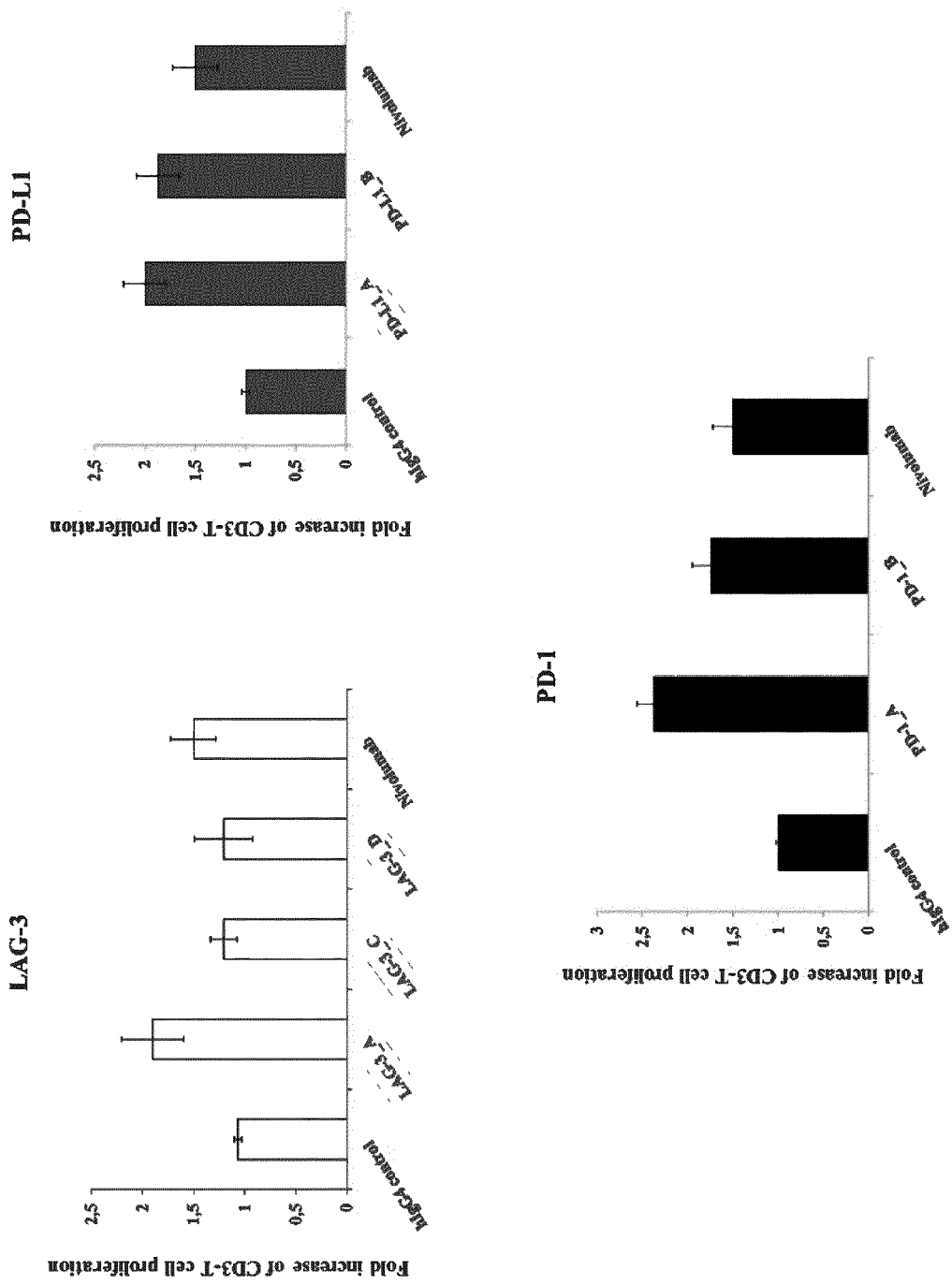

FIG. 3: Proliferation of hPBMCs after stimulation with PHA at 2.5 g/ml in the absence or in the presence of the immunomodulatory antibodies. Fold increase of CD3-T cell proliferation determined by the indicated selected antibodies was measured with respect to activation of hPBMCs with PHA at 2.5 μg/ml in the absence of antibodies or in the presence of an unrelated IgG4.

Figure 4:
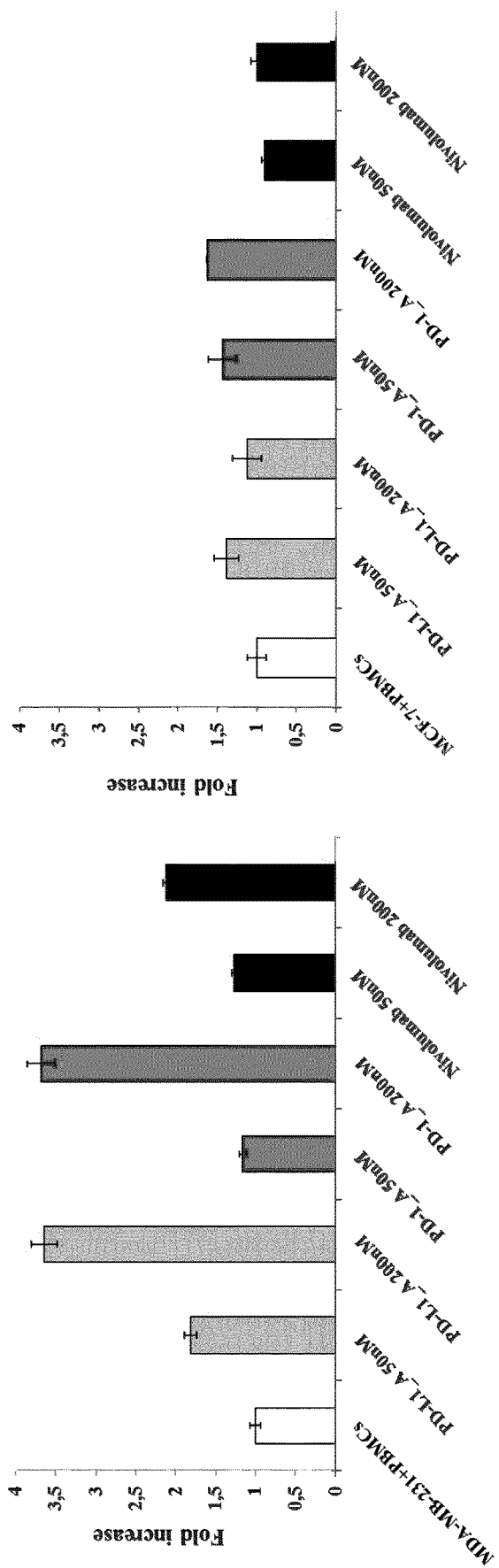

FIG. 4: Effects of anti-PD-1 and anti-PD-L1 antibodies on Lymphocyte proliferation as induced by tumor cells. Fold increase of hPBMCs proliferation as determined by normalized absorbance values obtained by ELISA with anti-BrdU antibodies in hPBMCs samples co-cultivated with MDA-MB-231(A) or MCF-7 (B) tumor cells in the absence (white bar) or in the presence of increasing concentrations (50 nM and 200 nM) of PD-L1_A (light grey bars) or PD-1_A (grey bars) antibodies for 72 hours at 37° C. Nivolumab was used, in both the experiments, as a positive control (black bars).

Figure 5:
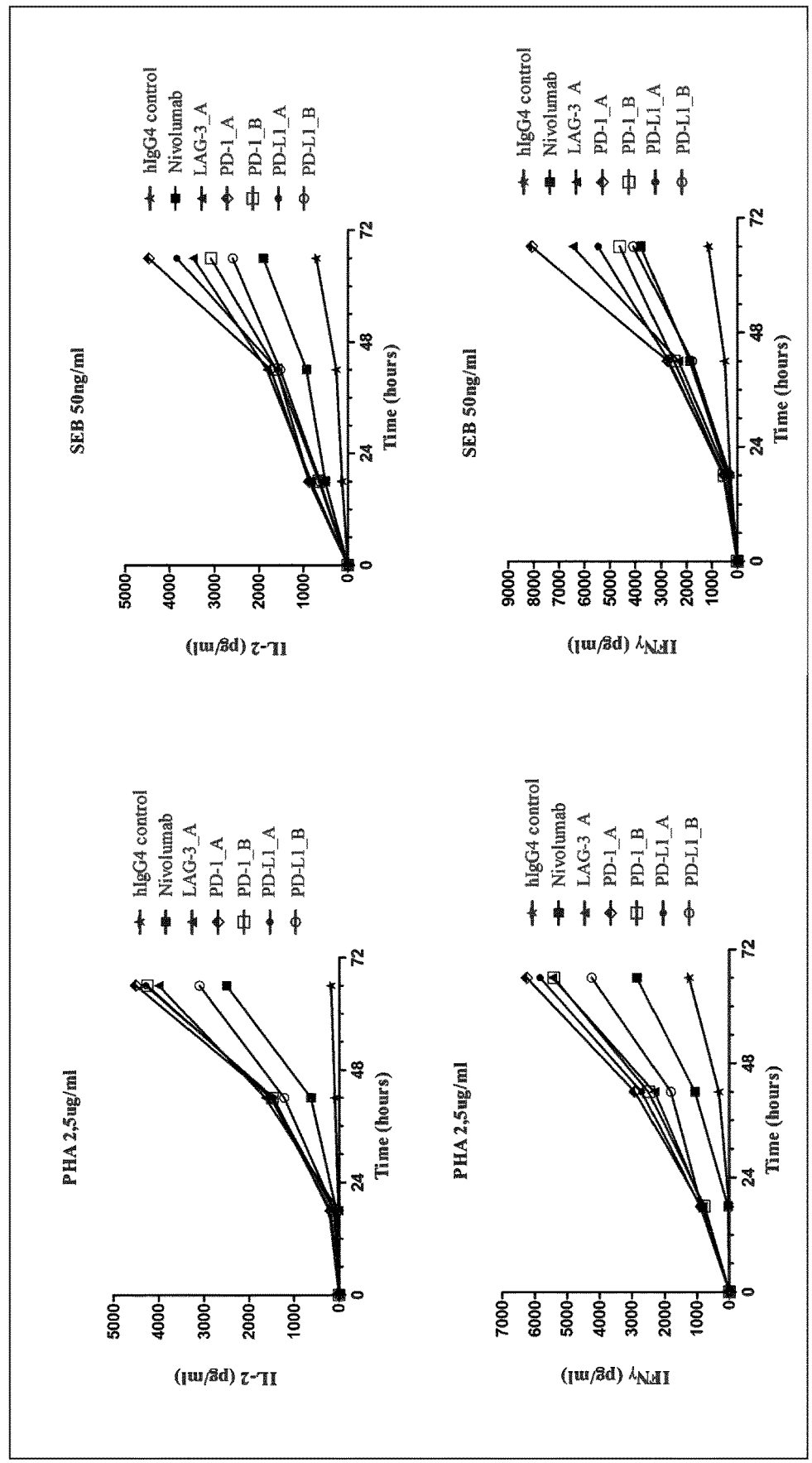

FIG. 5: Effects of the novel immunomodulatory antibodies on secretion of cytokines by stimulated T-cells. IL-2 and IFNγ values obtained by ELISA assays on supernatants of hPBMCs stimulated with PHA (2.5 µg/mL) or SEB (50 ng/mL) in the absence or in the presence of the antibodies LAG-3_A, PD-1_A, PD-1_B, PD-L1_A, PD-L1_B for 18-66 hours at 37° C. Nivolumab and an unrelated antibody were used as a positive and negative control, respectively.

Figure 6:
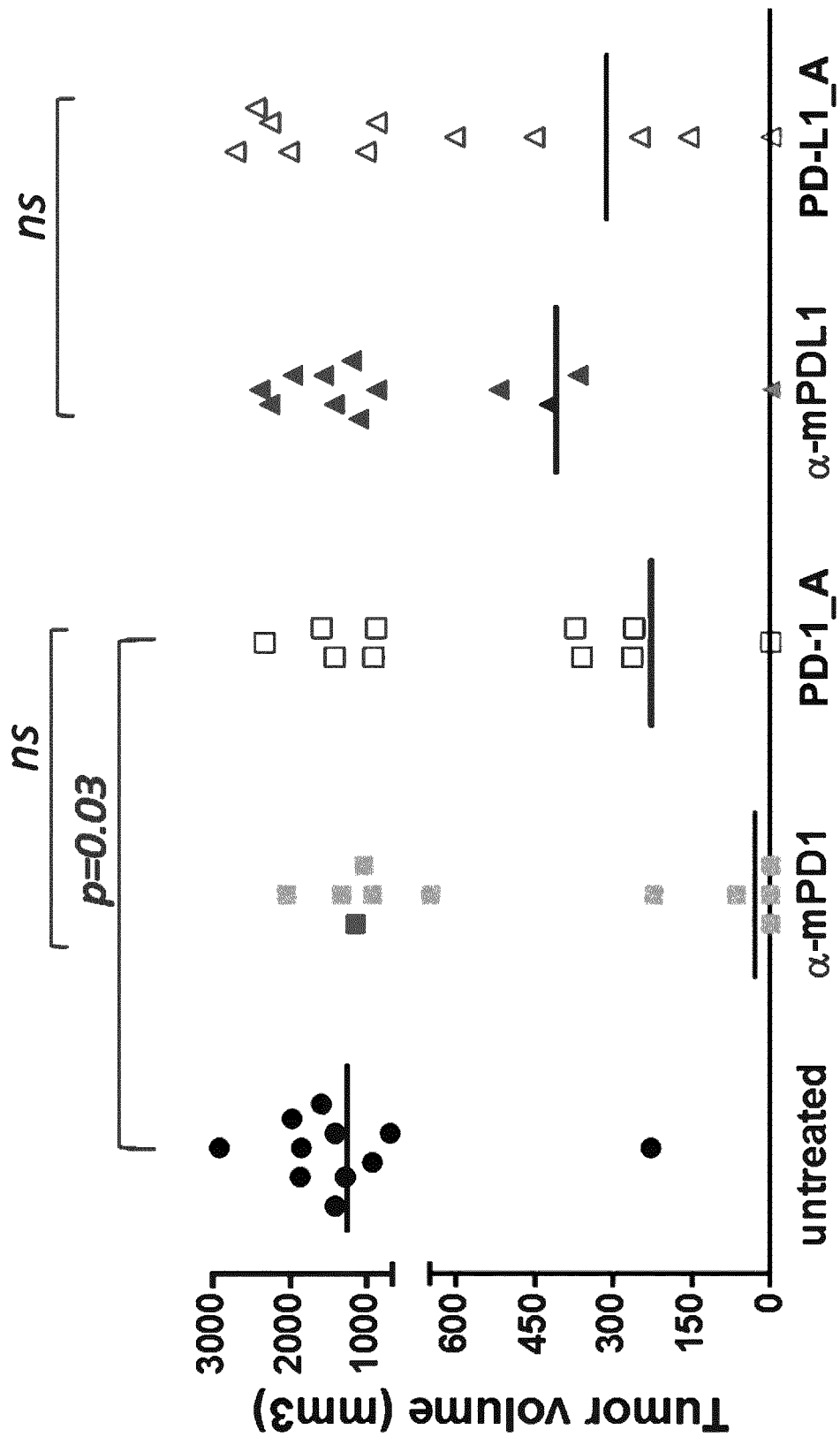

FIG. 6: In vivo antitumor activities of PD-1_A and PD-L1_A antibodies. Tumor growth in mice inoculated with CT26 cells at day 0 and treated with PD-1_A, PD-L1_A or positive control antibodies reacting against murine PD-1 and PD-L1 (α_mPD-1, α-mPD-L1) at day 3, 6, and 10. Tumor volume 21 days post tumor challenge is shown.

Figure 7:
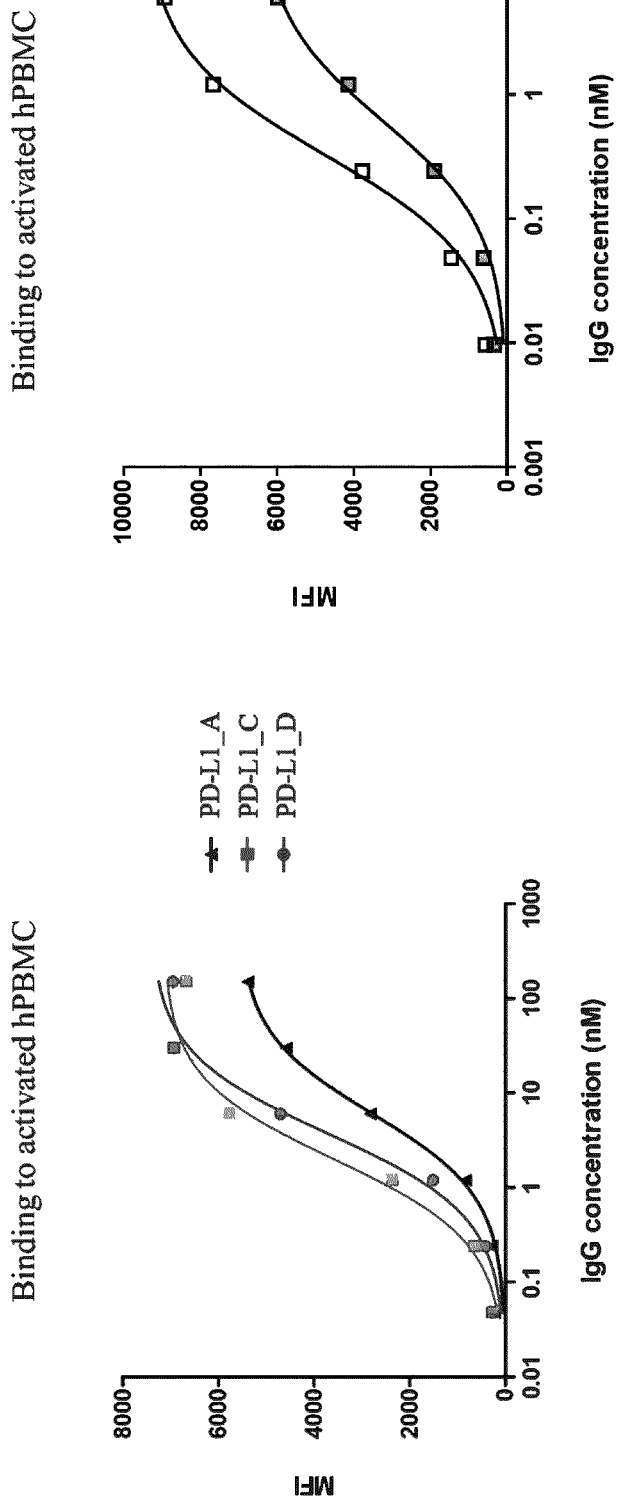

FIG. 7: Binding of the anti-PD-L1 antibodies to lymphocytes. To assess whether antibodies PD-L1_C, PD-L1_D and PD-L1_E were able to bind PD-L1 protein in comparison with PD-L1_A, binding curves of all these mAbs were generated to human activated lymphocytes. Human PBMCs isolated from healthy donors were activated with anti-CD3/CD28 beads to stimulate PD-L1 expression. Then, PD-L1_A, PD-L1_C, PD-L1_D, PD-L1 E antibodies were added in a wide range of concentrations and analyzed by flow cytometry (CytoFLEX flow cytometer, Beckman Coulter). The mean fluorescence intensity of PD-L1-binding lymphocytes was plotted against the antibody concentration (FIG. 7 A, B).

Figure 8:
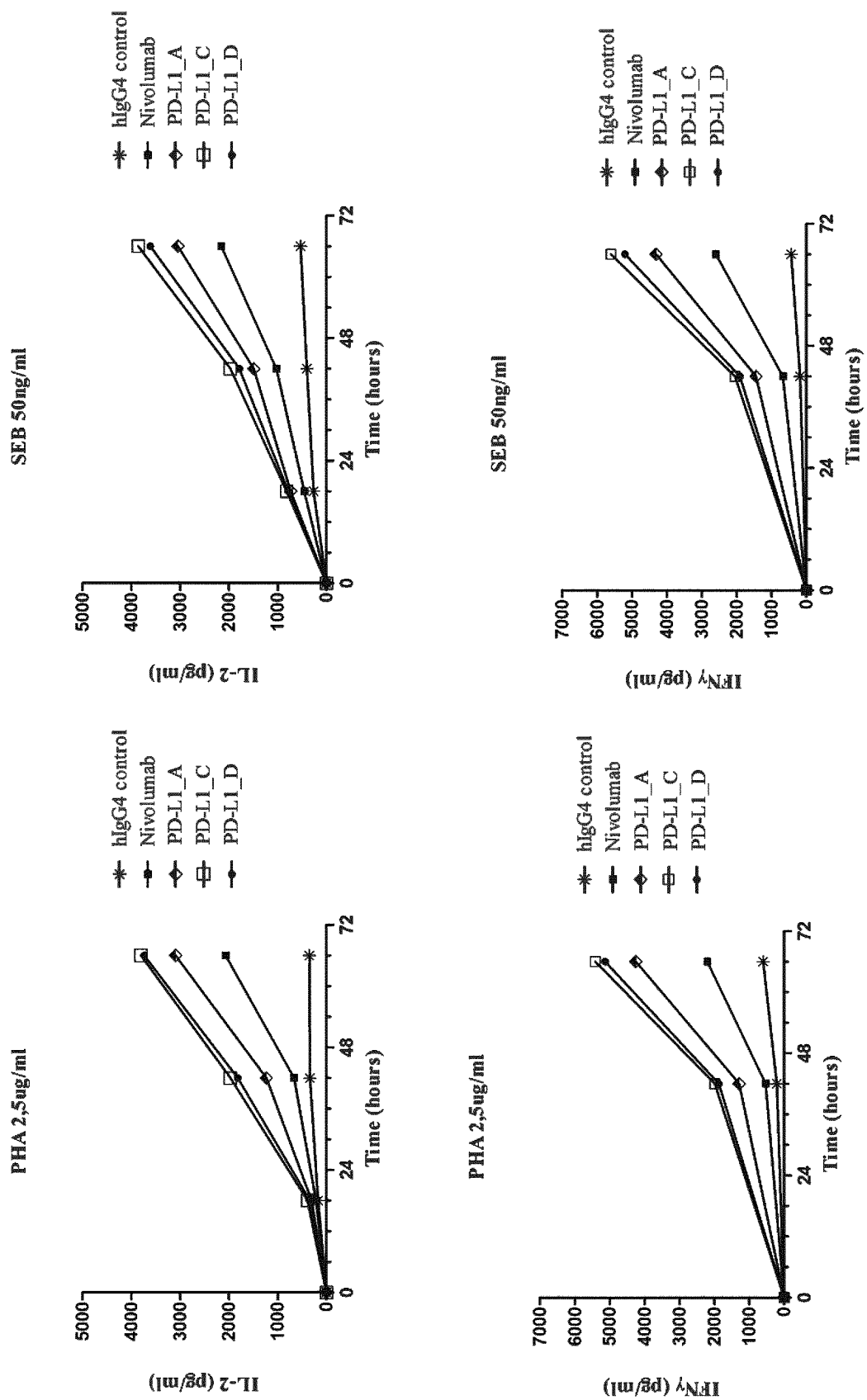

FIG. 8: Effects of anti PD-L1 antibodies on secretion of cytokines by stimulated T-cells. IL-2 and IFNγ values obtained by ELISA assays on supernatants of hPBMCs stimulated with PHA (2.5 µg/mL) or SEB (50 ng/mL) in the absence or in the presence of the antibodies PD-L1_A, PD-L1_C and PD-L1_D for 18-66 hours at 37° C. Nivolumab and an unrelated antibody were used as a positive and negative control, respectively.

LIST OF SEQUENCES

SEQ ID NO:1 Amino acid sequence of PD-1_A
SEQ ID NO:2 Amino acid sequence of PD-1_A; VH
SEQ ID NO:3 Amino acid sequence of PD-1_A; VL
SEQ ID NO:4 Amino acid sequence of PD-1_A; CDRH1
SEQ ID NO:5 Amino acid sequence of PD-1_A; CDRL1
SEQ ID NO:6 Amino acid sequence of PD-1_A; CDRH2
SEQ ID NO:7 Amino acid sequence of PD-1_A; CDRL2
SEQ ID NO:8 Amino acid sequence of PD-1_A; CDRH3
SEQ ID NO:9 Amino acid sequence of PD-1_A; CDRL3
SEQ ID NO:10 Amino acid sequence of PD-1_B
SEQ ID NO:11 Amino acid sequence of PD-1_B; VH
SEQ ID NO:12 Amino acid sequence of PD-1_B; VL
SEQ ID NO:13 Amino acid sequence of PD-1_B; CDRH1
SEQ ID NO:14 Amino acid sequence of PD-1_B; CDRL1
SEQ ID NO:15 Amino acid sequence of PD-1_B; CDRH2
SEQ ID NO:16 Amino acid sequence of PD-1_B; CDRL2
SEQ ID NO:17 Amino acid sequence of PD-1_B; CDRH3
SEQ ID NO:18 Amino acid sequence of PD-1_B; CDRL3
SEQ ID NO:19 Amino acid sequence of PD-L1_A
SEQ ID NO:20 Amino acid sequence of PD-L1_A; VH
SEQ ID NO:21 Amino acid sequence of PD-L1_A; VL
SEQ ID NO:22 Amino acid sequence of PD-L1_A; CDRH1
SEQ ID NO:23 Amino acid sequence of PD-L1_A; CDRL1
SEQ ID NO:24 Amino acid sequence of PD-L1_A; CDRH2
SEQ ID NO:25 Amino acid sequence of PD-L1_A; CDRL2
SEQ ID NO:26 Amino acid sequence of PD-L1_A; CDRH3
SEQ ID NO:27 Amino acid sequence of PD-L1_A; CDRL3
SEQ ID NO:28 Amino acid sequence of PD-L1 B
SEQ ID NO:29 Amino acid sequence of PD-L1_B; VH
SEQ ID NO:30 Amino acid sequence of PD-L1_B; VL
SEQ ID NO:31 Amino acid sequence of PD-L1_B; CDRH1
SEQ ID NO:32 Amino acid sequence of PD-L1_B; CDRL1
SEQ ID NO:33 Amino acid sequence of PD-L1_B; CDRH2
SEQ ID NO:34 Amino acid sequence of PD-L1_B; CDRL2
SEQ ID NO:35 Amino acid sequence of PD-L1_B; CDRH3
SEQ ID NO:36 Amino acid sequence of PD-L1_B; CDRL3
SEQ ID NO:37 Amino acid sequence of LAG-3_A
SEQ ID NO:38 Amino acid sequence of LAG-3_A; VH
SEQ ID NO:39 Amino acid sequence of LAG-3_A; VL
SEQ ID NO:40 Amino acid sequence of LAG-3_A; CDRH1
SEQ ID NO:41 Amino acid sequence of LAG-3_A; CDRL1
SEQ ID NO:42 Amino acid sequence of LAG-3_A; CDRH2
SEQ ID NO:43 Amino acid sequence of LAG-3_A; CDRL2
SEQ ID NO:44 Amino acid sequence of LAG-3_A; CDRH3
SEQ ID NO:45 Amino acid sequence of LAG-3_A; CDRL3
SEQ ID NO:46 Amino acid sequence of LAG-3_C
SEQ ID NO:47 Amino acid sequence of LAG-3_C; VH
SEQ ID NO:48 Amino acid sequence of LAG-3_C; VL
SEQ ID NO:49 Amino acid sequence of LAG-3_C; CDRH1
SEQ ID NO:50 Amino acid sequence of LAG-3_C; CDRL1
SEQ ID NO:51 Amino acid sequence of LAG-3_C; CDRH2
SEQ ID NO:52 Amino acid sequence of LAG-3_C; CDRL2
SEQ ID NO:53 Amino acid sequence of LAG-3_C; CDRH3
SEQ ID NO:54 Amino acid sequence of LAG-3_C; CDRL3
SEQ ID NO:55 Amino acid sequence of LAG-3_D
SEQ ID NO:56 Amino acid sequence of LAG-3_D; VH
SEQ ID NO:57 Amino acid sequence of LAG-3_D; VL
SEQ ID NO:58 Amino acid sequence of LAG-3_D; CDRH1
SEQ ID NO:59 Amino acid sequence of LAG-3_D; CDRL1
SEQ ID NO:60 Amino acid sequence of LAG-3_D; CDRH2
SEQ ID NO:61 Amino acid sequence of LAG-3_D; CDRL2
SEQ ID NO:62 Amino acid sequence of LAG-3_D; CDRH3
SEQ ID NO:63 Amino acid sequence of LAG-3_D; CDRL3
SEQ ID NO:64 Amino acid sequence of LAG-3_B
SEQ ID NO:65 Amino acid sequence of LAG-3_B; VH
SEQ ID NO:66 Amino acid sequence of LAG-3_B; VL
SEQ ID NO:67 Amino acid sequence of LAG-3_B; CDRH1

SEQ ID NO:68 Amino acid sequence of LAG-3_B; CDRL1
SEQ ID NO:69 Amino acid sequence of LAG-3_B; CDRH2
SEQ ID NO:70 Amino acid sequence of LAG-3_B; CDRL2
SEQ ID NO:71 Amino acid sequence of LAG-3_B; CDRH3
SEQ ID NO:72 Amino acid sequence of LAG-3_B; CDRL3
SEQ ID NO:73 Amino acid sequence of LAG-3_E
SEQ ID NO:74 Amino acid sequence of LAG-3_E; VH
SEQ ID NO:75 Amino acid sequence of LAG-3_E; VL
SEQ ID NO:76 Amino acid sequence of LAG-3_E; CDRH1
SEQ ID NO:77 Amino acid sequence of LAG-3_E; CDRL1
SEQ ID NO:78 Amino acid sequence of LAG-3_E; CDRH2
SEQ ID NO:79 Amino acid sequence of LAG-3_E; CDRL2
SEQ ID NO:80 Amino acid sequence of LAG-3_E; CDRH3
SEQ ID NO:81 Amino acid sequence of LAG-3_E; CDRL3
SEQ ID NO:82 Amino acid sequence of PD-L1_C
SEQ ID NO:83 Amino acid sequence of PD-L1_C; VH
SEQ ID NO:84 Amino acid sequence of PD-L1_C; VL
SEQ ID NO:85 Amino acid sequence of PD-L1_C; CDRH1
SEQ ID NO:86 Amino acid sequence of PD-L1_C; CDRL1
SEQ ID NO:87 Amino acid sequence of PD-L1_C; CDRH2
SEQ ID NO:88 Amino acid sequence of PD-L1_C; CDRL2
SEQ ID NO:89 Amino acid sequence of PD-L1_C; CDRH3
SEQ ID NO:90 Amino acid sequence of PD-L1_C; CDRL3
SEQ ID NO:91 Amino acid sequence of PD-L1_D
SEQ ID NO:92 Amino acid sequence of PD-L1_D; VH
SEQ ID NO:93 Amino acid sequence of PD-L1_D; VL
SEQ ID NO:94 Amino acid sequence of PD-L1_D; CDRH1
SEQ ID NO:95 Amino acid sequence of PD-L1_D; CDRL1
SEQ ID NO:96 Amino acid sequence of PD-L1 D; CDRH2
SEQ ID NO:97 Amino acid sequence of PD-L1_D; CDRL2
SEQ ID NO:98 Amino acid sequence of PD-L1 D; CDRH3
SEQ ID NO:99 Amino acid sequence of PD-L1_D; CDRL3
SEQ ID NO:100 Amino acid sequence of PD-L1 E
SEQ ID NO:101 Amino acid sequence of PD-L1_E; VH
SEQ ID NO:102 Amino acid sequence of PD-L1_E; VL
SEQ ID NO:103 Amino acid sequence of PD-L1_E; CDRH1
SEQ ID NO:104 Amino acid sequence of PD-L1_E; CDRL1
SEQ ID NO:105 Amino acid sequence of PD-L1_E; CDRH2
SEQ ID NO:106 Amino acid sequence of PD-L1_E; CDRL2
SEQ ID NO:107 Amino acid sequence of PD-L1_E; CDRH3
SEQ ID NO:108 Amino acid sequence of PD-L1_E; CDRL3

DETAILED DESCRIPTIONS OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. In the following passages, different aspects of the invention are defined in more detail. Each aspect so defined may be combined with any other aspect or aspects unless clearly indicated to the contrary. In particular, any feature indicated as being optional, preferred or advantageous may be combined with any other feature or features indicated as being optional, preferred or advantageous.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the following, the elements of the present invention will be described. These elements are listed with specific embodiments; however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Definitions

In the following, some definitions of terms frequently used in this specification are provided. These terms will, in each instance of its use, in the remainder of the specification have the respectively defined meaning and preferred meanings.

As used in this specification and the appended claims, the singular forms "a", "an", and "the" include plural referents, unless the content clearly dictates otherwise.

The term "antagonistic" as used herein refers to any molecule or part of a molecule that blocks or dampens a biological response by binding to and blocking a second molecule that normally provides said biological response. The term "antagonistic" includes "competitive antagonists", "non-competitive antagonists", uncompetitive antagonists", partial agonists" and inverse agonists".

The term "PD-1" as used herein refers to programmed cell death protein 1, also known as CD279.

The term "PD-L1" as used herein refers to programmed death-ligand 1, also known as CD274 or B7 homolog 1 (B7-H1).

The term "LAG-3" as used herein refers to lymphocyte-activation gene 3, also known as CD223.

The term "antigen binding protein", as used herein, refers to any molecule or part of a molecule that can specifically bind to a target molecule or target epitope. Preferred binding proteins in the context of the present application are (a) antibodies or antigen-binding fragments thereof; (b) oligonucleotides; (c) antibody-like proteins; or (d) peptidomimetics.

As used herein, a first compound (e.g. an antibody) is considered to "bind" to a second compound (e.g. an antigen, such as a target protein), if it has a dissociation constant $K_d$ to said second compound of 1 mM or less, preferably 100 μM or less, preferably 50 μM or less, preferably 30 UM or less, preferably 20 UM or less, preferably 10 μM or less, preferably 5 μM or less, more preferably 1 μM or less, more preferably 900 nM or less, more preferably 800 nM or less, more preferably 700 nM or less, more preferably 600 nM or less, more preferably 500 nM or less, more preferably 400 nM or less, more preferably 300 nM or less, more preferably 200 nM or less, even more preferably 100 nM or less, even more preferably 90 nM or less, even more preferably 80 nM or less, even more preferably 70 nM or less, even more preferably 60 nM or less, even more preferably 50 nM or less, even more preferably 40 nM or less, even more preferably 30 nM or less, even more preferably 20 nM or less, and even more preferably 10 nM or less.

Typically, a first compound (e.g. an antibody) is considered to "bind" to a second compound (e.g. an antigen, such as a target protein), if it has a dissociation constant $K_d$ to said second compound between 10 nM and 1 mM, 10 nM and 100 μM, 10 nM and 50 μM, 10 nM and 1 μM, preferably 10 nM and 900 nM, 10 nM and 800 nM, 10 nM and 700 nM, 10 nM and 600 nM, more preferably 10 nM and 500 nM, 10 nM and 400 nM, 10 nM and 300 nM, 10 nM and 200 nM, 10 nM and 100 nM, such as 10 nM and 90 nM, 10 nM and 80 nM, 10 nM and 70 nM, 10 nM and 60 nM, 10 nM and 50 nM, 10 nM and 40 nM, 10 nM and 30 nM, 10 nM and 20 nM. The term "binding" according to the invention preferably relates to a specific binding. "Specific binding" means that a binding protein (e.g. an antibody) binds stronger to a target such as an epitope for which it is specific compared to the binding to another target. A binding protein binds stronger to a first target compared to a second target if it binds to the first target with a dissociation constant ($K_d$) which is lower than the dissociation constant for the second target. Preferably the dissociation constant ($K_d$) for the target to which the binding protein binds specifically is more than 10-fold, preferably more than 20-fold, more preferably more than 50-fold, even more preferably more than 100-fold, 200-fold, 500-fold or 1000-fold lower than the dissociation constant ($K_d$) for the target to which the binding protein does not bind specifically.

For instance, the dissociation constant ($K_d$) for the target to which the binding protein binds specifically is between 10-fold and 1000-fold lower than the dissociation constant ($K_d$) for the target to which the binding protein does not bind specifically, such as between 20-fold and 1000-fold, 50-fold and 1000-fold, 100-fold and 1000-fold, 200-fold and 1000-fold, 300-fold and 1000-fold, 400-fold and 1000-fold, 500-fold and 1000-fold lower than the dissociation constant ($K_d$) for the target to which the binding protein does not bind specifically As used herein, the term "$K_d$" (measured in "mol/L", sometimes abbreviated as "M") is intended to refer to the dissociation equilibrium constant of the particular interaction between a binding protein (e.g. an antibody or fragment thereof) and a target molecule (e.g. an antigen or epitope thereof). Methods for determining binding affinities of compounds, i.e. for determining the dissociation constant $K_D$, are known to a person of ordinary skill in the art and can be selected for instance from the following methods known in the art: Surface Plasmon Resonance (SPR) based technology, Bio-layer interferometry (BLI), enzyme-linked immunosorbent assay (ELISA), flow cytometry, isothermal titration calorimetry (ITC), analytical ultracentrifugation, radioimmunoassay (RIA or IRMA) and enhanced chemiluminescence (ECL). In the context of the present application, the "$K_d$" value is determined by surface plasmon resonance spectroscopy (Biacore™) at room temperature (25° C.). For instance, surface plasmon resonance analyses were performed at 25° C. on a, typically, Biacore X100 instrument (GE Healthcare), equipped with, for example, CM5 sensor chips (GE Healthcare), wherein, for instance, HBS-EP buffer (10 mM Hepes, 0.15 M NaCl, 3 mM EDTA and 0.05% surfactant P20 at pH 7.4) was used as running buffer (GE Healthcare).

The "$IC_{50}$" value refers to the half maximal inhibitory concentration of a substance and is thus a measure of the effectiveness of a substance in inhibiting a specific biological or biochemical function. The values are typically expressed as molar concentration. The $IC_{50}$ of a drug can be determined in functional antagonistic assays by constructing a dose-response curve and examining the inhibitory effect of the examined substance at different concentrations. Alternatively, competition binding assays may be performed in order to determine the $IC_{50}$ value. Typically, inhibitory antibodies of the present invention exhibit an $IC_{50}$ value of between 50 nM-1 pM, more preferably 10 nM to 10 pM, and even more preferably between 1 nM and 50 pM, i.e. 50 nM, 10 nM, 1 nM, 900 pM, 800 pM, 700 pM, 600 pM, 500 pM, 400 pM, 300 pM, 200 pM, 100 pM, 50 pM, or 1 pM.

Cell proliferation is accepted as a reliable means of monitoring T lymphocytes activation. Proliferation of T lymphocytes is effectively monitored using CFSE Carboxyfluorescein succinimidyl ester as described in Nat. Prot. 2007; 2(9):2049-56.

Secretion of IL-2 or IFN-γ is another reliable means of monitoring T lymphocytes activation. The detection of secreted cytokine protein is by far the most widely used type of analysis. Because secreted protein is the biologically relevant moiety, its detection is the closest possible representation of what the cells are responding to. Secreted protein is typically measured by ELISA. Herein, hPBMCs ($1 \times 10^6$ cells) were cultured and stimulated with 2,5 μg/mL PHA-L or 50 ng/mL Staphylococcal enterotoxin B (SEB) for 18, 42 and 66 hours, in the absence or in the presence of the selected anti-LAG-3, anti-PD-L1 and anti-PD-1 mAbs (20 µg/mL) or of an isotype control antibody, used as negative control. Nivolumab was tested as a positive control in parallel assays, in the same conditions. The concentrations of IL-2 or IFNγ in cell culture supernatants were determined by ELISA assays (DuoSet ELISA, R&D Systems), compared to a standard curve according to the manufacturer's recommendations. Concentration values were reported as the mean of at least three determinations (standard deviation≤5%).

In animal studies tumor size is used to assess responses to anticancer therapy. Current standard technique for volume determination of subcutaneously xenografted tumors in vivo is by external caliper where tumor volume is calculated by use of the modified ellipsoid formula ½(Length×Width$^2$).

The term "compete" when used in the context of antigen binding proteins that compete for the same epitope means competition between antigen binding proteins as determined by an assay in which the antigen binding protein (e.g., antibody or immunologically functional fragment thereof) being tested prevents or inhibits (e.g., reduces) specific binding of a reference antigen binding protein (e.g., a ligand, or a reference antibody) to a common antigen (e.g., PD-1, PD-L1 and/or LAG-3 or a fragment thereof). Numerous types of competitive binding assays can be used to determine if one antigen binding protein competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using I-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabeled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Usually, when a competing antigen binding protein is present in excess, it will inhibit (e.g., reduce) specific binding of a reference antigen binding protein to PD-1, PD-L1 and/or LAG-3 or an extracellular fragment thereof by at least about 40-45%, 45-50%, 50-55%, 55-60%, 60-65%, 65-70% or 70-75%, such as about 75% or more. In some instances, binding is inhibited by at least about 80-85%, 85-90%, 90-95% or 95-97%, such as about 97% or more.

An "epitope", also known as antigenic determinant, is the part of a macromolecule that is recognized by the immune system, specifically by antibodies, B cells, or T cells. As used herein, an "epitope" is the part of a macromolecule capable of binding to a binding protein (e.g. an antibody or antigen-binding fragment thereof) as described herein. In this context, the term "binding" preferably relates to a specific binding. Epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents.

As used herein, a "conformational epitope" refers to an epitope of a linear macromolecule (e.g. a polypeptide) that is formed by the three-dimensional structure of said macromolecule. In the context of the present application, a "conformational epitope" is a "discontinuous epitope", i.e. the conformational epitope on the macromolecule (e.g. a polypeptide) which is formed from at least two separate regions in the primary sequence of the macromolecule (e.g. the amino acid sequence of a polypeptide). In other words, an epitope is considered to be a "conformational epitope" in the context of the present invention, if the epitope consists of at least two separate regions in the primary sequence to which a binding protein of the invention (e.g. an antibody or an antigen-binding fragment thereof) binds simultaneously, wherein these at least two separate regions are interrupted by one more regions in the primary sequence to which a binding protein of the invention does not bind. Preferably, such a "conformational epitope" is present on a polypeptide, and the two separate regions in the primary sequence are two separate amino acid sequences to which a binding protein of the invention (e.g. an antibody or an antigen-binding fragment thereof) binds, wherein these at least two separate amino acid sequences are interrupted by one more amino acid sequences in the primary sequence to which a binding protein of the invention does not bind. Preferably, the interrupting amino acid sequence is a contiguous amino acid sequence comprising two or more amino acids to which the binding protein does not bind. The at least two separate amino acid sequences to which a binding protein of the invention binds are not particularly limited with regard to their length. Such a separate amino acid sequence may consists of only one amino acid as long as the total number of amino acids within said at least two separate amino acid sequences is sufficiently large to effect specific binding between the binding protein and the conformational epitope.

A "paratope" is the part of an antibody that recognizes the epitope. In the context of the present invention, a "paratope" is the part of a binding protein (e.g. an antibody or antigen-binding fragment thereof) as described herein that recognizes the epitope.

The term "antibody" typically refers to a glycoprotein comprising at least two heavy (H) chains and two light (L) chains inter-connected by disulfide bonds, or an antigen-binding portion thereof. The term "antibody" also includes all recombinant forms of antibodies, in particular of the antibodies described herein, e.g. antibodies expressed in prokaryotes, unglycosylated antibodies, and any antigen-binding antibody fragments and derivatives as described below. Each heavy chain is comprised of a heavy chain variable region (abbreviated herein as VH or $V_H$) and a heavy chain constant region. Each light chain is comprised of a light chain variable region (abbreviated herein as VL or $V_L$) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody (or simply "binding portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is a binding-domain immunoglobulin fusion protein comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies. Further examples of "antigen-binding fragments" are so-called microantibodies, which are derived from single CDRs. For example, Heap et al., 2005, describe a 17 amino acid residue microantibody derived from the heavy chain CDR3 of an antibody directed against the gp120 envelope glycoprotein of HIV-1. Other examples include small antibody mimetics comprising two or more CDR regions that are fused to each other, preferably by cognate framework regions. Such a small antibody mimetic comprising $V_H$ CDR1 and $V_L$ CDR3 linked by the cognate $V_H$ FR2 has been described by Qiu et al., 2007.

The immunoglobulin molecules of the invention can be of any type (e.g., IgG, IgE, IgM, IgD, IgA and IgY), class (e.g., IgG1, IgG2, preferably IgG2a and IgG2b, IgG3, IgG4, IgA1 and IgA2) or subclass of immunoglobulin molecule.

Antibodies and antigen-binding fragments thereof usable in the invention may be from any animal origin including birds and mammals. Preferably, the antibodies or fragments are from human, chimpanzee, rodent (e.g. mouse, rat, guinea pig, or rabbit), chicken, turkey, pig, sheep, goat, camel, cow, horse, donkey, cat, or dog origin. It is particularly preferred that the antibodies are of human or murine origin. Antibodies of the invention also include chimeric molecules in which an antibody constant region derived from one species, preferably human, is combined with the antigen binding site derived from another species, e.g. mouse. Moreover antibodies of the invention include humanized molecules in which the antigen binding sites of an antibody derived from a non-human species (e.g. from mouse) are combined with constant and framework regions of human origin.

As exemplified herein, antibodies of the invention can be obtained directly from hybridomas which express the antibody, or can be cloned and recombinantly expressed in a host cell (e.g., a CHO cell, or a lymphocytic cell). Further examples of host cells are microorganisms, such as E. coli, and fungi, such as yeast. Alternatively, they can be produced recombinantly in a transgenic non-human animal or plant.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human is less likely to elicit an immune response from a human subject when the antibodies are injected than would the constant region from a non-human source. However, the definition is not limited to this particular example.

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen-binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

Different methods for humanizing antibodies are known to the skilled person, as reviewed by Almagro & Fransson, 2008, the content of which is herein incorporated by reference in its entirety. The review article by Almagro & Fransson is briefly summarized in the following. Almagro & Fransson distinguish between rational approaches and empirical approaches. Rational approaches are characterized by generating few variants of the engineered antibody and assessing their binding or any other property of interest. If the designed variants do not produce the expected results, a new cycle of design and binding assessment is initiated. Rational approaches include CDR grafting, Resurfacing, Superhumanization, and Human String Content Optimization. In contrast, empirical approaches are based on the generation of large libraries of humanized variants and selection of the best clones using enrichment technologies or high-throughput screening. Accordingly, empirical approaches are dependent on a reliable selection and/or screening system that is able to search through a vast space of antibody variants. In vitro display technologies, such as phage display and ribosome display fulfill these requirements and are well-known to the skilled person. Empirical approaches include FR libraries, Guided selection, Framework-shuffling, and Humaneering.

CDR Grafting

A CDR grafting protocol typically comprises three decision-making points: (1) definition of regions determining the specificity of the donor antibody, i.e. the target for grafting, (2) identification of a source of human sequences to be utilized as FR donors, and (3) selection of residues outside of the region defining the specificity, i.e. determining amino acid positions that are targets for back mutation to restore or improve the affinity of the humanized antibody.

(1) Regions Determining the Antibody Specificity

The experimental structure of the non-human antibody in complex with the antigen provides a detailed map of residues in contact with the antigen and therefore those responsible for determining its specificity. The structural information can be complemented with alanine scanning mutagenesis and/or combinatorial mutagenesis to identify the residues contributing most to the binding energy or to the functional paratope. Since the functional paratope is a subset of the residues in contact, grafting only the functional paratope would reduce the number of non-human residues in the humanized product. However, only in rare cases are the experimental structure of the antigen-antibody complex and/or the functional paratope available at the beginning of a humanization protocol. In absence of a precise definition of residues responsible for a given antibody specificity, CDRs are often employed as regions defining the specificity. It is also possible to use a combination of CDR and HV loop as targets for grafting. To reduce the number of residues to be grafted on the human FRs, SDR grafting has been described, i.e. the grafting of specificity-determining residues (SDRs).

(2) Source of Human FRs

The second step in a typical CDR grafting protocol is to identify human FR donors. Initial works utilized FRs of human antibodies of known structure, regardless of their homology to the non-human antibody. This approach is known as "Fixed FR method". Later works used human sequences having the highest homology to the non-human antibody. This approach has been termed "Best Fit". While "best fit" strategies tend to result in antibodies with higher affinity, other parameters such as low immunogenicity and production yields have to be taken into account, too, when choosing an FR for humanization. Thus, combinations of "best fit" and "fixed FR" are also possible. For example, the $V_L$ part can be humanized according to the fixed FR method and the $V_H$ part can be humanized according to the best fit method, or vice versa.

Two sources of human sequences have been utilized: mature and germline sequences. Mature sequences, which are products of immune responses, carry somatic mutations generated by random processes and are not under the species selection, resulting in potential immunogenic residues. Thus, to avoid immunogenic residues, human germline genes have increasingly been utilized as source of FR donors. Nucleotide sequences of human germline FRs are disclosed e.g. in Appendices A and B of the article by Dall'Acqua et al, 2005. Furthermore, germline gene based antibodies tend to be more flexible as compared to mature antibodies. This higher flexibility is thought to better accommodate diverse CDRs with fewer or no back mutations into the FR to restore the affinity of the humanized antibody.

(3) Back Mutations to Restore or Enhance Affinity

Commonly, affinity decreases after CDR grafting as a consequence of incompatibilities between non-human CDRs and human FRs. Therefore, the third step in a typical CDR grafting protocol is to define mutations that would restore or prevent affinity losses. Back mutations have to be carefully designed based on the structure or a model of the humanized antibody and tested experimentally. A web site for automated antibody modeling called WAM can be found at antibody.bath. Software for protein structure modeling can be downloaded at the sites salilab.org (Modeller) and spdbv.vital (Swiss Pdb Viewer).

Resurfacing

Resurfacing is similar to CDR grafting and shares the first two decision-making points. In contrast to CDR grafting, resurfacing retains the non-exposed residues of the non-human antibody. Only surface residues in the non-human antibody are changed to human residues.

Superhumanization

While CDR grafting relies on the FR comparison between the non-human and the humans sequences, superhumanization is based on a CDR comparison so that FR homology is irrelevant. The approach includes a comparison of the non-human sequence with the functional human germline gene repertoire. Those genes encoding the same or closely related canonical structures to the murine sequences are then selected. Next, within the genes sharing the canonical structures with the non-human antibody, those with highest homology within the CDRs are chosen as FR donors. Finally, the non-human CDRs are grafted onto these FRs.

Human String Content Optimization

This approach is based on a metric of antibody "humanness", termed Human String Content (HSC). In short, this approach compares the mouse sequence with the repertoire of human germline genes. Differences are scored as HSC. The target sequence is the humanized by maximizing its HSC rather than using a global identity measure to generate multiple diverse humanized variants.

Framework Libraries (Abbreviated: FR Libraries)

In the FR library approach, a collection of residue variants are introduced at specific positions in the FR followed by panning of the library to select the FR that best supports the grafted CDR. Thus, this approach resembles CDR grafting but instead of creating a few back mutations in the FR, a combinatorial library of typically more than 100 mutational variants is constructed.

Guided Selection

This approach includes combining the $V_H$ or $V_L$ domain of a given non-human antibody specific for a particular antigen with a human $V_H$ and $V_L$ library. Subsequently, specific human V domains are selected against the antigen of interest. For example, a non-human antibody can be humanized by first combining the non-human Vu with a library of human light chains. The library is then selected against the target antigen by phage display and the selected $V_L$ is cloned into a library of human $V_H$ chains and selected against the target antigen. It is also possible to start with combining the non-human $V_L$ with a library of human heavy chains. The library is then selected against the target antigen by phage display and the selected $V_H$ is cloned into a library of human $V_L$ chains and selected against the target antigen. As a result, a fully human antibody with similar affinity as the non-human antibody can be isolated. To avoid the occurrence of an epitope drift, it is possible to implement a so-called inhibition ELISA, which allows for the selection of clones recognizing the same epitope as the parent antibody. Alternatively, CDR retention can be applied to avoid an epitope drift. In CDR retention, one or more non-human CDRs are retained, preferably the heavy chain CDR3, since this CDR is at the center of the antigen binding site.

Framework Shuffling (Abbreviated: FR Shuffling)

In the FR shuffling approach, whole FRs are combined with the non-human CDRs. Using FR shuffling, Dall'Acqua and co-workers humanized a murine antibody. All six CDRs of the murine antibody were cloned into a library containing all human germline gene FRs (Dall'Acqua et al., 2005). The libraries were screened for binding in a two-step selection process, first humanizing $V_L$, followed by $V_H$. In a later study, a one-step FR shuffling process was successfully used (Damschroder et al., 2007). Oligonucleotide sequences encoding all known human germline light chain (K) frameworks are disclosed in Dall'Acqua et al., 2005, as Appendix A. Oligonucleotide sequences encoding all known human germline heavy chain frameworks are disclosed in Dall'Acqua et al., 2005, as Appendix B.

Humaneering

Humaneering allows for isolation of antibodies that are 91-96% homologous to human germline gene antibodies. The method is based on experimental identification of essential minimum specificity determinants (MSDs) and on sequential replacement of non-human fragments into libraries of human FRs and assessment of binding. It begins with regions of the CDR3 of non-human $V_H$ and $V_L$ chains and progressively replaces other regions of the non-human antibody into the human FRs, including the CDR1 and CDR2 of both $V_H$ and $V_L$.

The methods for humanizing antibodies explained above are preferred when generating humanized antibodies that specifically bind to the conformational epitopes described herein. Nevertheless, the present invention is not limited to the above-mentioned methods for humanizing antibodies.

Some of the aforementioned humanization methods can be performed without information about the FR sequences in the donor antibody, namely the "Fixed FR Method" (a variant of CDR-grafting), Superhumanization, Framework-shuffling, and Humaneering. Variations of the "fixed FR method" were successfully carried out by Qin et al., 2007 and Chang et al., 2007. In particular, Qin et al. constructed an antibody fragment comprising a human heavy chain variable region in which the three CDR regions were replaced by antigenic peptides, which were derived from the CDR sequences of a murine antibody. Chang et al. continued these experiments and constructed a scFv fragment, in which all CDRs from the $V_H$ part and CDR3 from the $V_L$ part were replaced by antigenic peptides, which were derived from the CDR sequences of a murine antibody.

As used herein, "human antibodies" include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). Human antibodies of the invention include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

The term "monoclonal antibody" as used herein refers to a preparation of antibody molecules of single molecular composition. A monoclonal antibody displays a single binding specificity and affinity for a particular epitope. In one embodiment, the monoclonal antibodies are produced by a hybridoma which includes a B cell obtained from a non-human animal, e.g. mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g. from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "transfectoma", as used herein, includes recombinant eukaryotic host cells expressing an antibody, such as CHO cells, NS/0 cells, HEK293 cells, HEK293T cells, plant cells, or fungi, including yeast cells.

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

Thus, "antibodies and antigen-binding fragments thereof" suitable for use in the present invention include, but are not limited to, polyclonal, monoclonal, monovalent, bispecific, heteroconjugate, multispecific, recombinant, heterologous, heterohybrid, chimeric, humanized (in particular CDR-grafted), deimmunized, or human antibodies, Fab fragments, Fab' fragments, F(ab')$_2$ fragments, fragments produced by a Fab expression library, Fd, Fv, disulfide-linked Fvs (dsFv), single chain antibodies (e.g. scFv), diabodies or tetrabodies (Holliger P. et al. (1993) Proc. Natl. Acad. Sci. U.S.A. 90(14), 6444-6448), nanobodies (also known as single domain antibodies), anti-idiotypic (anti-Id) antibodies (including, e.g., anti-Id antibodies to antibodies of the invention), and epitope-binding fragments of any of the above.

The antibodies described herein are preferably isolated. An "isolated antibody" as used herein, is intended to refer to an antibody which is substantially free of other antibodies having different antigenic specificities.

The term "naturally occurring", as used herein, as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

As used herein, the term "nucleic acid aptamer" refers to a nucleic acid molecule that has been engineered through repeated rounds of in vitro selection or SELEX (systematic evolution of ligands by exponential enrichment) to bind to a target molecule (for a review see: Brody E.N. and Gold L. (2000), Aptamers as therapeutic and diagnostic agents. J. Biotechnol. 74(1):5-13). The nucleic acid aptamer may be a DNA or RNA molecule. The aptamers may contain modifications, e.g. modified nucleotides such as 2'-fluorine-substituted pyrimidines.

As used herein, the term "antibody-like protein" refers to a protein that has been engineered (e.g. by mutagenesis of loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop typically consists of 10 to 20 amino acids. The scaffold protein may be any protein having good solubility properties. Preferably, the scaffold protein is a small globular protein. Antibody-like proteins include without limitation affibodies, anticalins, and designed ankyrin repeat proteins (for review see: Binz H. K. et al. (2005) Engineering novel binding proteins from nonimmunoglobulin domains. Nat. Biotechnol. 23(10):1257-1268). Antibody-like proteins can be derived from large libraries of mutants, e.g. be panned from large phage display libraries and can be isolated in analogy to regular antibodies. Also, antibody-like binding proteins can be obtained by combinatorial mutagenesis of surface-exposed residues in globular proteins. Antibody-like proteins are sometimes referred to as "peptide aptamers".

As used herein, a "peptidomimetic" is a small protein-like chain designed to mimic a peptide. Peptidomimetics typically arise from modification of an existing peptide in order to alter the molecule's properties. For example, they may arise from modifications to change the molecule's stability or biological activity. This can have a role in the development of drug-like compounds from existing peptides. These modifications involve changes to the peptide that will not occur naturally (such as altered backbones and the incorporation of non-natural amino acids).

The "percentage of sequences identity" is determined by comparing two optimally aligned sequences over a comparison window, wherein the portion of the sequence in the comparison window can comprise additions or deletions (i.e. gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" is used herein in the context of two or more nucleic acids or polypeptide sequences, to refer to two or more sequences or subsequences that are the same, i.e. comprise the same sequence of nucleotides or amino acids. Sequences are "substantially identical" to each other if they have a specified percentage of nucleotides or amino acid residues that are the same (e.g., at least 70%, at least 75%, at least 80, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity over a specified region), when compared and aligned for maximum correspondence over a comparison window, or designated region as measured using one of the following sequence comparison algorithms or by manual alignment and visual inspection. These definitions also refer to the complement of a test sequence. Accordingly, the term "at least 80% sequence identity" is used throughout the specification with regard to polypeptide and polynucleotide sequence comparisons. This expression preferably refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide.

The term "sequence comparison" is used herein to refer to the process wherein one sequence acts as a reference sequence, to which test sequences are compared. When using a sequence comparison algorithm, test and reference sequences are entered into a computer, if necessary subsequence coordinates are designated, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters. In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by SEQ ID, if not specifically indicated otherwise.

In a sequence alignment, the term "comparison window" refers to those stretches of contiguous positions of a sequence which are compared to a reference stretch of contiguous positions of a sequence having the same number of positions. The number of contiguous positions selected may range from 4 to 1000, i.e. may comprise 4, 5, 10, 20, 30, 40, 50, 60, 70, 80, 90, 100, 150, 200, 250, 300, 350, 400, 450, 500, 550, 600, 650, 700, 750, 800, 850, 900, 950, or 1000 contiguous positions. Typically, the number of contiguous positions ranges from about 20 to 800 contiguous positions, from about 20 to 600 contiguous positions, from about 50 to 400 contiguous positions, from about 50 to about 200 contiguous positions, from about 100 to about 150 contiguous positions.

Methods of alignment of sequences for comparison are well known in the art. Optimal alignment of sequences for comparison can be conducted, for example, by the local homology algorithm of Smith and Waterman (Adv. Appl. Math. 2:482, 1970), by the homology alignment algorithm of Needleman and Wunsch (J. Mol. Biol. 48:443, 1970), by the search for similarity method of Pearson and Lipman (Proc. Natl. Acad. Sci. USA 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)). Algorithms suitable for determining percent sequence identity and sequence similarity are the BLAST and BLAST 2.0 algorithms, which are described in Altschul et al. (Nuc. Acids Res. 25:3389-402, 1977), and Altschul et al. (J. Mol. Biol. 215:403-10, 1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands. The BLAST algorithm also performs a statistical analysis of the similarity between two sequences (see, e.g., Karlin and Altschul, Proc. Natl. Acad. Sci. USA 90:5873-87, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

"Conservative substitutions" may be made, for instance, on the basis of similarity in polarity, charge, size, solubility, hydrophobicity, hydrophilicity, and/or the amphipathic nature of the amino acid residues involved. Amino acids can be grouped into the following six standard amino acid groups:

(1) hydrophobic: Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro; and
(6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices. Some preferred conservative substitutions within the above six groups are exchanges within the following sub-groups: (i) Ala, Val, Leu and Ile; (ii) Ser and Thr; (ii) Asn and Gln; (iv) Lys and Arg; and (v) Tyr and Phe. Given the known genetic code, and recombinant and synthetic DNA techniques, the skilled scientist readily can construct DNAs encoding the conservative amino acid variants.

As used herein, "non-conservative substitutions" or "non-conservative amino acid exchanges" are defined as exchanges of an amino acid by another amino acid listed in a different group of the six standard amino acid groups (1) to (6) shown above.

The term "nucleic acid" and "nucleic acid molecule" are used synonymously herein and are understood as single or double-stranded oligo- or polymers of deoxyribonucleotide or ribonucleotide bases or both. Nucleotide monomers are composed of a nucleobase, a five-carbon sugar (such as but not limited to ribose or 2'-deoxyribose), and one to three phosphate groups. Typically, a nucleic acid is formed through phosphodiester bonds between the individual nucleotide monomers, In the context of the present invention, the term nucleic acid includes but is not limited to ribonucleic acid (RNA) and deoxyribonucleic acid (DNA) molecules but also includes synthetic forms of nucleic acids comprising other linkages (e.g., peptide nucleic acids as described in Nielsen et al. (Science 254:1497-1500, 1991). Typically, nucleic acids are single- or double-stranded molecules and are composed of naturally occurring nucleotides. The depiction of a single strand of a nucleic acid also defines (at least partially) the sequence of the complementary strand. The nucleic acid may be single or double stranded, or may contain portions of both double and single stranded sequences. Exemplified, double-stranded nucleic acid molecules can have 3' or 5' overhangs and as such are not required or assumed to be completely double-stranded over their entire length. The nucleic acid may be obtained by biological, biochemical or chemical synthesis methods or any of the methods known in the art, including but not limited to methods of amplification, and reverse transcription of RNA. The term nucleic acid comprises chromosomes or chromosomal segments, vectors (e.g., expression vectors), expression cassettes, naked DNA or RNA polymer, primers, probes, cDNA, genomic DNA, recombinant DNA, CRNA, mRNA, tRNA, microRNA (miRNA) or small interfering RNA (siRNA). A nucleic acid can be, e.g., single-stranded, double-stranded, or triple-stranded and is not limited to any particular length. Unless otherwise indicated, a particular nucleic acid sequence comprises or encodes complementary sequences, in addition to any sequence explicitly indicated.

Nucleic acids may be degraded by endonucleases or exonucleases, in particular by DNases and RNases which can be found in the cell. It may, therefore, be advantageous to modify the nucleic acids of the invention in order to stabilize them against degradation, thereby ensuring that a high concentration of the nucleic acid is maintained in the cell over a long period of time. Typically, such stabilization can be obtained by introducing one or more internucleotide phosphorus groups or by introducing one or more non-phosphorus internucleotides. Accordingly, nucleic acids can be composed of non-naturally occurring nucleotides and/or modifications to naturally occurring nucleotides, and/or changes to the backbone of the molecule. Modified internucleotide phosphate radicals and/or non-phosphorus bridges in a nucleic acid include but are not limited to methyl phosphonate, phosphorothioate, phosphoramidate, phosphorodithioate and/or phosphate esters, whereas non-phosphorus internucleotide analogues include but are not limited to, siloxane bridges, carbonate bridges, carboxymethyl esters, acetamidate bridges and/or thioether bridges. Further examples of nucleotide modifications include but are not limited to: phosphorylation of 5' or 3' nucleotides to allow for ligation or prevention of exonuclease degradation/ polymerase extension, respectively; amino, thiol, alkyne, or biotinyl modifications for covalent and near covalent attachments; fluorphores and quenchers; and modified bases such as deoxyInosine (dI), 5-Bromo-deoxyuridine (5-Bromo-dU), deoxyUridine, 2-Aminopurine, 2,6-Diaminopurine, inverted dT, inverted Dideoxy-T, dideoxyCytidine (ddC 5-Methyl deoxyCytidine (5-Methyl dC), locked nucleic acids (LNA's), 5-Nitroindole, Iso-dC and -dG bases, 2'-O-Methyl RNA bases, Hydroxmethyl dC, 5-hydroxybutynl-2'-deoxyuridine, 8-aza-7-deazaguanosineand Fluorine Modified Bases. Thus, the nucleic acid can also be an artificial nucleic acid which includes but is not limited to polyamide or peptide nucleic acid (PNA), morpholino and locked nucleic acid (LNA), as well as glycol nucleic acid (GNA) and threose nucleic acid (TNA).

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

The term "polynucleotide", when used in the context of the present invention, refers to a nucleic acid of more than about 50 nucleotides in length, e.g. 51 or more nucleotides in length.

Polypeptides of the invention are prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (Meth. Enzymol. 68:90-99, 1979); the phosphodiester method of Brown et al. (Meth. Enzymol. 68:109-151, 1979); the diethylphosphoramidite method of Beaucage et al. (Tetrahedron Lett. 22:1859-1862, 1981); the triester method of Matteucci et al. (J. Am. Chem. Soc. 103:3185-3191, 1981); automated synthesis methods; or the solid support method of U.S. Pat. No. 4,458,066, or other methods known to those skilled in the art.

As used herein, the term "vector" refers to a protein or a polynucleotide or a mixture thereof which is capable of being introduced or of introducing proteins and/or nucleic acids comprised therein into a cell. Examples of vectors include but are not limited to plasmids, cosmids, phages, viruses or artificial chromosomes. In particular, a vector is used to transport a gene product of interest, such as e.g. foreign or heterologous DNA into a suitable host cell. Vectors may contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Vectors may further encompass "expression control sequences" that regulate the expression of the gene of interest. Typically, expression control sequences are polypeptides or polynucleotides such as but not limited to promoters, enhancers, silencers, insulators, or repressors. In a vector comprising more than one polynucleotide encoding for one or more gene products of interest, the expression may be controlled together or separately by one or more expression control sequences. More specifically, each polynucleotide comprised on the vector may be control by a separate expression control sequence or all polynucleotides comprised on the vector may be controlled by a single expression control sequence. Polynucleotides comprised on a single vector controlled by a single expression control sequence may form an open reading frame. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

The term "host cell" refers to a cell that harbors a vector (e.g. a plasmid or virus). Such host cell may either be a prokaryotic (e.g. a bacterial cell) or a eukaryotic cell (e.g. a fungal, plant or animal cell). Host cells include both single-cellular prokaryote and eukaryote organisms (e.g., bacteria, yeast, and actinomycetes) as well as single cells from higher order plants or animals when being grown in cell culture. "Recombinant host cell", as used herein, refers to a host cell that comprises a polynucleotide that codes for a polypeptide fragment of interest, i.e., the fragment of the viral PA subunit or variants thereof according to the invention. This polynucleotide may be found inside the host cell (i) freely dispersed as such, (ii) incorporated in a recombinant vector, or (iii) integrated into the host cell genome or mitochondrial DNA. The recombinant cell can be used for expression of a polynucleotide of interest or for amplification of the polynucleotide or the recombinant vector of the invention. The term "recombinant host cell" includes the progeny of the original cell which has been transformed, transfected, or infected with the polynucleotide or the recombinant vector of the invention. A recombinant host cell may be a bacterial cell such as an *E. coli* cell, a yeast cell such as *Saccharomyces cerevisiae* or *Pichia pastoris*, a plant cell, an insect cell such as SF9 or High Five cells, or a mammalian cell. Preferred examples of mammalian cells are Chinese hamster ovary (CHO) cells, green African monkey kidney (COS) cells, human embryonic kidney (HEK293) cells, HELA cells, and the like.

The term "active agent" as used herein, refers to any therapeutic activity an agent may exhibit.

"Pharmaceutically acceptable" means approved by a regulatory agency of the Federal or a state government or listed in the U.S. Pharmacopeia or other generally recognized pharmacopeia for use in animals, and more particularly in humans.

The term "carrier", as used herein, refers to a diluent, adjuvant, excipient, or vehicle with which the therapeutic agent is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

Generally known and practiced methods in the fields of molecular biology, cell biology, protein chemistry and antibody techniques are fully described in the continuously updated publications "Molecular Cloning: A Laboratory Manual", (Sambrook et al., Cold Spring Harbor); Current Protocols in Molecular Biology (F. M. Ausubel et al. Eds., Wiley & Sons); Current Protocols in Protein Science (J. E. Colligan et al. eds., Wiley & Sons); Current Protocols in Cell Biology (J. S. Bonifacino et al., Wiley & Sons) and Current Protocols in Immunology (J. E. Colligan et al., Eds., Wiley & Sons). Known techniques relating to cell culture and media are described in "Large Scale Mammalian Cell Culture (Hu et al., Curr. Opin., Biotechnol. 8: 148, 1997); "Serum free Media" (K. Kitano, Biotechnol. 17:73, 1991); and "Suspension Culture of Mammalian Cells" (Birch et al. Bioprocess Technol. 19: 251, 1990).

EMBODIMENTS

In the following different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In a first aspect, the present invention provides an antagonistic antigen binding protein that specifically binds to PD-1, wherein said antigen binding protein competes for binding to PD-1 with an antibody
 (i) comprising a heavy chain variable region of the amino acid sequence in SEQ ID NO: 2; and a light chain variable region of the amino acid sequence in SEQ ID NO: 3; or
 (ii) comprising a heavy chain variable region of the amino acid sequence in SEQ ID NO: 11; and a light chain variable region of the amino acid sequence in SEQ ID NO: 12.

Preferably, the present invention provides an antagonistic antigen binding protein that specifically binds to PD-1, wherein said antigen binding protein competes for binding to PD-1 with an antibody comprising a heavy chain variable region of the amino acid sequence in SEQ ID NO: 2; and a light chain variable region of the amino acid sequence in SEQ ID NO: 3.

In a preferred embodiment of the first aspect, the antagonistic antigen binding protein that specifically binds to PD-1 is an antibody, an antibody-like protein or a fragment thereof. Preferably, the antibody is selected from the group consisting of a human antibody, a humanized antibody, chimeric antibody, a monoclonal antibody, a multispecific antibody, a recombinant antibody, an antigen-binding antibody fragment, a single chain antibody, a single chain variable fragment antibody, a diabody, a Fab fragment, an F(ab)2 fragment, an antibody mimetic, an IgG1 antibody, an IgG2 antibody, an IgG3 antibody, and an IgG4 antibody.

In a further preferred embodiment of the first aspect, the antagonistic antigen binding protein that specifically binds to PD-1 binds to PD-1 with a $K_d$ of less than 100 nM, of less than 50 nM, of less than 10 nM, of less than 1 nM, of less than 100 pM, of less than 10 pM, or of less than 5 pM. For instance, the antagonistic antigen binding protein that specifically binds to PD-1 binds to PD-1 with a $K_d$ between 5 pM and 100 nM, 5 pM and 50 nM, 5 PM and 10 nM, 5 pM and 1 nM, 5 pM and 100 pM, such as between 5 pM and 10 pM.

In a further preferred embodiment of the first aspect, the antagonistic antigen binding protein that specifically binds to PD-1 can block the binding of a ligand to PD-1 with an IC50 of less than 10 nM, less than 1 nM, or less than 200 pM. For instance, the antagonistic antigen binding protein that specifically binds to PD-1 can block the binding of a ligand to PD-1 with an IC50 between 200 pM and 10 nM, such as between 200 pM and 1nM.

In a further preferred embodiment of the first aspect, the antagonistic antigen binding protein that specifically binds to PD-1 stimulates T cell proliferation.

In a further preferred embodiment of the first aspect, the antagonistic antigen binding protein that specifically binds to PD-1 induces the proliferation of lymphocytes.

In a further preferred embodiment of the first aspect, the antagonistic antigen binding protein that specifically binds to PD-1 induces secretion of IL-2 and/or IFNγ.

In a further preferred embodiment of the first aspect, the antagonistic antigen binding protein that specifically binds to PD-1 reduces tumor volume by at least 50%, at least 60%, at least 70%, at least 80% or at least 90% compared to baseline value.

In a second aspect, the present invention provides an antagonistic antigen binding protein that specifically binds to PD-L1, wherein said antigen binding protein competes for binding to PD-L1 with an antibody
 (i) comprising a heavy chain variable region of the amino acid sequence in SEQ ID NO: 20; and a light chain variable region of the amino acid sequence in SEQ ID NO: 21; or
 (ii) comprising a heavy chain variable region of the amino acid sequence in SEQ ID NO: 29; and a light chain variable region of the amino acid sequence in SEQ ID NO: 30; or
 (iii) comprising a heavy chain variable region of the amino acid sequence in SEQ ID NO: 83; and a light chain variable region of the amino acid sequence in SEQ ID NO: 84; or
 (iv) comprising a heavy chain variable region of the amino acid sequence in SEQ ID NO: 92; and a light chain variable region of the amino acid sequence in SEQ ID NO: 93; or
 (v) comprising a heavy chain variable region of the amino acid sequence in SEQ ID NO: 101; and a light chain variable region of the amino acid sequence in SEQ ID NO: 102.

Preferably, the present invention provides an antagonistic antigen binding protein that specifically binds to PD-L1, wherein said antigen binding protein competes for binding to PD-L1 with an antibody comprising a heavy chain variable region of the amino acid sequence in SEQ ID NO: 29; and a light chain variable region of the amino acid sequence in SEQ ID NO: 30.

In a preferred embodiment of the second aspect, the antagonistic antigen binding protein that specifically binds to PD-L1 is an antibody, an antibody-like protein or a fragment thereof. Preferably, the antibody is selected from the group consisting of a human antibody, a humanized antibody, chimeric antibody, a monoclonal antibody, a multispecific antibody, a recombinant antibody, an antigen-binding antibody fragment, a single chain antibody, a single chain variable fragment antibody, a diabody, a Fab fragment, an F(ab)2 fragment, an antibody mimetic, an IgG1 antibody, an IgG2 antibody, an IgG3 antibody, and an IgG4 antibody.

In a further preferred embodiment of the second aspect, the antagonistic antigen binding protein that specifically binds to PD-L1 binds to PD-L1 with a $K_d$ of less than 100 nM, of less than 50 nM, of less than 10 nM, of less than 1 nM, of less than 100 pM, of less than 10 pM, or of less than 5 pM. For instance, the antagonistic antigen binding protein that specifically binds to PD-L1 binds to PD-L1 with a $K_d$ between 5 pM and 100 nM, 5 PM and 50 nM, 5 PM and 10 nM, 5 pM and 1 nM, 5 pM and 100 pM, such as between 5 pM and 10 pM.

In a further preferred embodiment of the second aspect, the antagonistic antigen binding protein that specifically binds to PD-L1 can block the binding of a ligand to PD-L1 with an IC50 of less than 10 nM, less than 1 nM, or less than 200 pM.

For instance, the antagonistic antigen binding protein that specifically binds to PD-L1 can block the binding of a ligand to PD-L1 with an IC50 between 200 pM and 10 nM, such as between 200 pM and 1 nM.

In a further preferred embodiment of the second aspect, the antagonistic antigen binding protein that specifically binds to PD-L1 stimulates T cell proliferation.

In a further preferred embodiment of the second aspect, the antagonistic antigen binding protein that specifically binds to PD-L1 induces the proliferation of lymphocytes.

In a further preferred embodiment of the second aspect, the antagonistic antigen binding protein that specifically binds to PD-L1 induces secretion of IL-2 and/or IFNγ.

In a further preferred embodiment of the second aspect, the antagonistic antigen binding protein that specifically binds to PD-L1 reduces tumor volume by at least 50%, at least 60%, at least 70%, at least 80% or at least 90% compared to baseline value.

In a third aspect, the present invention relates to an antagonistic antigen binding protein that specifically binds to LAG-3, wherein said antigen binding protein competes for binding to LAG-3 with an antibody
(i) comprising a heavy chain variable region of the amino acid sequence in SEQ ID NO: 38; and a light chain variable region of the amino acid sequence in SEQ ID NO: 39;
(ii) comprising a heavy chain variable region of the amino acid sequence in SEQ ID NO: 47; and a light chain variable region of the amino acid sequence in SEQ ID NO: 48;
(iii) comprising a heavy chain variable region of the amino acid sequence in SEQ ID NO: 56; and a light chain variable region of the amino acid sequence in SEQ ID NO: 57;
(iv) comprising a heavy chain variable region of the amino acid sequence in SEQ ID NO: 65; and a light chain variable region of the amino acid sequence in SEQ ID NO: 66; or
(v) comprising a heavy chain variable region of the amino acid sequence in SEQ ID NO: 74; and a light chain variable region of the amino acid sequence in SEQ ID NO: 75.

Preferably, the present invention provides an antagonistic antigen binding protein that specifically binds to LAG-3, wherein said antigen binding protein competes for binding to LAG-3 with an antibody comprising a heavy chain variable region of the amino acid sequence in SEQ ID NO: 38; and a light chain variable region of the amino acid sequence in SEQ ID NO: 39.

In another preferred embodiment, the present invention provides an antagonistic antigen binding protein that specifically binds to LAG-3, wherein said antigen binding protein competes for binding to LAG-3 with an antibody comprising a heavy chain variable region of the amino acid sequence in SEQ ID NO: 47; and a light chain variable region of the amino acid sequence in SEQ ID NO: 48.

In a preferred embodiment of the third aspect, the antagonistic antigen binding protein that specifically binds to LAG-3 is an antibody, an antibody-like protein or a fragment thereof. Preferably, the antibody is selected from the group consisting of a human antibody, a humanized antibody, chimeric antibody, a monoclonal antibody, a multispecific antibody, a recombinant antibody, an antigen-binding antibody fragment, a single chain antibody, a single chain variable fragment antibody, a diabody, a Fab fragment, an F(ab)2 fragment, an antibody mimetic, an IgG1 antibody, an IgG2 antibody, an IgG3 antibody, and an IgG4 antibody.

In a further preferred embodiment of the third aspect, the antagonistic antigen binding protein that specifically binds to LAG-3 binds to LAG-3 with a $K_d$ of less than 100 nM, of less than 50 nM, of less than 10 nM, of less than 1 nM, of less than 100 pM, of less than 10 pM, or of less than 5 pM. For instance, the antagonistic antigen binding protein that specifically binds to LAG-3 binds to LAG-3 with a $K_d$ between 5 pM and 100 nM, 5 PM and 50 nM, 5 PM and 10 nM, 5 pM and 1 nM, 5 pM and 100 pM, such as between 5 pM and 10 pM.

In a further preferred embodiment of the third aspect, the antagonistic antigen binding protein that specifically binds to LAG-3 can block the binding of a ligand to LAG-3 with an IC50 of less than 10 nM, less than 1 nM, or less than 200 pM. For instance, the antagonistic antigen binding protein that specifically binds to LAG-3 can block the binding of a ligand to LAG-3 with an IC50 between 200 pM and 10 nM, such as between 200 pM and InM.

In a further preferred embodiment of the third aspect, the antagonistic antigen binding protein that specifically binds to LAG-3 stimulates T cell proliferation.

In a further preferred embodiment of the third aspect, the antagonistic antigen binding protein that specifically binds to LAG-3 induces the proliferation of lymphocytes.

In a further preferred embodiment of the third aspect, the antagonistic antigen binding protein that specifically binds to LAG-3 induces secretion of IL-2 and/or IFNγ.

In a further preferred embodiment of the third aspect, the antagonistic antigen binding protein that specifically binds to LAG-3reduces tumor volume by at least 50%, at least 60%, at least 70%, at least 80% or at least 90% compared to baseline value.

In a fourth aspect, the present invention relates to an antagonistic antigen binding protein that specifically binds to PD-1, wherein said antigen binding protein comprises either
(i) a combination of a light chain variable domain and a heavy chain variable domain selected from the group of combinations consisting of:
a light chain variable domain having a sequence with at least 90% identity to SEQ ID NO: 3 and
a heavy chain variable domain having a sequence with at least 90% identity to SEQ ID NO: 2;
a light chain variable domain having a sequence with at least 90% identity to SEQ ID NO: 12 and
a heavy chain variable domain having a sequence with at least 90% identity to SEQ ID NO: 11;
(ii) a combination of a complementarity determining region 3 of the heavy chain (CDRH3) and a complementarity determining region 3 of the light chain (CDRL3) selected from the group of combinations consisting of:
a CDRH3 comprising or consisting of the amino acid sequence of SEQ ID NO: 8 and
a CDRL3 comprising or consisting of the amino acid sequence of SEQ ID NO: 9;
a CDRH3 comprising or consisting of the amino acid sequence of SEQ ID NO: 17 and
a CDRL3 comprising or consisting of the amino acid sequence of SEQ ID NO: 18.

In a preferred embodiment, the present invention relates to an antagonistic antigen binding protein that specifically binds to PD-1, wherein said antigen binding protein comprises a combination of a light chain variable domain having a sequence with at least 90% identity to SEQ ID NO: 3 and a heavy chain variable domain having a sequence with at least 90% identity to SEQ ID NO: 2.

In a further preferred embodiment, the present invention relates to an antagonistic antigen binding protein that specifically binds to PD-1, wherein said antigen binding protein comprises a combination of a CDRH3 comprising or consisting of the amino acid sequence of SEQ ID NO: 8 and a CDRL3 comprising or consisting of the amino acid sequence of SEQ ID NO: 9.

In a preferred embodiment of the fourth aspect of the present invention, the antagonistic antigen binding protein specifically binds to PD-1, wherein said antigen binding protein comprises a combination of a light chain variable domain and a heavy chain variable domain selected from the group of combinations consisting of:
a light chain variable domain having a sequence with at least 95% identity to SEQ ID NO: 3 and
a heavy chain variable domain having a sequence with at least 95% identity to SEQ ID NO: 2;
a light chain variable domain having a sequence with at least 95% identity to SEQ ID NO: 12 and
a heavy chain variable domain having a sequence with at least 95% identity to SEQ ID NO: 11.

In a further preferred embodiment, the present invention relates to an antagonistic antigen binding protein that specifically binds to PD-1, wherein said antigen binding protein comprises a combination of a light chain variable domain having a sequence with at least 95% identity to SEQ ID NO: 3 and a heavy chain variable domain having a sequence with at least 95% identity to SEQ ID NO: 2.

In a further preferred embodiment of the fourth aspect of the present invention, the antagonistic antigen binding protein specifically binds to PD-1, wherein said antigen binding protein comprises a combination of a light chain variable domain and a heavy chain variable domain selected from the group of combinations consisting of:
a light chain variable domain having a sequence with at least 99% identity to SEQ ID NO: 3 and
a heavy chain variable domain having a sequence with at least 99% identity to SEQ ID NO: 2;
a light chain variable domain having a sequence with at least 99% identity to SEQ ID NO: 12 and
a heavy chain variable domain having a sequence with at least 99% identity to SEQ ID NO: 11.

In a further preferred embodiment, the present invention relates to an antagonistic antigen binding protein that specifically binds to PD-1, wherein said antigen binding protein comprises a combination of a light chain variable domain having a sequence with at least 99% identity to SEQ ID NO: 3 and a heavy chain variable domain having a sequence with at least 99% identity to SEQ ID NO: 2.

In a further preferred embodiment of the fourth aspect of the present invention, the antagonistic antigen binding protein specifically binds to PD-1, wherein said antigen binding protein comprises a combination of a complementarity determining region 3 of the heavy chain (CDRH3) and a complementarity determining region 3 of the light chain (CDRL3) selected from the group of combinations consisting of:
a CDRH3 comprising or consisting of the amino acid sequence of SEQ ID NO: 8 and
a CDRL3 comprising or consisting of the amino acid sequence of SEQ ID NO: 9;
a CDRH3 comprising or consisting of the amino acid sequence of SEQ ID NO: 17 and
a CDRL3 comprising or consisting of the amino acid sequence of SEQ ID NO: 18.

In a further preferred embodiment, the present invention relates to an antagonistic antigen binding protein that specifically binds to PD-1, wherein said antigen binding protein comprises a combination of a CDRH3 comprising or consisting of the amino acid sequence of SEQ ID NO: 8 and a CDRL3 comprising or consisting of the amino acid sequence of SEQ ID NO: 9.Preferably, the antagonistic antigen binding protein specifically binds to PD-1, wherein said antigen binding protein further comprises one or more selected from the group consisting of a CDRH1 comprising or consisting of the amino acid sequence of SEQ ID NOs: 4 or 13, a CDRH2 comprising or consisting of the amino acid sequence of SEQ ID NOs: 6 or 15, CDRL1 comprising or consisting of the amino acid sequence of SEQ ID NOs: 5 or 14 and a CDRL2 comprising or consisting of the amino acid sequence of SEQ ID NOs: 7 or 16.

For example, the antagonistic antigen binding protein that specifically binds to PD-1, wherein said antigen binding protein comprises
a CDRH3 comprising or consisting of the amino acid sequence of SEQ ID NO: 8 and
a CDRL3 comprising or consisting of the amino acid sequence of SEQ ID NO: 9;
a CDRH1 comprising or consisting of the amino acid sequence of SEQ ID NO: 4 and
a CDRL1 comprising or consisting of the amino acid sequence of SEQ ID NO: 5;
a CDRH2 comprising or consisting of the amino acid sequence of SEQ ID NO: 6 and
a CDRL2 comprising or consisting of the amino acid sequence of SEQ ID NO: 7.

Preferably, also within the scope of the present invention is the antagonistic antigen binding protein as specified above comprising one amino acid exchange in CDRH1, CDRL1, CDRH2 or CDRL2.

For example, the antagonistic antigen binding protein that specifically binds to PD-1, wherein said antigen binding protein comprises
- a CDRH3 comprising or consisting of the amino acid sequence of SEQ ID NO: 17 and
- a CDRL3 comprising or consisting of the amino acid sequence of SEQ ID NO: 18;
- a CDRH1 comprising or consisting of the amino acid sequence of SEQ ID NO: 13 and
- a CDRL1 comprising or consisting of the amino acid sequence of SEQ ID NO: 14;
- a CDRH2 comprising or consisting of the amino acid sequence of SEQ ID NO: 15 and
- a CDRL2 comprising or consisting of the amino acid sequence of SEQ ID NO: 16.

Preferably, also within the scope of the present invention is the antagonistic antigen binding protein as specified above comprising one amino acid exchange in CDRH1, CDRL1, CDRH2 or CDRL2.

In a further preferred embodiment of the fourth aspect, the antagonistic antigen binding protein that specifically binds to PD-1 is an antibody, an antibody-like protein or a fragment thereof. Preferably, the antibody is selected from the group consisting of a human antibody, a humanized antibody, chimeric antibody, a monoclonal antibody, a multispecific antibody, a recombinant antibody, an antigen-binding antibody fragment, a single chain antibody, a single chain variable fragment antibody, a diabody, a Fab fragment, an F(ab)2 fragment, an antibody mimetic, an IgG1 antibody, an IgG2 antibody, an IgG3 antibody, and an IgG4 antibody.

In a further preferred embodiment of the fourth aspect, the antagonistic antigen binding protein that specifically binds to PD-1 binds to PD-1 with a Kd of less than 100 nM, of less than 50 nM, of less than 10 nM, of less than 1 nM, of less than 100 pM, of less than 10 pM, or of less than 5 pM. For instance, the antagonistic antigen binding protein that specifically binds to PD-1 binds to PD-1 with a Kd between 5 pM and 100 nM, 5 pM and 50 nM, 5 PM and 10 nM, 5 pM and 1 nM, 5 pM and 100 pM, such as between 5 pM and 10 pM.

In a further preferred embodiment of the fourth aspect, the antagonistic antigen binding protein that specifically binds to PD-1 can block the binding of a ligand to PD-1 with an IC50 of less than 10 nM, less than InM, or less than 200 pM. For instance, the antagonistic antigen binding protein that specifically binds to PD-1 can block the binding of a ligand to PD-1 with an IC50 between 200 pM and 10 nM, such as between 200 pM and InM.

In a further preferred embodiment of the fourth aspect, the antagonistic antigen binding protein that specifically binds to PD-1 stimulates T cell proliferation.

In a further preferred embodiment of the fourth aspect, the antagonistic antigen binding protein that specifically binds to PD-1 induces the proliferation of lymphocytes.

In a further preferred embodiment of the fourth aspect, the antagonistic antigen binding protein that specifically binds to PD-1 induces secretion of IL-2 and/or IFNγ.

In a further preferred embodiment of the fourth aspect, the antagonistic antigen binding protein that specifically binds to PD-1 reduces tumor volume by at least 50%, at least 60%, at least 70%, at least 80% or at least 90% compared to baseline value.

In a fifth aspect, the present invention relates to an antagonistic antigen binding protein that specifically binds to PD-L1, wherein said antigen binding protein comprises either
(i) a combination of a light chain variable domain and a heavy chain variable domain selected from the group of combinations consisting of:
- a light chain variable domain having a sequence with at least 90% identity to SEQ ID NO: 21 and
- a heavy chain variable domain having a sequence with at least 90% identity to SEQ ID NO: 20;
- a light chain variable domain having a sequence with at least 90% identity to SEQ ID NO: 30 and
- a heavy chain variable domain having a sequence with at least 90% identity to SEQ ID NO: 29;
- a light chain variable domain having a sequence with at least 90% identity to SEQ ID NO: 84 and
- a heavy chain variable domain having a sequence with at least 90% identity to SEQ ID NO: 83;
- a light chain variable domain having a sequence with at least 90% identity to SEQ ID NO: 93 and
- a heavy chain variable domain having a sequence with at least 90% identity to SEQ ID NO: 92;
- a light chain variable domain having a sequence with at least 90% identity to SEQ ID NO: 102 and
- a heavy chain variable domain having a sequence with at least 90% identity to SEQ ID NO: 101;
(ii) a combination of a complementarity determining region 3 of the heavy chain (CDRH3) and a complementarity determining region 3 of the light chain (CDRL3) selected from the group of combinations consisting of:
- a CDRH3 comprising or consisting of the amino acid sequence of SEQ ID NO: 26 and
- a CDRL3 comprising or consisting of the amino acid sequence of SEQ ID NO: 27;
- a CDRH3 comprising or consisting of the amino acid sequence of SEQ ID NO: 35 and
- a CDRL3 comprising or consisting of the amino acid sequence of SEQ ID NO: 36;
- a CDRH3 comprising or consisting of the amino acid sequence of SEQ ID NO: 89 and
- a CDRL3 comprising or consisting of the amino acid sequence of SEQ ID NO: 90;
- a CDRH3 comprising or consisting of the amino acid sequence of SEQ ID NO: 98 and
- a CDRL3 comprising or consisting of the amino acid sequence of SEQ ID NO: 99;
- a CDRH3 comprising or consisting of the amino acid sequence of SEQ ID NO: 107 and
- a CDRL3 comprising or consisting of the amino acid sequence of SEQ ID NO: 108.

In a preferred embodiment, the present invention relates to an antagonistic antigen binding protein that specifically binds to PD-L1, wherein said antigen binding protein comprises a combination of a light chain variable domain having a sequence with at least 90% identity to SEQ ID NO: 30 and a heavy chain variable domain having a sequence with at least 90% identity to SEQ ID NO: 29.

In a further preferred embodiment, the present invention relates to an antagonistic antigen binding protein that specifically binds to PD-L1, wherein said antigen binding protein comprises a combination of a CDRH3 comprising or consisting of the amino acid sequence of SEQ ID NO: 35 and a CDRL3 comprising or consisting of the amino acid sequence of SEQ ID NO: 36.

In a preferred embodiment of the fifth aspect of the present invention, the antagonistic antigen binding protein specifically binds to PD-L1, wherein said antigen binding protein comprises a combination of a light chain variable domain and a heavy chain variable domain selected from the group of combinations consisting of:
- a light chain variable domain having a sequence with at least 95% identity to SEQ ID NO: 21 and
- a heavy chain variable domain having a sequence with at least 95% identity to SEQ ID NO: 20;
- a light chain variable domain having a sequence with at least 90% identity to SEQ ID NO: 30 and
- a heavy chain variable domain having a sequence with at least 95% identity to SEQ ID NO: 29;
- a light chain variable domain having a sequence with at least 95% identity to SEQ ID NO: 84 and
- a heavy chain variable domain having a sequence with at least 95% identity to SEQ ID NO: 83;
- a light chain variable domain having a sequence with at least 95% identity to SEQ ID NO: 93 and
- a heavy chain variable domain having a sequence with at least 95% identity to SEQ ID NO: 92;
- a light chain variable domain having a sequence with at least 95% identity to SEQ ID NO: 102 and
- a heavy chain variable domain having a sequence with at least 95% identity to SEQ ID NO: 101.

In a further preferred embodiment, the present invention relates to an antagonistic antigen binding protein that specifically binds to PD-L1, wherein said antigen binding protein comprises a combination of a light chain variable domain having a sequence with at least 95% identity to SEQ ID NO: 30 and a heavy chain variable domain having a sequence with at least 95% identity to SEQ ID NO: 29.

In a further preferred embodiment of the fifth aspect of the present invention, the antagonistic antigen binding protein specifically binds to PD-L1, wherein said antigen binding protein comprises a combination of a light chain variable domain and a heavy chain variable domain selected from the group of combinations consisting of:
- a light chain variable domain having a sequence with at least 99% identity to SEQ ID NO: 21 and
- a heavy chain variable domain having a sequence with at least 99% identity to SEQ ID NO: 20;
- a light chain variable domain having a sequence with at least 99% identity to SEQ ID NO: 30 and
- a heavy chain variable domain having a sequence with at least 99% identity to SEQ ID NO: 29;
- a light chain variable domain having a sequence with at least 99% identity to SEQ ID NO: 84 and
- a heavy chain variable domain having a sequence with at least 99% identity to SEQ ID NO: 83;
- a light chain variable domain having a sequence with at least 99% identity to SEQ ID NO: 93 and
- a heavy chain variable domain having a sequence with at least 99% identity to SEQ ID NO: 92;
- a light chain variable domain having a sequence with at least 99% identity to SEQ ID NO: 102 and
- a heavy chain variable domain having a sequence with at least 99% identity to SEQ ID NO: 101.

In a preferred embodiment, the present invention relates to an antagonistic antigen binding protein that specifically binds to PD-L1, wherein said antigen binding protein comprises a combination of a light chain variable domain having a sequence with at least 99% identity to SEQ ID NO: 30 and a heavy chain variable domain having a sequence with at least 99% identity to SEQ ID NO: 29.

In a further preferred embodiment of the fifth aspect of the present invention, the antagonistic antigen binding protein specifically binds to PD-L1, wherein said antigen binding protein comprises a combination of a complementarity determining region 3 of the heavy chain (CDRH3) and a complementarity determining region 3 of the light chain (CDRL3) selected from the group of combinations consisting of:
- a CDRH3 comprising or consisting of the amino acid sequence of SEQ ID NO: 26 and
- a CDRL3 comprising or consisting of the amino acid sequence of SEQ ID NO: 27;
- a CDRH3 comprising or consisting of the amino acid sequence of SEQ ID NO: 35 and
- a CDRL3 comprising or consisting of the amino acid sequence of SEQ ID NO: 36;
- a CDRH3 comprising or consisting of the amino acid sequence of SEQ ID NO: 89 and
- a CDRL3 comprising or consisting of the amino acid sequence of SEQ ID NO: 90;
- a CDRH3 comprising or consisting of the amino acid sequence of SEQ ID NO: 98 and
- a CDRL3 comprising or consisting of the amino acid sequence of SEQ ID NO: 99;
- a CDRH3 comprising or consisting of the amino acid sequence of SEQ ID NO: 107 and
- a CDRL3 comprising or consisting of the amino acid sequence of SEQ ID NO: 108.

In a further preferred embodiment, the present invention relates to an antagonistic antigen binding protein that specifically binds to PD-L1, wherein said antigen binding protein comprises a combination of a CDRH3 comprising or consisting of the amino acid sequence of SEQ ID NO: 35 and a CDRL3 comprising or consisting of the amino acid sequence of SEQ ID NO: 36.

Preferably, the antagonistic antigen binding protein specifically binds to PD-L1, wherein said antigen binding protein further comprises one or more selected from the group consisting of a CDRH1 comprising or consisting of the amino acid sequence of SEQ ID NOs: 22 or 31, a CDRH2 comprising or consisting of the amino acid sequence of SEQ ID NOs: 24 or 33, CDRL1 comprising or consisting of the amino acid sequence of SEQ ID NOs: 23 or 32 and a CDRL2 comprising or consisting of the amino acid sequence of SEQ ID NOs: 25 or 34.

For example, the antagonistic antigen binding protein that specifically binds to PD-L1, wherein said antigen binding protein comprises
- a CDRH3 comprising or consisting of the amino acid sequence of SEQ ID NO: 26 and
- a CDRL3 comprising or consisting of the amino acid sequence of SEQ ID NO: 27;
- a CDRH1 comprising or consisting of the amino acid sequence of SEQ ID NO: 22 and
- a CDRL1 comprising or consisting of the amino acid sequence of SEQ ID NO: 23;
- a CDRH2 comprising or consisting of the amino acid sequence of SEQ ID NO: 24 and
- a CDRL2 comprising or consisting of the amino acid sequence of SEQ ID NO: 25.

Preferably, also within the scope of the present invention is the antagonistic antigen binding protein as specified above comprising one amino acid exchange in CDRH1, CDRL1, CDRH2 or CDRL2.

For example, the antagonistic antigen binding protein that specifically binds to PD-L1, wherein said antigen binding protein comprises a CDRH3 comprising or consisting of the amino acid sequence of SEQ ID NO: 35 and
a CDRL3 comprising or consisting of the amino acid sequence of SEQ ID NO: 36;
a CDRH1 comprising or consisting of the amino acid sequence of SEQ ID NO: 31 and
a CDRL1 comprising or consisting of the amino acid sequence of SEQ ID NO: 32;
a CDRH2 comprising or consisting of the amino acid sequence of SEQ ID NO: 33 and
a CDRL2 comprising or consisting of the amino acid sequence of SEQ ID NO: 34.

Preferably, also within the scope of the present invention is the antagonistic antigen binding protein as specified above comprising one amino acid exchange in CDRH1, CDRL1, CDRH2 or CDRL2.

For example, the antagonistic antigen binding protein that specifically binds to PD-L1, wherein said antigen binding protein comprises
a CDRH3 comprising or consisting of the amino acid sequence of SEQ ID NO: 89 and
a CDRL3 comprising or consisting of the amino acid sequence of SEQ ID NO: 90;
a CDRH1 comprising or consisting of the amino acid sequence of SEQ ID NO: 85 and
a CDRL1 comprising or consisting of the amino acid sequence of SEQ ID NO: 86;
a CDRH2 comprising or consisting of the amino acid sequence of SEQ ID NO: 87 and
a CDRL2 comprising or consisting of the amino acid sequence of SEQ ID NO: 88.

Preferably, also within the scope of the present invention is the antagonistic antigen binding protein as specified above comprising one amino acid exchange in CDRH1, CDRL1, CDRH2 or CDRL2.

For example, the antagonistic antigen binding protein that specifically binds to PD-L1, wherein said antigen binding protein comprises
a CDRH3 comprising or consisting of the amino acid sequence of SEQ ID NO: 98 and
a CDRL3 comprising or consisting of the amino acid sequence of SEQ ID NO: 99;
a CDRH1 comprising or consisting of the amino acid sequence of SEQ ID NO: 94 and
a CDRL1 comprising or consisting of the amino acid sequence of SEQ ID NO: 95;
a CDRH2 comprising or consisting of the amino acid sequence of SEQ ID NO: 96 and
a CDRL2 comprising or consisting of the amino acid sequence of SEQ ID NO: 97.

Preferably, also within the scope of the present invention is the antagonistic antigen binding protein as specified above comprising one amino acid exchange in CDRH1, CDRL1, CDRH2 or CDRL2.

For example, the antagonistic antigen binding protein that specifically binds to PD-L1, wherein said antigen binding protein comprises
a CDRH3 comprising or consisting of the amino acid sequence of SEQ ID NO: 107 and
a CDRL3 comprising or consisting of the amino acid sequence of SEQ ID NO: 108;
a CDRH1 comprising or consisting of the amino acid sequence of SEQ ID NO: 103 and
a CDRL1 comprising or consisting of the amino acid sequence of SEQ ID NO: 104;
a CDRH2 comprising or consisting of the amino acid sequence of SEQ ID NO: 105 and
a CDRL2 comprising or consisting of the amino acid sequence of SEQ ID NO: 106.

Preferably, also within the scope of the present invention is the antagonistic antigen binding protein as specified above comprising one amino acid exchange in CDRH1, CDRL1, CDRH2 or CDRL2.

In a further preferred embodiment of the fifth aspect, the antagonistic antigen binding protein that specifically binds to PD-L1 is an antibody, an antibody-like protein or a fragment thereof. Preferably, the antibody is selected from the group consisting of a human antibody, a humanized antibody, chimeric antibody, a monoclonal antibody, a multispecific antibody, a recombinant antibody, an antigen-binding antibody fragment, a single chain antibody, a single chain variable fragment antibody, a diabody, a Fab fragment, an F(ab)2 fragment, an antibody mimetic, an IgG1 antibody, an IgG2 antibody, an IgG3 antibody, and an IgG4 antibody.

In a further preferred embodiment of the fifth aspect, the antagonistic antigen binding protein that specifically binds to PD-L1 binds to PD-L1 with a Kd of less than 100 nM, of less than 50 nM, of less than 10 nM, of less than 1 nM, of less than 100 pM, of less than 10 pM, or of less than 5 pM. For instance, the antagonistic antigen binding protein that specifically binds to PD-L1 binds to PD-L1 with a Kd between 5 pM and 100 nM, 5 pM and 50 nM, 5 PM and 10 nM, 5 PM and 1 nM, 5 PM and 100 pM, such as between 5 pM and 10 pM.

In a further preferred embodiment of the fifth aspect, the antagonistic antigen binding protein that specifically binds to PD-L1 can block the binding of a ligand to PD-L1 with an IC50 of less than 10 nM, less than InM, or less than 200 pM. For instance, the antagonistic antigen binding protein that specifically binds to PD-L1 can block the binding of a ligand to PD-L1 with an IC50 between 200 pM and 10 nM, such as between 200 pM and 1 nM.

In a further preferred embodiment of the fifth aspect, the antagonistic antigen binding protein that specifically binds to PD-L1 stimulates T cell proliferation.

In a further preferred embodiment of the fifth aspect, the antagonistic antigen binding protein that specifically binds to PD-L1 induces the proliferation of lymphocytes.

In a further preferred embodiment of the fifth aspect, the antagonistic antigen binding protein that specifically binds to PD-L1 induces secretion of IL-2 and/or IFNγ.

In a further preferred embodiment of the fifth aspect, the antagonistic antigen binding protein that specifically binds to PD-L1 reduces tumor volume by at least 50%, at least 60%, at least 70%, at least 80% or at least 90% compared to baseline value.

In a sixth aspect, the present invention relates to an antagonistic antigen binding protein that specifically binds to LAG-3, wherein said antigen binding protein comprises either
(i) a combination of a light chain variable domain and a heavy chain variable domain selected from the group of combinations consisting of:
a light chain variable domain having a sequence with at least 90% identity to SEQ ID NO: 39 and
a heavy chain variable domain having a sequence with at least 90% identity to SEQ ID NO: 38;
a light chain variable domain having a sequence with at least 90% identity to SEQ ID NO: 48 and
a heavy chain variable domain having a sequence with at least 90% identity to SEQ ID NO: 47;
a light chain variable domain having a sequence with at least 90% identity to SEQ ID NO: 57 and a heavy chain variable domain having a sequence with at least 90% identity to SEQ ID NO: 56;
a light chain variable domain having a sequence with at least 90% identity to SEQ ID NO: 66 and
a heavy chain variable domain having a sequence with at least 90% identity to SEQ ID NO: 65;
a light chain variable domain having a sequence with at least 90% identity to SEQ ID NO: 75 and
a heavy chain variable domain having a sequence with at least 90% identity to SEQ ID NO: 74;
(ii) a combination of a complementarity determining region 3 of the heavy chain (CDRH3) and a complementarity determining region 3 of the light chain (CDRL3) selected from the group of combinations consisting of:
a CDRH3 comprising or consisting of the amino acid sequence of SEQ ID NO: 44 and
a CDRL3 comprising or consisting of the amino acid sequence of SEQ ID NO: 45;
a CDRH3 comprising or consisting of the amino acid sequence of SEQ ID NO: 53 and
a CDRL3 comprising or consisting of the amino acid sequence of SEQ ID NO: 54;
a CDRH3 comprising or consisting of the amino acid sequence of SEQ ID NO: 62 and
a CDRL3 comprising or consisting of the amino acid sequence of SEQ ID NO: 63;
a CDRH3 comprising or consisting of the amino acid sequence of SEQ ID NO: 71 and
a CDRL3 comprising or consisting of the amino acid sequence of SEQ ID NO: 72;
a CDRH3 comprising or consisting of the amino acid sequence of SEQ ID NO: 80 and
a CDRL3 comprising or consisting of the amino acid sequence of SEQ ID NO: 81.

In a preferred embodiment, the present invention relates to an antagonistic antigen binding protein that specifically binds to LAG-3, wherein said antigen binding protein comprises a combination of a light chain variable domain having a sequence with at least 90% identity to SEQ ID NO: 39 and a heavy chain variable domain having a sequence with at least 90% identity to SEQ ID NO: 38.

In a further preferred embodiment, the present invention relates to an antagonistic antigen binding protein that specifically binds to LAG-3, wherein said antigen binding protein comprises a combination of a CDRH3 comprising or consisting of the amino acid sequence of SEQ ID NO: 44 and a CDRL3 comprising or consisting of the amino acid sequence of SEQ ID NO: 45.

In a further preferred embodiment, the present invention relates to an antagonistic antigen binding protein that specifically binds to LAG-3, wherein said antigen binding protein comprises a combination of a light chain variable domain having a sequence with at least 90% identity to SEQ ID NO: 48 and a heavy chain variable domain having a sequence with at least 90% identity to SEQ ID NO: 47.

In a further preferred embodiment, the present invention relates to an antagonistic antigen binding protein that specifically binds to LAG-3, wherein said antigen binding protein comprises a combination of a CDRH3 comprising or consisting of the amino acid sequence of SEQ ID NO: 53 and a CDRL3 comprising or consisting of the amino acid sequence of SEQ ID NO: 54.

In a preferred embodiment of the sixth aspect of the present invention, the antagonistic antigen binding protein specifically binds to LAG-3, wherein said antigen binding protein comprises a combination of a light chain variable domain and a heavy chain variable domain selected from the group of combinations consisting of:
a light chain variable domain having a sequence with at least 95% identity to SEQ ID NO: 39 and
a heavy chain variable domain having a sequence with at least 95% identity to SEQ ID NO: 38;
a light chain variable domain having a sequence with at least 95% identity to SEQ ID NO: 48 and
a heavy chain variable domain having a sequence with at least 95% identity to SEQ ID NO: 47;
a light chain variable domain having a sequence with at least 95% identity to SEQ ID NO: 57 and
a heavy chain variable domain having a sequence with at least 95% identity to SEQ ID NO: 56;
a light chain variable domain having a sequence with at least 95% identity to SEQ ID NO: 66 and
a heavy chain variable domain having a sequence with at least 95% identity to SEQ ID NO: 65;
a light chain variable domain having a sequence with at least 95% identity to SEQ ID NO: 75 and
a heavy chain variable domain having a sequence with at least 95% identity to SEQ ID NO: 74.

In a further preferred embodiment, the present invention relates to an antagonistic antigen binding protein that specifically binds to LAG-3, wherein said antigen binding protein comprises a combination of a light chain variable domain having a sequence with at least 95% identity to SEQ ID NO: 39 and a heavy chain variable domain having a sequence with at least 95% identity to SEQ ID NO: 38.

In a further preferred embodiment, the present invention relates to an antagonistic antigen binding protein that specifically binds to LAG-3, wherein said antigen binding protein comprises a combination of a light chain variable domain having a sequence with at least 95% identity to SEQ ID NO: 48 and a heavy chain variable domain having a sequence with at least 95% identity to SEQ ID NO: 47.

In a further preferred embodiment of the sixth aspect of the present invention, the antagonistic antigen binding protein specifically binds to LAG-3, wherein said antigen binding protein comprises a combination of a light chain variable domain and a heavy chain variable domain selected from the group of combinations consisting of:
a light chain variable domain having a sequence with at least 99% identity to SEQ ID NO: 39 and
a heavy chain variable domain having a sequence with at least 99% identity to SEQ ID NO: 38;
a light chain variable domain having a sequence with at least 99% identity to SEQ ID NO: 48 and
a heavy chain variable domain having a sequence with at least 99% identity to SEQ ID NO: 47;
a light chain variable domain having a sequence with at least 99% identity to SEQ ID NO: 57 and
a heavy chain variable domain having a sequence with at least 99% identity to SEQ ID NO: 56;
a light chain variable domain having a sequence with at least 99% identity to SEQ ID NO: 66 and
a heavy chain variable domain having a sequence with at least 99% identity to SEQ ID NO: 65;
a light chain variable domain having a sequence with at least 99% identity to SEQ ID NO: 75 and
a heavy chain variable domain having a sequence with at least 99% identity to SEQ ID NO: 74.

In a further preferred embodiment, the present invention relates to an antagonistic antigen binding protein that specifically binds to LAG-3, wherein said antigen binding protein comprises a combination of a light chain variable domain having a sequence with at least 99% identity to SEQ ID NO: 39 and a heavy chain variable domain having a sequence with at least 99% identity to SEQ ID NO: 38.

In a further preferred embodiment, the present invention relates to an antagonistic antigen binding protein that specifically binds to LAG-3, wherein said antigen binding protein comprises a combination of a light chain variable domain having a sequence with at least 99% identity to SEQ ID NO: 48 and a heavy chain variable domain having a sequence with at least 99% identity to SEQ ID NO: 47.

In a further preferred embodiment of the sixth aspect of the present invention, the antagonistic antigen binding protein specifically binds to LAG-3, wherein said antigen binding protein comprises a combination of a complementarity determining region 3 of the heavy chain (CDRH3) and a complementarity determining region 3 of the light chain (CDRL3) selected from the group of combinations consisting of:
- a CDRH3 comprising or consisting of the amino acid sequence of SEQ ID NO: 44 and
- a CDRL3 comprising or consisting of the amino acid sequence of SEQ ID NO: 45;
- a CDRH3 comprising or consisting of the amino acid sequence of SEQ ID NO: 53 and
- a CDRL3 comprising or consisting of the amino acid sequence of SEQ ID NO: 54;
- a CDRH3 comprising or consisting of the amino acid sequence of SEQ ID NO: 62 and
- a CDRL3 comprising or consisting of the amino acid sequence of SEQ ID NO: 63;
- a CDRH3 comprising or consisting of the amino acid sequence of SEQ ID NO: 71 and
- a CDRL3 comprising or consisting of the amino acid sequence of SEQ ID NO: 72;
- a CDRH3 comprising or consisting of the amino acid sequence of SEQ ID NO: 80 and
- a CDRL3 comprising or consisting of the amino acid sequence of SEQ ID NO: 81.

In a further preferred embodiment, the present invention relates to an antagonistic antigen binding protein that specifically binds to LAG-3, wherein said antigen binding protein comprises a combination of a CDRH3 comprising or consisting of the amino acid sequence of SEQ ID NO: 44 and a CDRL3 comprising or consisting of the amino acid sequence of SEQ ID NO: 45.

In a further preferred embodiment, the present invention relates to an antagonistic antigen binding protein that specifically binds to LAG-3, wherein said antigen binding protein comprises a combination of a CDRH3 comprising or consisting of the amino acid sequence of SEQ ID NO: 53 and a CDRL3 comprising or consisting of the amino acid sequence of SEQ ID NO: 54.

Preferably, the antagonistic antigen binding protein specifically binds to LAG-3, wherein said antigen binding protein further comprises one or more selected from the group consisting of a CDRH1 comprising or consisting of the amino acid sequence of SEQ ID NOs: 40, 49, 58, 67, or 76, a CDRH2 comprising or consisting of the amino acid sequence of SEQ ID NOs: 42, 51, 60, 69, or 78, CDRL1 comprising or consisting of the amino acid sequence of SEQ ID NOs: 41, 50, 59, 68, or 77 and a CDRL2 comprising or consisting of the amino acid sequence of SEQ ID NOs: 43, 52, 61, 70, or 79.

For example, the antagonistic antigen binding protein specifically binds to LAG-3, wherein said antigen binding protein comprises
- a CDRH3 comprising or consisting of the amino acid sequence of SEQ ID NO: 44 and
- a CDRL3 comprising or consisting of the amino acid sequence of SEQ ID NO: 45;
- a CDRH1 comprising or consisting of the amino acid sequence of SEQ ID NO: 40 and
- a CDRL1 comprising or consisting of the amino acid sequence of SEQ ID NO: 41;
- a CDRH2 comprising or consisting of the amino acid sequence of SEQ ID NO: 42 and
- a CDRL2 comprising or consisting of the amino acid sequence of SEQ ID NO: 43.

Preferably, also within the scope of the present invention is the antagonistic antigen binding protein as specified above comprising one amino acid exchange in CDRH1, CDRL1, CDRH2 or CDRL2.

For example, the antagonistic antigen binding protein specifically binds to LAG-3, wherein said antigen binding protein comprises
- a CDRH3 comprising or consisting of the amino acid sequence of SEQ ID NO: 53 and
- a CDRL3 comprising or consisting of the amino acid sequence of SEQ ID NO: 54;
- a CDRH1 comprising or consisting of the amino acid sequence of SEQ ID NO: 49 and
- a CDRL1 comprising or consisting of the amino acid sequence of SEQ ID NO: 50;
- a CDRH2 comprising or consisting of the amino acid sequence of SEQ ID NO: 51 and
- a CDRL2 comprising or consisting of the amino acid sequence of SEQ ID NO: 52.

Preferably, also within the scope of the present invention is the antagonistic antigen binding protein as specified above comprising one amino acid exchange in CDRH1, CDRL1, CDRH2 or CDRL2.

For example, the antagonistic antigen binding protein specifically binds to LAG-3, wherein said antigen binding protein comprises
- a CDRH3 comprising or consisting of the amino acid sequence of SEQ ID NO: 62 and
- a CDRL3 comprising or consisting of the amino acid sequence of SEQ ID NO: 63;
- a CDRH1 comprising or consisting of the amino acid sequence of SEQ ID NO: 58 and
- a CDRL1 comprising or consisting of the amino acid sequence of SEQ ID NO: 59;
- a CDRH2 comprising or consisting of the amino acid sequence of SEQ ID NO: 60 and
- a CDRL2 comprising or consisting of the amino acid sequence of SEQ ID NO: 61.

Preferably, also within the scope of the present invention is the antagonistic antigen binding protein as specified above comprising one amino acid exchange in CDRH1, CDRL1, CDRH2 or CDRL2.

For example, the antagonistic antigen binding protein specifically binds to LAG-3, wherein said antigen binding protein comprises
- a CDRH3 comprising or consisting of the amino acid sequence of SEQ ID NO: 71 and
- a CDRL3 comprising or consisting of the amino acid sequence of SEQ ID NO: 72;
- a CDRH1 comprising or consisting of the amino acid sequence of SEQ ID NO: 67 and
- a CDRL1 comprising or consisting of the amino acid sequence of SEQ ID NO: 68;
- a CDRH2 comprising or consisting of the amino acid sequence of SEQ ID NO: 69 and
- a CDRL2 comprising or consisting of the amino acid sequence of SEQ ID NO: 70.

Preferably, also within the scope of the present invention is the antagonistic antigen binding protein as specified above comprising one amino acid exchange in CDRH1, CDRL1, CDRH2 or CDRL2.

For example, the antagonistic antigen binding protein specifically binds to LAG-3, wherein said antigen binding protein comprises
- a CDRH3 comprising or consisting of the amino acid sequence of SEQ ID NO: 80 and
- a CDRL3 comprising or consisting of the amino acid sequence of SEQ ID NO: 81;
- a CDRH1 comprising or consisting of the amino acid sequence of SEQ ID NO: 76 and
- a CDRL1 comprising or consisting of the amino acid sequence of SEQ ID NO: 77;
- a CDRH2 comprising or consisting of the amino acid sequence of SEQ ID NO: 78 and
- a CDRL2 comprising or consisting of the amino acid sequence of SEQ ID NO: 79.

Preferably, also within the scope of the present invention is the antagonistic antigen binding protein as specified above comprising one amino acid exchange in CDRH1, CDRL1, CDRH2 or CDRL2.

In a further preferred embodiment of the sixth aspect, the antagonistic antigen binding protein that specifically binds to LAG-3 is an antibody, an antibody-like protein or a fragment thereof. Preferably, the antibody is selected from the group consisting of a human antibody, a humanized antibody, chimeric antibody, a monoclonal antibody, a multispecific antibody, a recombinant antibody, an antigen-binding antibody fragment, a single chain antibody, a single chain variable fragment antibody, a diabody, a Fab fragment, an F(ab)2 fragment, an antibody mimetic, an IgG1 antibody, an IgG2 antibody, an IgG3 antibody, and an IgG4 antibody.

In a further preferred embodiment of the sixth aspect, the antagonistic antigen binding protein that specifically binds to LAG-3 binds to LAG-3 with a Kd of less than 100 nM, of less than 50 nM, of less than 10 nM, of less than 1 nM, of less than 100 pM, of less than 10 pM, or of less than 5 pM. For instance, the antagonistic antigen binding protein that specifically binds to LAG-3 binds to LAG-3 with a Kd between 5 pM and 100 nM, 5 pM and 50 nM, 5 PM and 10 nM, 5 pM and 1 nM, 5 pM and 100 pM, such as between 5 pM and 10 pM.

In a further preferred embodiment of the sixth aspect, the antagonistic antigen binding protein that specifically binds to LAG-3 can block the binding of a ligand to LAG-3 with an IC50 of less than 10 nM, less than 1 nM, or less than 200 pM. For instance, the antagonistic antigen binding protein that specifically binds to LAG-3 can block the binding of a ligand to LAG-3 with an IC50 between 200 pM and 10 nM, such as between 200 pM and 1 nM.

In a further preferred embodiment of the sixth aspect, the antagonistic antigen binding protein that specifically binds to LAG-3 stimulates T cell proliferation.

In a further preferred embodiment of the sixth aspect, the antagonistic antigen binding protein that specifically binds to LAG-3 induces the proliferation of lymphocytes.

In a further preferred embodiment of the sixth aspect, the antagonistic antigen binding protein that specifically binds to LAG-3 induces secretion of IL-2 and/or IFNγ.

In a further preferred embodiment of the sixth aspect, the antagonistic antigen binding protein that specifically binds to LAG-3 reduces tumor volume by at least 50%, at least 60%, at least 70%, at least 80% or at least 90% compared to baseline value.

In a seventh aspect, the present invention relates to a nucleic acid encoding the antagonistic antigen binding protein of any one of aspects 1 to 6 of the present invention.

In an eighth aspect, the present invention relates to a recombinant expression vector comprising the nucleic acid molecule of to the seventh aspect.

In a ninth aspect, the present invention relates to a host cell comprising the vector of the eighth aspect of the present invention.

In a tenth aspect, the present invention relates to a method of making the antagonistic antigen binding protein of any one of aspects 1 to 6 of the present invention comprising the step of preparing said antigen binding protein from a host cell expressing said antigen binding protein.

In an eleventh aspect, the present invention relates to an antagonistic antigen binding protein produced by the expression of recombinant DNA in the host cell of the ninth aspect of the present invention.

In a twelfth aspect, the present invention relates to a pharmaceutical composition comprising at least one antagonistic antigen binding protein according to any one of aspects 1 to 6 of the present invention, the nucleic acid according to the seventh aspect of the present invention or the vector according to the eighth aspect of the present invention and a pharmaceutically acceptable carrier.

In a preferred embodiment of the twelfth aspect, the pharmaceutical composition is adapted for parenteral administration. Pharmaceutical compositions adapted for parenteral administration include aqueous and non-aqueous sterile injectable solutions or suspensions, which may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring only the addition of a sterile liquid carrier, e.g., sterile saline solution for injections, immediately prior to use. Extemporaneous injection solutions and suspensions may be prepared from sterile powders, granules and tablets.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anaesthetic such as lidocaine to ease pain at the site of the injection. Generally, the ingredients are supplied either separately or mixed together in unit dosage form, for example, as a dry lyophilized powder or water-free concentrate in a hermetically-sealed container such as an ampule or sachet indicating the quantity of active agent. Where the composition is to be administered by infusion, it can be dispensed with an infusion bottle containing sterile pharmaceutical grade water or saline. Where the composition is administered by injection, an ampule of sterile saline can be provided so that the ingredients may be mixed prior to administration.

In a preferred embodiment of the twelfth aspect of the present invention, the pharmaceutical composition comprises at least one further active agent. Preferably, the at least one further active agent is selected from the group consisting of another antagonistic antigen binding protein according to any one of aspects 1 to 6 of the present invention, a checkpoint inhibitor, a chemotherapeutic drug, a radiotherapeutic drug, an anti-angiogenic agent, a cancer vaccine and an oncolytic virus. For example, the at least one further active agent is selected from the group consisting of carboplatin-paclitaxel, trastuzumab, pertuzumab, erlotinib, lapatinib, imatinib, vemurafenib, dabrafenib, trametinib, bevacizumab, sunitinib and pazopanib.

In a thirteenth aspect, the present invention relates to a kit comprising the pharmaceutical composition according to the twelfth aspect of the present invention and optionally at least one further active agent. Preferably, the at least one further active agent is selected from the group consisting of another antagonistic antigen binding protein according to any one of aspects 1 to 6 of the present invention, a checkpoint inhibitor, a chemotherapeutic drug, a radiotherapeutic drug, an anti-angiogenic agent, a cancer vaccine and an oncolytic virus. For example, the at least one further active agent is selected from the group consisting of carboplatin-paclitaxel, trastuzumab, pertuzumab, erlotinib, lapatinib, imatinib, vemurafenib, dabrafenib, trametinib, bevacizumab, sunitinib and pazopanib.

In a fourteenth aspect, the present invention relates to the antagonistic antigen binding protein according to any one of aspects 1 to 6 of the present invention, the nucleic acid of the seventh aspect of the present invention, the vector of the eighth aspect of the present invention or the pharmaceutical composition of the twelfth aspect of the present invention for use in the treatment of cancer and/or chronic infectious disease.

In a preferred embodiment of the fourteenth aspect of the present invention, the cancer is selected from the group consisting of
(a) Malignant neoplasms of lip, oral cavity and pharynx; and/or
(b) Malignant neoplasms of digestive organs; and/or
(c) Malignant neoplasms of respiratory and intrathoracic organs; and/or
(d) Malignant neoplasms of bone and articular cartilage; and/or
(e) Melanoma and other malignant neoplasms of skin; and/or
(f) Malignant neoplasms of mesothelial and soft tissue; and/or
(g) Malignant neoplasm of breast; and/or
(h) Malignant neoplasms of female genital organs; and/or
(i) Malignant neoplasms of male genital organs; and/or
(j) Malignant neoplasms of urinary tract; and/or
(k) Malignant neoplasms of eye, brain and other parts of central nervous system; and/or
(l) Malignant neoplasms of thyroid and other endocrine glands; and/or
(m) Malignant neoplasms of lymphoid, hematopoietic and related tissue.

Preferably, the cancer is selected from the group consisting of NSCLC (non-small cell lung cancer), melanoma, MSI (microsatellite instability associated cancer), bladder cancer, renal cancer, head and neck cancer, Hodgkin lymphoma, hepatocellular carcinoma (HCC) and gastric cancer.

In a further preferred embodiment of the fourteenth aspect of the present invention, the chronic infectious disease is selected from the group consisting of HBV, HCV, HIV, HSV, HPV, EBV, CMV and *Chlamydia*. Preferably, the chronic infectious disease is caused by HBV, HCV, HIV and HPV.

In a further preferred embodiment of the fourteenth aspect of the present invention, the at least one further active agent is administered to the subject in need thereof. Preferably, the at least one further active agent and the antagonistic binding protein of any of aspects 1 to 6 of the present invention, the nucleic acid of the seventh aspect of the present invention, the vector of the eighth aspect of the present invention or the pharmaceutical composition of the twelfth aspect of the present invention are administered simultaneously or sequentially or a combination thereof.

The following examples are merely illustrative of the present invention and should not be construed to limit the scope of the invention as indicated by the appended claims in any way.

EXAMPLES

Materials and Methods

Antibodies and Human Recombinant Proteins

The following antibodies were used: horseradish peroxidase (HRP)-conjugated anti-His mouse monoclonal antibody (Qiagen, Hilden, Germany); (HRP)-conjugated anti-M13 mouse monoclonal antibody (GE Healthcare, Chalfont St. Giles, UK); anti-human LAG-3 mouse monoclonal antibody (R&D Systems, Minneapolis, USA); anti-human PD-1 human monoclonal antibody Nivolumab (Opdivo®, Bristol-Myers Squibb, Princeton, NJ, USA); anti-human PD-L1 human monoclonal antibody (G&P Biosciences, Santa Clara, CA, USA); (HRP)-conjugated anti-human IgG (Promega Madison, WI, USA); PE/anti-human CD2 mouse monoclonal antibody (BioLegend Inc., San Diego, CA, USA); APC/anti-human CD3 mouse antibody; PE/anti-human CD4 mouse monoclonal antibody; PerCP/anti-human CD8 mouse monoclonal antibody (all from BD Biosciences, San Jose, CA, USA); (HRP)-conjugated anti-human IgG (Fab')2 goat monoclonal antibody (Abcam, Cambridge, UK); APC/anti-human IgG Fc mouse antibody; APC/Cy7 anti-human CD366 (TIM3) mouse antibody; APC/anti-human CD272 (BTLA) mouse antibody; APC/anti-human CD137 (4-1BB) mouse antibody; PE/anti-human CD134 (OX40) mouse antibody; Brilliant Violet 510TM/anti-mouse/rat/human CD27 hamster antibody; APC/anti-human/mouse/rat CD278 (ICOS) hamster antibody (all from BioLegend); FITC/anti-human TIGIT mouse antibody (Thermo Fisher Scientific, Waltham, MA, USA). The following recombinant chimeric proteins were used: human LAG-3/Fc; human PD-1/Fc;-human PD-L1/Fc; TIM3/Fc; BTLA/Fc; TIGIT/Fc; OX40/Fc; 4-1BB/Fc; CD27/Fc and ICOS/Fc;-human IgG1-Fc (all from R&D Systems).

Cell Cultures

MDA-MB-231 cells were cultured in Dulbecco's Modified Eagle's Medium (Gibco™ DMEM, Thermo Fisher Scientific). MCF7 cells were cultured in Modified Eagle's Medium (Gibco™ MEM, Thermo Fisher Scientific). Media were supplemented with 10% (vol/vol) heat-inactivated fetal bovine serum (FBS, Sigma-Aldrich, St. Louis, MO, USA), 50 IU ml$^{-1}$ penicillin, 50 µg ml$^{-1}$ streptomycin, 2 nM L-glutamine (all Gibco™, Thermo Fisher Scientific). Cell lines were purchased from the American Type Culture Collection (ATCC) and cultured in a humidified atmosphere containing 5% CO$_2$ at 37° C.

Isolation of Human Peripheral Blood Mononuclear Cells (hPBMCs)

Human Peripheral Blood Mononuclear Cells (hPBMCs) were isolated from blood of healthy donors by using ACCUSPIN™ System-Histopaque®-1077 (Sigma-Aldrich) following the manufacturer's instructions and frozen in a solution containing 90% FBS and 10% DMSO until use. Cryopreserved cell vials were gently thawed out by using RPMI 1640 medium (Gibco™, Thermo Fisher Scientific)

supplemented with 1% L-glutamine, 1% CTL-Wash™ (Cellular Technology Limited, Cleveland, OH, USA), and 100 U/ml Benzonase (Merck Millipore, Billerica, MA, USA). The collected hPBMCs were then washed by centrifugation, plated and incubated overnight at 37° C. in R10 medium consisting of RPMI 1640 (Gibco™, Thermo Fisher Scientific) supplemented with 10% inactivated fetal bovine serum (FBS, Sigma-Aldrich), 1% L-glutamine, 50 U ml-1 penicillin, 50 µg ml$^{-1}$ streptomycin and 1% HEPES (all Gibco™, Thermo Fisher Scientific). After an overnight resting, the hPBMCs were collected in PBS, counted by using the Muse® Cell Analyzer (Merck Millipore), resuspended at a density of $1\times10^6$ cells/ml.

FACS Analysis of Expression Levels of Immune Checkpoints on hPBMCs

The rescued and counted human Peripheral Blood Mononuclear Cells (hPBMCs) were activated with Dynabeads® Human T-Activator CD3/CD28 at a concentration of 1.103 beads/ml (Gibco™, Thermo Fisher Scientific). After 24-96 hours of activation, the cells were seeded in a round-bottom 96-well plate ($1\times10^6$ cells/well) and then centrifuged at 1200 rpm for 5 minutes to remove the supernatant. Unlabeled anti-LAG-3, anti-PD-1 (Nivolumab) or anti-PD-L1 primary antibodies were added to each well at a concentration of 10 µg/ml and incubated for 90 minutes at room temperature by gently shaking. After extensive washes, the cells were stained with 100 µl APC/anti-human IgG Fc antibody in FACS buffer (PBS, 1% FBS), and with 10 µg/ml PE/anti-human CD2 antibody (BioLegend) for 45 minutes at room temperature by gently shaking. The labeled antibodies APC/Cy7 anti-human CD366 (TIM3), APC/anti-human CD272 (BTLA), APC/anti-human CD137 (4-1BB), PE/anti-human CD134 (OX40), Brilliant Violet 510TM/anti-mouse/rat/human CD27, APC/anti-human/mouse/rat CD278 (ICOS), FITC/anti-human TIGIT antibodies were added to each well at a concentration of 10 µg/ml and incubated for 90 minutes at room temperature by gently shaking. After two washes with FACS buffer, the cells were resuspended in PBS, transferred to a 5 ml polystyrene round-bottom tube (BD Biosciences) and analyzed on CytoFLEX Flow Cytometer (Beckman Coulter, Brea, CA, USA).

Flow Cytometry Binding Assays of mAbs to hPBMCs

The human peripheral blood mononuclear cells (hPBMCs) isolated from healthy donors were thawed in RPMI 1640 medium (Gibco), supplemented with 2 mM L-glutamine, 10% (v/v) CTL wash supplement (CTL, Shaker Heights, Ohio, USA), 100U/ml Benzonase (Merck Millipore, Burlington, Massachusetts, United States). After centrifugation at 1200 rpm for 10 min, they were resuspended in complete RPMI medium supplemented with 10% (v/v) heat-inactivated fetal bovine serum (FBS, Sigma), 2 mM L-glutamine, 100U/ml penicillin and 100 µg/ml streptomicin (Gibco), HEPES 10 mM (Gibco). After resting for 16 h at 37° C. in a humidified atmosphere with 5% CO2, hPBMCs were counted, resuspended at a concentration of 10^6 viable cells/ml in complete RPMI medium (as above) and activated with Dynabeads Human T-Activator CD3/CD28 (Gibco), 25 µl beads/10^6 viable cells. 24h post activation, the cells were centrifuged and plated at 4×10^5 cells/well in PBS in a 96 well plate with round bottom. After one wash in PBS, they were incubated with 50 µl LIVE/DEAD™ Fixable Violet Dead Cell Stain (Invitrogen) for 30 min at +4° C. and washed once again. The mAbs, diluted in 100 µl PBS at the concentrations of 48 PM and 9,6 pM, were added to the cells and incubated for 1 h 30 min at room temperature in the dark with gentle shaking. The cells were washed twice as before and then incubated with 5 µl PE-conjugated anti-human CD2 (BD Biosciences) and 1:2000 APC-conjugated anti-human IgG, Fcγ specific antibody (Jackson immunoresearch), diluted in 100 µl FACS buffer (PBS1X 1% (v/v) FBS). After 45 min incubation in the same conditions as before, two washes with FACS buffer were performed and cells were resuspended in 150 µl PBS1X for the acquisition at CytoFLEX flow cytometer (Beckman Coulter).

Selection of scFv-Phage Clones

Phagemid particles were recovered from the library by using the M13-K07 helper phage (Invitrogen, Thermo Fisher Scientific), as previously described (De Lorenzo C, Clinical Cancer Research, 2002). For each round of selection phages ($10^{13}$ cfu) were blocked with 5% (wt/vol) Skim Milk Powder (Fluka Analytical, Sigma-Aldrich) in PBS. For the first round of selection, blocked phages were submitted to one round of selection performed by incubating them with activated lymphocytes ($1\times10^6$) overnight at 4° C. in rotation. After extensive washes with PBS, the bound phages were eluted from activated lymphocytes with 76 mM citric acid (pH 2.5) in PBS for 5 minutes, and then neutralized with IM Tris HCl (pH 8.0). The recovered phages were amplified by infecting E. coli TG1 cells to prepare phages for the next rounds of selection on the purified chimeric protein. To this aim, Nunc™ polypropylene tubes (Fisher Scientific, Thermo Fisher Scientific) were coated with the selected recombinant chimeric protein at a concentration of 20 µg/ml in a 0.05 M NaHCO$_3$ solution, for 72 hours at 4° C. Blocked phages were submitted to two following rounds of negative selection by incubating them in the tubes coated with rhIgG1-Fc protein for 2 hours at 4° C. in rotation. Unbound phages, recovered in the supernatant, were then incubated in the coated tubes, prepared as described above for positive selection, overnight at 4° C. in rotation, and eluted as described above. Alternatively, trypsin was used for the elution. Briefly, after extensive washes with PBS, the bound phages were incubated with 50 mM Tris☐HCl (pH 8.0) buffer containing 1 mM CaCl$_2$) for 1 hour at 4° C. in rotation, and then eluted from the chimeric proteins with trypsin (1 µg/ml) incubated for further 15 minutes at 25° C. by gently shaking. The reaction was then blocked by using protease inhibitors (complete™ EDTA-free Protease Inhibitor Cocktail, Sigma-Aldrich). Phages were then collected and stored at 4° C. until use.

DNA Fragment Preparation and High-Throughput Sequencing

For each sublibrary, the phagemid double strand DNAs containing the scFvs were purified from cultures of superinfected E. coli TG1 cells using Endo free Plasmid Maxi Kit (Qiagen). The full length scFvs were excised with restriction enzymes BamHI and HindIII (New England Biolabs) and purified with Wizard® SV Gel and PCR Clean-Up System (Promega) from 1.2% agarose gel. A second enzymatic excision was performed with NcoI and XhoI (New England Biolabs) to isolate the VHs from the previously purified material and then extracted from a 1.4% agarose gel. Library preparations for NGS, sequencing and preliminary bioinformatic analysis of the data were performed at the Center for Translational Genomics and Bioinformatics, Hospital San Raffaele, Milano, Italy. The VHs extracted from sub-libraries were bar-coded by TruSeq ChIP sample prep kit (Illumina). A complementary scheme for bar-coding was implemented to obtain a deep and suitable sequencing of VH mixtures of several sub cycles. Subcycles 2 and 3 for each target were mixed in a dedicated run. The first universal cycle 1 was sequenced separately to cover the larger complexity. The bar-coded samples were diluted to a final concentration of 10 pM and sequenced with 2×300 nt SBS kit v3 on an Illumina MiSeq apparatus.

scFv Recovery

The clones of interest were isolated from the sublibrary at cycle 3 of the corresponding target. For high-ranking clones, the QuickChange II XL Site-Directed Mutagenesis Kit (Agilent Technologies) was used to perform copies of clones with overlapping primers, designed within the corresponding HCDR3 regions, according to the procedure previously described 26. Briefly, the extension reactions were assembled as follows: 50-250 ng of template; ⅔ µL Quick-Solution reagent; 1 µL Pfu Ultra High Fidelity DNA polymerase (2.5 U/µL); 5 µL 10x reaction buffer; 1 µL dNTPmix; 125 ng forward primer; 125 ng reverse primer; H2O to a final volume of 50 µL. The template DNA was removed by restriction with 1 µL of DpnI enzyme, as suggested by the kit provider. An appropriate amount of reaction was used to transform XL10-GOLD ultracompetent cells (Agilent Technologies) and then plated on LB/agar containing 100 µg/ml Ampicillin. Some colonies were picked and evaluated by double digestion and sequencing. For low ranking clones, the DNA samples were isolated from cycle 3 by overlapping PCR. Briefly, Phusion High-Fidelity DNA Polymerase (Thermo Fisher Scientific) was used to perform two PCR reactions to obtain separately VH and VL fragments, using primers designed within the corresponding HCDR3 regions and in constant region of plasmid upstream and downstream of VH and VL. In a second step, the PCR fragments corresponding to each clone were mixed and extended to get the full scFvs. The reactions were assembled as follows: 150 ng of template for VH and VL fragments amplification and 10 ng of template (VH and VL fragments) for full scFv amplification; 0.5 µL Phusion DNA Polymerase (0.02 U/µl); 10 µL 5× Phusion HF Buffer; 1 µL dNTP mix; 0.5 µM forward primer; 0.5 µM reverse primer; 1.5 µl DMSO; H2O to a final volume of 50 µl.

Antibody Production and Purification

The scFvs of interest were converted into whole IgG4 antibodies by cloning the corresponding VH and VL cDNAs in the pEU vectors 8.2VH and 4.2VL, expressing respectively, the constant antibody heavy and light chains (Paciello R, J Gen Virol., 2016). Briefly, the VHs and VLs were amplified by CloneAmp HiFi PCR Premix in standard conditions with specific primers and purified with Wizard® SV Gel and PCR Clean-Up System (Promega) from 1.3% agarose gel. In-Fusion HD cloning kit (Clontech Laboratories, Mountain View, CA, USA) was used to clone the VHs in BamHI and BssHII (New England Biolabs) linearized pEU8.2VH vector, and the VLs in ApaLI and AvrII (New England Biolabs) linearized pEU4.2VL vector. Stellar Competent Cells (Clontech Laboratories, Inc, Mountain View, CA, USA) were transformed with the obtained vectors, and the colonies were screened by digestion and sequence analysis. The correct preps were co-transfected in HEK293-EBNA by using Lipofectamine Transfection Reagent (Life Technologies, Inc.) and grown up for about 10 days at 37° C. in chemical defined CD CHO medium (Gibco, Life Technologies, Inc.) supplemented with 5 ml of L-glutammine 200 mM (Gibco, Life Technologies), 5 ml of Penicillin-Streptomicyne 10,000 U/mL-10 mg/mL (Sigma-Aldirch) in 6-well plates or in 150 mm Corning® tissue-culture treated culture dishes. The conditioned media were collected and the antibodies were purified by using Protein A HP Spin Trap (GE Healthcare Life Sciences, New York, USA). The purity of the final products was evaluated by SDS-PAGE NuPAGE™ 4-12% Bis-Tris Protein Gels, 1.0 mm, 10-well (Thermo Fisher Scientific) followed by the staining with Coomassie blue solution (Biorad) for 20 minutes and destained with 7% of $CH_3COOH$ and 20% of Et-OH.

Enzyme-Linked Immunosorbent Assay (ELISA)

To confirm the binding specificity of the purified mAbs, ELISA assays were performed on chimeric proteins (coated at 5 µg/ml), tumor cells (PD-L1-positive breast cancer MDA-MB-231 cells or PD-L1-negative breast cancer MCF7), and untreated or activated hPBMCs. The ELISA assays on coated chimeric protein were performed by coating Nunc™ flat-bottom 96-well plates (Fisher Scientific, Thermo Fisher Scientific) with 5 µg/ml rhPD-1, rhPD-1 and rhLAG-3 recombinant proteins in a solution of 0.05 M $NaHCO_3$ for 72 hours at 37° C. After blocking of the coated 96-well plates with 5% Nonfat Dry Milk in PBS for 1 hour at 37° C., the purified mAbs were added at increasing concentrations (10-200 nM) to the plates in 2.5% Nonfat Dry Milk in PBS and incubated for 2 hours at room temperature by gently shaking. After extensive washes with PBS, the plates were incubated with (HRP)-conjugated anti-human IgG (Fab')2 goat monoclonal antibody (Abcam, Cambridge, UK) for 1 hour, washed again and incubated with TMB reagent for 10 min before quenching with an equal volume of 1N HCl.

Cell ELISA assays were performed by plating the cells in round-bottom 96-well plates ($2 \times 10^5$ cells or $2 \times 10^5$ lymphocytes for each well) and incubating them with increasing concentrations (0.5-200 nM) of mAbs in 2.5% Nonfat Dry Milk for 2 hours at room temperature with gentle agitation. Plates were then centrifuged, cell pellets were washed with PBS and incubated with HRP-conjugated anti-human IgG goat polyclonal antibody for 1 hour at room temperature. Following additional washes in PBS 1X, TMB reagent was added for 10 min before quenching with an equal volume of 1N HCl. Absorbance at 450 nm was measured by the Envision plate reader (Perkin Elmer, Waltham, MA, USA).

Competitive ELISA Assay

To determine whether the novel anti-PD-1 mAbs recognize different epitopes from Nivolumab, competitive ELISA assays were performed on coated PD-1/Fc chimeric protein (5 µg/ml). After blocking with 5% Nonfat Dry Milk in PBS, the coated 96-well plate was pre-incubated for 2 hours with saturating concentrations of each unlabelled mAb (400 nM) in 2.5% Nonfat Dry Milk in PBS in agitation at room temperature. After extensive washes with PBS, increasing concentrations of Biotinylated Nivolumab mAb were added. For the detection of the binding, the plate was incubated with HRP-conjugated Streptavidin (Biorad) for 30 minutes in agitation at room temperature, washed again and analyzed as described above.

Analysis of Binding of Antibodies to hPBMCs by FACS

Human Peripheral Blood Mononuclear Cells (hPBMCs) were rescued the day after thawing, counted and then activated with Dynabeads® Human T-Activator CD3/CD28 at a concentration of $1 \times 10^3$ beads/ml (Gibco™ Thermo Fisher Scientific). After 24-96 hours of activation, the cells were seeded in a round-bottom 96-well plate ($4 \times 10^5$ cells/well) and then centrifuged at 1200 rpm/min for 5 minutes to remove the supernatant. Anti-PD-L1 mAbs PD-L1_A and PD-L1_C were added at a concentration of 10 µg/ml and incubated for 90 minutes at room temperature by gently shaking. After extensive washes, the cells were stained with 100 µl of the APC/anti-human IgG Fc antibody in FACS buffer (PBS, 1% FBS), and with 10 µg/ml of PE/anti-human CD2 antibody (BioLegend) for 45 minutes at room temperature by gently shaking. After two washes with FACS buffer, the cells were resuspended in PBS, transferred into a polystyrene round-bottom tube (BD Biosciences) and analyzed on CytoFLEX Flow Cytometer (Beckman Coulter).

Lymphocyte Proliferation Assays

Lymphocyte Proliferation Assays were performed by using hPBMCs, counted as described above and resuspended at a density of 2×10⁶ cells/ml in pre-warmed 0.1% BSA/PBS solution. For the staining, pre-warmed 0.1% BSA/PBS solution containing CFDA-SE (Vybrant® Cell Tracer Kit, Invitrogen™, Thermo Fisher Scientific) at a concentration of 10 µM was used to resuspend hPBMCs at a density of 1×10⁶ cells/ml, that were incubated at 37° C. for 10 minutes. Ice-cold R10 medium was then used in order to permeabilize the cells by incubating on ice for further 5 min. The cells were then washed three times with PBS. Between the second and the third wash, the cells were incubated at 37° C. for 5 minutes to allow for the complete removal of excess of CFDA-SE. After the last wash and centrifugation at 1200 rpm for 10 minutes, the cells were resuspended at a density of 1×10⁶ cells/ml in R10 and plated into a 48-well plate (1×10⁶ cells/well). The Lymphocyte Proliferation Assays were performed by incubating the plated lymphocytes with 2.5 µg/ml Phytohemagglutinin-L (PHA-L, Roche), in the absence or in the presence of the selected anti-LAG-3 mAbs (10 µg/ml). The plates were then incubated at 37° C. for 5 days. At the end of treatment, each sample was recovered, resuspended in 100 µl of PBS and transferred into a round-bottom 96-well plate. First, the cells were incubated with violet LIVE/DEAD solution (Thermo Fisher Scientific) for 30 minutes at 4° C. After several washes, the samples were further incubated with the anti-human CD3 (APC), anti-CD4 (PE) and anti-CD8 (PerCP) antibodies (10 µl/sample) for 1 hour at 4° C. Finally, the cells were extensively washed, resuspended in 200 µl of PBS and transferred into 5 ml polystyrene round-bottom tubes (BD Biosciences) for the cytometric acquisition at CytoFLEX Flow Cytometer (Beckman Coulter).

Example 1: Selection of scFvs on Activated Human T Lymphocytes

Our goal was the generation of human antibody repertoires against Immune Checkpoints (IC). Since many IC are expressed on the surface of T lymphocytes and their expression is increased when T cells are exposed to antigen-dependent or independent stimuli, we sought to use unfractionated human peripheral blood mononuclear cells (hPBMCs) to screen libraries of human single chain antibody fragments (scFvs). To optimize the selection process, we first evaluated the kinetics and level of expression of ten different IC (indicated in Table 1) after in vitro activation with anti-CD3/CD28 beads. As shown in Table 1, peak expression measured by flow cytometric analysis varied between the different immunomodulators, however, the majority of them reached maximal levels of display after 96 hours of stimulation (see Table 1). After 96 hours stimulation, all IC were well expressed in more than 50% of the gated population except BTLA which maintained the same levels of surface display between untreated and activated hPBMC, and TIGIT which only slightly increased its expression levels. On the basis of this analysis we chose 96h as the time point for the activation of lymphocytes to be used for the selection of the human scFv library.

TABLE 1

Percentage of expression of each target on human lymphocytes untreated or activated at different time intervals.

| Immune checkpoint modulators | Levels of expression (%) of each target on human lymphocytes | | |
|---|---|---|---|
| | Not activated hPBMCs | Activated hPBMCs (24 h) | Activated hPBMCs (96 h) |
| LAG-3 | 1 | 53 | 59 |
| PD-L1 | 7 | 90 | 99 |
| PD-1 | 11 | 52 | 95 |
| TIM3 | 0.8 | 20 | 65 |
| BTLA | 47 | 33 | 40 |
| TIGIT | 11 | 17.5 | 21 |
| OX40 | 2 | 67 | 86 |
| 4-1BB | 1 | 53.5 | 70 |
| CD27 | 36 | 28 | 60 |
| ICOS | 3 | 32 | 90 |

About one million phage particles were selected by panning the library on activated hPBMCs as described in the Experimental Procedures Section (selection cycle 1). This pool of phages potentially represented a large collection of binders to many different IC, henceforth referred to as 'Immunome Library'. To facilitate the identification of binders to specific IC we used Fc-fusion recombinant proteins in successive pannings to perform ten different parallel selections of the Immunome Library leading to IC-specific repertoires.

Example 2: Identification of scFv Binders by Next Generation Sequencing

To identify individual phage clones selected by the combined ex vivo/in vitro approach, we sequenced the VH regions of the IC-specific Repertoires by massive parallel sequencing on the MiSeq Illumina platform (see Materials and Methods Section for details). To ensure efficient enrichment of target-specific phage, starting from the immunome library (cycle 1), we performed two subsequent cycles of selection on Fc-fusion recombinant proteins (cycles 2 and 3). Sequence analysis of the whole set of selections revealed that enrichments did occur already after cycle 2, but that significantly higher levels of enrichment (i.e.: at least 10-fold) were obtained after the third cycle (FIG. 1). Analysis of parallel sequencing data allowed us to remove VH sequences common to all selections and presumably due to the enrichment of Fc binders shared by the 10 biochemical baits. Similarly, the unspecific, biologically-enriched clones, bearing stop codons within the scFv coding sequence, were taken out from the list of potential binders. In order to obtain the most relevant specific clones for each target, we finally set a threshold of 85 counts per million to the list of the different selection cycles 3. In this way, we captured a detailed snapshot of the best potential binders for 9 out of 10 targets, which is shown in FIG. 1. TIGIT selection was indeed removed from analysis, since it did not display significant enrichment of sequences, possibly due to its low expression on activated hPBMCs (see Table 1).

The binders specific for three targets, i.e. LAG-3, PD-1 and PD-L1 were chosen for further studies, as antibodies specific for them, such as the anti-PD-1 Nivolumab, have been previously developed and widely used in clinic by demonstrating therapeutic benefits, and thus they can be used for comparison in biological assays. We rescued the best scFvs from the LAG-3, PD-1 and PD-L1 IC-specific repertoires, for conversion into fully human IgG4, with the aim to account, for further characterizations, on at least 5 effective antibodies for each of the three targets.

Example 3: Human IgGs Generated from Selected Binders Show High Binding Affinity and Receptor/Ligand Competitive Activity Human IgG4 antibodies generated from the best ranking LAG-3, PD-1 and PD-L1 binders were confirmed to recognize activated PBMC and recombinant proteins with low nanomolar or sub-nanomolar affinity (FIG. 2 and tables therein). In particular, some anti-PD-1 mAbs (i.e.: PD-1_A and PD-1_B) showed comparable or better apparent affinity as compared to the clinically validated Nivolumab. Most of the anti-PD-1 and anti-PD-L1 antibodies, including Nivolumab, displayed stronger binding to the recombinant protein compared to the activated hPBMCs, while the reverse was true for the anti-LAG3 antibodies. Because anti-PD-L1 antibodies have been shown to provide for clinical benefit by blocking interaction between PD-L1 expressed on cancer cells and PD-1 displayed by T cells, we tested whether the anti-PD-L1 antibodies would also recognize their targets on the surface of cancer cells. All anti-PD-L1 antibodies showed high affinity also for tumor cells expressing PD-L1, such as mammary MDA-MB-231 tumor cells, however the hierarchy of binding activity to tumor cells was different from the one observed with activated hPBMC (Table in FIG. 2). Moreover, we showed that mAb PD-L1 A and PD-L1 B were able to interfere with the recognition of PD-L1 by its two receptors PD-1 and B7.1 in competition ELISA assays.

Moreover, selected antibodies were also tested for binding to murine orthologue. Differently from Nivolumab one of the anti-PD-1 antibody was found to be crossreactive with murine PD-L1. It is therefore likely that PD-1_A recognizes a different epitope than Nivolumab as it is also evidenced from competitive ELISA assays performed by measuring the binding to PD-1 of biotinylated Nivolumab in the absence or presence of saturating concentrations of unlabeled PD-1_A mAb. Simultaneous binding of PD-1_A and Nivolumab revealed that the two mAbs did not interfere in their interactions with the receptor.

Example 4: High Affinity IgGs Against Immune Checkpoint Molecules Display T Cell Immunostimulatory Activity and Effector Functions Previous reports showed that CD3-positive primary resting cells in unfractionated hPBMCs can be induced to proliferate in vitro by using Staphylococcal Enterotoxin B (SEB) or Phytohaemagglutinin (PHA) and that this activity is modulated by CI (Maçon-Lemaître L, Immunology, 2005; Wang C, Cancer Immunol Res., 2014; Selby MJ, Plos One, 2016). We therefore used the lymphocyte proliferation assay described above to test whether the selected antibodies against LAG-3, PD-1 or PD-L1 were able to increase cell division. CFDA-SE stained lymphocytes were stimulated with PHA, and incubated in the absence or in the presence of the antibodies to induce antigen-specific T cells proliferation. In this assay, Nivolumab consistently led to a 50% increase in proliferative activity and the anti-PD-1 antibodies PD-1 A and PD-1_B were also able to efficiently stimulate T cell proliferation with the former one showing higher activity than the clinically active Nivolumab (FIG. 3). Similarly, all three antibodies against PD-L1 and one of the three LAG-3 antibodies also induced various degrees of proliferation. The ability to stimulate proliferation did not always correlate with the binding potency, suggesting that the different antibodies may have distinct modes of interactions with their targets.

Interestingly, the antibodies PD-1_A and PD-L1_A, which were the best activating antibodies on human lymphocytes confirmed this ability also on murine lymphocytes, thus suggesting that they are crossreactive with mouse PD-1 and PD-L1. We took advantage of MDA-MB-231 breast tumor cells expressing high levels of PD-L1 on their surface, to test the ability of the anti-PD-L1 and anti PD-1 antibodies to suppress the inhibitory action of the PD-1/PD-L1 interaction on the lymphocyte proliferation when the two cell types are co-cultured. As shown in FIG. 4, mAbs PD-L1_A and PD-1_A induced the proliferation of lymphocytes in a dose-dependent manner, whereas only a slight effect was detected on lymphocytes treated with mAbs PD-L1_B and PD-1_B. Also in this assay mAb PD-L1_A and PD-1_A displayed higher activity than Nivolumab, while no effects on the proliferation of lymphocytes were observed when PD-L1-negative MCF7 tumor cells were used. Interestingly, in some cases the ability to stimulate proliferation did not correlate with highest apparent affinity, such as in the case of mAbs LAG3_A and LAG3_C (FIG. 2 and Table in FIG. 2).

Three additional anti PD-L1 antibodies were identified and characterized with respect to PD-L1_A. The three antibodies, PD-L1_C, PD-L1_D and PD-L1_E were evaluated for their binding to human PBMCs, previously activated to induce PD-L1 surface expression. A higher percentage of lymphocytes was stained with three antibodies with respect to PD-L1_A (see FIG. 7).

Example 5: Effects of Novel Antibodies on the Production of Cytokines by Stimulated hPBMCs hPBMCs ($1 \times 10^6$ cells) were cultured and stimulated with 2,5 µg/ml PHA-L or 50 ng/ml Staphylococcal Enterotoxin B (SEB, Sigma-Aldrich) for 18, 42 and 66 h, in the absence or in the presence of the selected anti-LAG-3, anti-PD-L1 and anti-PD-1 mAbs (20 µg/ml) or of an isotype control antibody, used as negative control. Nivolumab was tested as a positive control in parallel assays, in the same conditions. The levels of IL-2 or IFNγ in cell culture supernatants were measured by ELISA assays (DuoSet ELISA, R&D Systems), according to the manufacturer's recommendations.

Immunomodulatory antibodies, such as Nivolumab and Ipilimumab, were shown to improve T cell effector functions and this property potentially increasing their clinical benefit (Maçon-Lemaître L, Immunology, 2005; Wang C, Cancer Immunol Res., 2014; Selby MJ, Plos One, 2016). We therefore tested five antibodies among those with the highest ability to induce T-cell proliferation (LAG-3_A, PD-1_A, PD-1_B, PD-L1_A, and PD-L1_B) in a cytokine secretion assay previously reported for the characterization of Nivolumab (Wang C, Cancer Immunol Res., 2014). As shown in FIG. 5, all the tested antibodies were able to increase secretion of both IL-2 and IFNγ by hPBMCs stimulated with either PHA or SEB. Cytokine secretion increased over time upon addition of the different antibodies to the cell culture mix. PD-1_1 mAb appeared to be consistently more potent than all other tested antibodies for its ability to stimulate secretion of both cytokines. Also in this assay, the newly identified antibodies compared favorably with Nivolumab, further supporting the conclusion that the Immunome Library that we generated is enriched in binders with good potential for being developed for clinical use.

Two of the additional anti PD-L1 antibodies (PD-L1_C and PD-L1_D) that were identified and characterized with respect to PD-L1_A, were also evaluated in the described cytokine secretion assay in comparison with Nivolumab. As shown in FIG. 8, all the tested antibodies were able to increase secretion of both IL-2 and IFNγ by hPBMCs stimulated with either PHA or SEB.

Example 6: In Vivo Antitumor Activity

Six-week old female BalBC mice (Envigo) were used for in vivo studies. Mice were implanted subcutaneously on the right flank with $2 \times 10^5$ cells (day 0), and then treated intraperitoneally with 200 μg of α-mPD-L1 (BioXcell, clone 10F.9G2), α-mPD-1 (BioXcell, clone RMP114), PD-1_A or PD-L1_A at day 3, 6, 10. Tumor growth was measured by caliper every 3-4 days using the formula LxW2/2 (L as the largest and W the smallest diameter of the tumor). Animals were sacrificed as soon as signs of distress or a tumor volume above 2000 mm$^3$ occurred.

The two antibodies PD-1_A and PD-L1_A, given their cross-reactivity with mouse PD-1 and PD-L1, were also tested in vivo on CT26 colon cancer model. Mice were implanted with CT-26 cells (day 0) and then treated with PD-1_A and PD-L1 antibodies (day 3, 6, 10). Two commercially available antibodies reacting against murine PD-1 and PD-L1 (α-mPD-1 and α-mPD-L1) and previously validated in vivo (ref) were used as positive controls. While the growth rate of tumors in untreated mice was very fast and uncontrolled, with majority of tumors reaching sizes of >650 mm$^3$ at day 21, a reduction in tumor volume was found in mice treated with PD-1_A (p=0.03). The activity of the cross-reactive anti-PD-1 antibody is comparable to that of the commercial antibody against murine PD-1. A trend of comparable activity was also observed for the two anti-PD-L1 antibodies (FIG. 6). Treated mice consistently show a dichotomy in the response to PD-1 and PD-L1 blockade with two distinct treatment outcomes, responders and non-responders mice as well described for this and other cancer models. Thus, the biological and functional activities of the two novel mAbs was also confirmed in a relevant in vivo model.

Experimental Summary

The present inventors tailored the phage display technology to allow rapid identification of large sets of antibodies recognizing several different IC. To this end live activated hPBMCs were chosen as selectors for the generation of an unbiased library of IC binders, the Immunome Library, from which scFvs specifically recognizing a given receptor could be pulled out by subsequent affinity selection cycles using recombinant proteins, or peptides, or other target-specific baits. The rationale for using hPBMCs as a starting point of the selection process was also to ensure the selection of antibodies capable of recognizing the native receptor with the correct post-translational modification as displayed by live human cells. Consistently with this working hypothesis, human IgG4 generated using the selected scFvs were able to recognize the cell displayed receptors with apparent affinity in the low nanomolar range and down to 0.1 nM. This binding affinity is equal or better than the binding affinity shown for clinically active checkpoint-specific antibodies and is superior to that of the anti-PD-1 mAb Nivolumab approved for the treatment of many types of cancer (Wang C, Cancer Immunol Res., 2014). To improve the efficiency of selection on hPBMCs we increased the level of expression of the target IC by anti-CD3 crosslinking of the T-cells.

To facilitate the identification of binders recognizing specific receptors we used a panel of ten recombinant proteins to further affinity select the Immunome Library. With the aim of developing a universal protocol for the selection of antibodies to cell surface displayed proteins we performed two subsequent cycles of selection on recombinant Fc-fusion proteins. This strategy represented a compromise between efficiency of selection and generation of IC-specific repertoires with significant diversity to allow for the identification of antibodies binding to different regions of the target IC and with different biological activities.

All selections achieved enrichment levels between 100 and 1000-fold with four of them (PD-1, 4-1BB, CD27 and OX40) reaching even higher enrichment. Comparative sequence analysis of the different selection cycles confirmed that in most selections (i.e.: seven out of nine) there was a significant improvement in clones enrichment after the second cycle (i.e.: at least ten fold), while selection on LAG3 and OX40 did not seem to improve beyond the second cycle.

Our results support the conclusion that the combined ex vivo in vitro selection approach used in the context of the present invention is more rapid and efficient than the one of combining selection on live cells and identification of specific binders by direct screening on the target of choice which we have previously adopted (Monaci P, Plos One, 2008). Overall of the sixteen IgGs with confirmed binding (five anti-LAG3, five anti-PD-L1 and six anti-PD-1), eleven displayed low nanomolar apparent affinity for their cognate receptor expressed on hPBMCs, and three of them (PD-L1_2, PD-1_1 and PD-1_2) had sub-nanomolar apparent affinity and compared well with that of Nivolumab. Among them at least 2-3 out of the 5 converted antibodies for each target were found to be highly specific for both recombinant purified targets and activated lymphocytes with no significant binding to untreated lymphocytes or Fc, and thus they were chosen for further biological and functional assays.

When tested for their ability to stimulate T-cell proliferation, six out of eight antibodies (LAG-3_A, PD-L1_A, PD-L1_B, PD-1_A and PD-1_B) showed biological activity that was improved in comparison to Nivolumab. PD-1_A also displayed significant activity in promoting T-cell proliferation in co-cultures with high PD-L1-expressing tumor cell line MDA-MB-231. In this assay, also the PD-L1_A mAb almost tripled T-cell proliferation, consistently with its ability to interfere with PD-L1/PD-1 interaction. The most active antibodies did not always correspond to those with the stronger binding, such as mAb LAG-3_A which has lower apparent affinity that mAb LAG-3_C in the binding to hPBMCs and yet it was able to stimulate T cell proliferation while the latter could not. These results also indirectly suggest that the selected antibodies recognize different epitopes on the target protein. We could demonstrate that some of the antibodies identified in this work can stimulate T cells to secrete IL2 and IFNγ. PD-1_1 mAb consistently showed the highest activity in stimulating cytokine secretion and extended the observation that some of the antibodies identified in this work display binding affinities and biological properties similar to the clinically validated Nivolumab. In fact, some of the new antibodies showed even higher activities as compared to Nivolumab when tested in Cell-based assays with co-cultures of lymphocytes with either APC or tumor cells. These assays may better represent the in vivo conditions as they reproduce not only the negative effect of the interaction between the receptors and their ligand (ie.: PD-1/PD-L1), but also other potential biological effects that the novel antibodies may be able to antagonise. This could explain why the novel anti-PD-1 and anti-PD-L1 antibodies show stronger effects on T cell proliferation and stimulation of cytokine secretion than those exerted by Nivolumab, whose activity may be principally dependent on inhibition of PD-1 and PD-L1 interaction. This hypothesis is also supported by the interesting finding that the novel anti-PD-1 antibody recognizes a different epitope from Nivolumab and thus it could act with a different mechanism of action. Indeed PD-1_A was able to crossreact with mouse lymphocytes in a similar fashion to PD-L1_A which differentiates PD-1_A from Nivolumab. Due to this property, these two novel antibodies were tested also in vivo on mice bearing CT26 colon carcinoma and found to efficiently control tumor growth.

Overall the data presented in this work support the conclusion that the selection procedure employed allows the generation of antibodies specifically recognizing their target receptor in its native conformation and with high affinity without need for further affinity maturation leading to antibodies specifically binding to checkpoint inhibitors with properties superior to prior art antibodies.

The invention claimed is:

1. An antagonistic antigen binding protein that specifically binds to PD-L1, wherein said antigen binding protein comprises
a combination of complementarity determining regions 1, 2 and 3 of the heavy chain (CDRH1, CDRH2, CDRH3) and complementarity determining regions 1, 2 and 3 of the light chain (CDRL1, CDRL2, CDRL3) selected from the group of combinations consisting of:
(a) a CDRH1 comprising the amino acid sequence of SEQ ID NO: 22;
a CDRL1 comprising the amino acid sequence of SEQ ID NO: 23;
a CDRH2 comprising the amino acid sequence of SEQ ID NO: 24;
a CDRL2 comprising the amino acid sequence of SEQ ID NO: 25;
a CDRH3 comprising the amino acid sequence of SEQ ID NO: 26 and
a CDRL3 comprising the amino acid sequence of SEQ ID NO: 27; or
(b) a CDRH1 comprising the amino acid sequence of SEQ ID NO: 31;
a CDRL1 comprising the amino acid sequence of SEQ ID NO: 32;
a CDRH2 comprising the amino acid sequence of SEQ ID NO: 33;
a CDRL2 comprising the amino acid sequence of SEQ ID NO: 34;
a CDRH3 comprising the amino acid sequence of SEQ ID NO: 35; and
a CDRL3 comprising the amino acid sequence of SEQ ID NO: 36; or
(c) a CDRH1 comprising the amino acid sequence of SEQ ID NO: 22;
a CDRL1 comprising the amino acid sequence of SEQ ID NO: 23;
a CDRH2 comprising the amino acid sequence of SEQ ID NO: 24;
a CDRL2 comprising the amino acid sequence of SEQ ID NO: 25;
a CDRH3 comprising the amino acid sequence of SEQ ID NO: 89; and
a CDRL3 comprising the amino acid sequence of SEQ ID NO: 27; or
(d) a CDRH1 comprising the amino acid sequence of SEQ ID NO: 22;
a CDRL1 comprising the amino acid sequence of SEQ ID NO: 23;
a CDRH2 comprising the amino acid sequence of SEQ ID NO: 24;
a CDRL2 comprising the amino acid sequence of SEQ ID NO: 25;
a CDRH3 comprising the amino acid sequence of SEQ ID NO: 98; and
a CDRL3 comprising the amino acid sequence of SEQ ID NO: 27; or
(e) a CDRH1 comprising the amino acid sequence of SEQ ID NO: 22:
a CDRL1 comprising the amino acid sequence of SEQ ID NO: 23;
a CDRH2 comprising the amino acid sequence of SEQ ID NO: 24;
a CDRL2 comprising the amino acid sequence of SEQ ID NO: 25;
a CDRH3 comprising the amino acid sequence of SEQ ID NO: 107; and
a CDRL3 comprising the amino acid sequence of SEQ ID NO: 27.

2. The antagonistic antigen binding protein of claim 1, wherein said antigen binding protein comprises:
(i) a heavy chain variable region having a sequence with at least 90% identity to SEQ ID NO: 20; and a light chain variable region having a sequence with at least 90% identity to SEQ ID NO: 21; or
(ii) a heavy chain variable region having a sequence with at least 90% identity to SEQ ID NO: 29; and a light chain variable region having a sequence with at least 90% identity to SEQ ID NO: 30; or
(iii) a heavy chain variable region having a sequence with at least 90% identity to SEQ ID NO: 83; and a light chain variable region having a sequence with at least 90% identity to SEQ ID NO: 84; or (iv) a heavy chain variable region having a sequence with at least 90% identity to SEQ ID NO: 92; and a light chain variable region having a sequence with at least 90% identity to SEQ ID NO: 93; or (v) a heavy chain variable region having a sequence with at least 90% identity to SEQ ID NO: 101; and a light chain variable region having a sequence with at least 90% identity to SEQ ID NO: 102.

3. The antagonistic antigen binding protein of claim 1, wherein the antigen binding protein is an antibody, an antibody-like protein or a fragment thereof.

4. The antagonistic antigen binding protein of claim 3, wherein the antibody is selected from the group consisting of a human antibody, a humanized antibody, chimeric antibody, a monoclonal antibody, a multispecific antibody, a recombinant antibody, an antigen-binding antibody fragment, a single chain antibody, a single chain variable fragment antibody, a diabody, a Fab fragment, an F(ab)2 fragment, an antibody mimetic, an IgG1 antibody, an IgG2 antibody, an IgG3 antibody, and an IgG4 antibody.

5. A pharmaceutical composition comprising at least one antagonistic antigen binding protein according to claim 1 and a pharmaceutically acceptable carrier.

6. The pharmaceutical composition of claim 5, which comprises at least one further active agent.

7. A nucleic acid encoding the antagonistic antigen binding protein of claim 1.

8. A recombinant expression vector comprising the nucleic acid molecule according to claim 7.

9. A host cell comprising the vector of claim 8.

10. A method of making an antagonistic antigen binding protein that specifically binds to PD-L1, comprising the step of preparing said antigen binding protein from the host cell of claim 9, and wherein the host cell expresses said antigen binding protein.

11. The antagonistic antigen binding protein produced by the method of claim 10.

12. A method of treating cancer and/or chronic infectious disease comprising administering to a subject in need thereof an effective amount of the antagonistic antigen binding protein of claim 1.

13. The method according to claim 12, wherein
(i) the cancer is selected from one or more of the group consisting of:
(a) Malignant neoplasms of lip, oral cavity and pharynx;
(b) Malignant neoplasms of digestive organs;
(c) Malignant neoplasms of respiratory and intrathoracic organs;
(d) Malignant neoplasms of bone and articular cartilage;
(e) Melanoma and other malignant neoplasms of skin;
(f) Malignant neoplasms of mesothelial and soft tissue;
(g) Malignant neoplasm of breast;
(h) Malignant neoplasms of female genital organs;
(i) Malignant neoplasms of male genital organs;
(j) Malignant neoplasms of urinary tract;
(k) Malignant neoplasms of eye, brain and other parts of central nervous system;
(l) Malignant neoplasms of thyroid and other endocrine glands; and
(m) Malignant neoplasms of lymphoid, hematopoietic and related tissue:
(ii) the chronic infectious disease is selected from one or more of the group consisting of:
hepatitis B virus (HBV), hepatitis C virus (HCV), human immunodeficiency virus (HIV), herpes simplex virus (HSV), human papilloma virus (HPV), Epstein Barr Virus (EBV), cytomegalovirus (CMV) and *Chlamydia*.

14. The method according to claim 13, comprising administering at least one further active agent to the subject in need thereof, and wherein the at least one further active agent and the antagonistic antigen binding protein are administered either simultaneously or sequentially or a combination thereof.

* * * * *

SEQUENCE LISTING

```
<160> NUMBER OF SEQ ID NOS: 108

<210> SEQ ID NO 1
<211> LENGTH: 255
<212> TYPE: PRT
<213> ORGANISM: Homo sapiens

<400> SEQUENCE: 1

Gln Val Gln Leu Gln Glu Ser Gly Pro Gly Val Val Lys Pro Ser Gly
1               5                   10                  15

Thr Leu Ser Leu Thr Cys Ala Ile Ser Gly Gly Ser Ile Gly Ser Gly
            20                  25                  30

Gly Ser Ile Arg Ser Thr Arg Trp Trp Ser Trp Val Arg Gln Ser Pro
        35                  40                  45

Gly Lys Gly Leu Glu Trp Ile Gly Glu Ile Tyr His Ser Gly Ser Thr
    50                  55                  60

Asn Tyr Asn Pro Ser Leu Lys Ser Arg Val Thr Ile Ser Leu Asp Lys
65                  70                  75                  80

Ser Arg Asn His Phe Ser Leu Arg Leu Asn Ser Val Thr Ala Ala Asp
                85                  90                  95

Thr Ala Val Tyr Tyr Cys Ala Arg Gln Asp Tyr Gly Asp Ser Gly Asp
            100                 105                 110

Trp Tyr Phe Asp Leu Trp Gly Lys Gly Thr Leu Val Thr Val Ser Ser
        115                 120                 125

Gly Gly Gly Gly Ser Gly Gly Gly Ser Gly Gly Gly Gly Ser Ala
    130                 135                 140

Gln Ala Val Leu Thr Gln Pro Ser Ser Val Ser Gly Ala Pro Gly Gln
145                 150                 155                 160

Arg Val Thr Ile Ser Cys Thr Gly Ser Ser Ser Asn Ile Gly Ala Gly
                165                 170                 175

Tyr Asp Val His Trp Tyr Gln Gln Leu Pro Gly Thr Ala Pro Lys Leu
            180                 185                 190

Leu Ile Tyr Gly Asn Asn Asn Arg Pro Ser Gly Val Pro Asp Arg Phe
        195                 200                 205

Ser Gly Ser Lys Ser Gly Thr Ser Ala Ser Leu Ala Ile Thr Gly Leu
    210                 215                 220

Gln Thr Glu Asp Glu Ala Asp Tyr Tyr Cys Gln Ser Tyr Asp Asn Ser
225                 230                 235                 240

Leu Ser Gly Glu Val Phe Gly Gly Gly Thr Lys Val Thr Val Leu
                245                 250                 255

<210> SEQ ID NO 2
<211> LENGTH: 128
<212> TYPE: PRT
<213> ORGANISM: Homo sapiens

<400> SEQUENCE: 2
```

```
Gln Val Gln Leu Gln Glu Ser Gly Pro Gly Val Lys Pro Ser Gly
1               5                   10                  15

Thr Leu Ser Leu Thr Cys Ala Ile Ser Gly Gly Ser Ile Gly Ser Gly
            20                  25                  30

Gly Ser Ile Arg Ser Thr Arg Trp Ser Trp Val Arg Gln Ser Pro
            35                  40                  45

Gly Lys Gly Leu Glu Trp Ile Gly Glu Ile Tyr His Ser Gly Ser Thr
50                  55                  60

Asn Tyr Asn Pro Ser Leu Lys Ser Arg Val Thr Ile Ser Leu Asp Lys
65                  70                  75                  80

Ser Arg Asn His Phe Ser Leu Arg Leu Asn Ser Val Thr Ala Ala Asp
                85                  90                  95

Thr Ala Val Tyr Tyr Cys Ala Arg Gln Asp Tyr Gly Asp Ser Gly Asp
            100                 105                 110

Trp Tyr Phe Asp Leu Trp Gly Lys Gly Thr Leu Val Thr Val Ser Ser
                115                 120                 125

<210> SEQ ID NO 3
<211> LENGTH: 112
<212> TYPE: PRT
<213> ORGANISM: Homo sapiens

<400> SEQUENCE: 3

Ala Gln Ala Val Leu Thr Gln Pro Ser Ser Val Ser Gly Ala Pro Gly
1               5                   10                  15

Gln Arg Val Thr Ile Ser Cys Thr Gly Ser Ser Ser Asn Ile Gly Ala
            20                  25                  30

Gly Tyr Asp Val His Trp Tyr Gln Gln Leu Pro Gly Thr Ala Pro Lys
            35                  40                  45

Leu Leu Ile Tyr Gly Asn Asn Asn Arg Pro Ser Gly Val Pro Asp Arg
50                  55                  60

Phe Ser Gly Ser Lys Ser Gly Thr Ser Ala Ser Leu Ala Ile Thr Gly
65                  70                  75                  80

Leu Gln Thr Glu Asp Glu Ala Asp Tyr Tyr Cys Gln Ser Tyr Asp Asn
                85                  90                  95

Ser Leu Ser Gly Glu Val Phe Gly Gly Thr Lys Val Thr Val Leu
            100                 105                 110

<210> SEQ ID NO 4
<211> LENGTH: 13
<212> TYPE: PRT
<213> ORGANISM: Homo sapiens

<400> SEQUENCE: 4

Gly Ser Gly Gly Ser Ile Arg Ser Thr Arg Trp Trp Ser
1               5                   10

<210> SEQ ID NO 5
<211> LENGTH: 14
<212> TYPE: PRT
<213> ORGANISM: Homo sapiens

<400> SEQUENCE: 5

Thr Gly Ser Ser Ser Asn Ile Gly Ala Gly Tyr Asp Val His
1               5                   10

<210> SEQ ID NO 6
<211> LENGTH: 16
<212> TYPE: PRT
```

<213> ORGANISM: Homo sapiens

<400> SEQUENCE: 6

Glu Ile Tyr His Ser Gly Ser Thr Asn Tyr Asn Pro Ser Leu Lys Ser
1               5                   10                  15

<210> SEQ ID NO 7
<211> LENGTH: 12
<212> TYPE: PRT
<213> ORGANISM: Homo sapiens

<400> SEQUENCE: 7

Leu Leu Ile Tyr Gly Asn Asn Asn Arg Pro Ser Gly
1               5                   10

<210> SEQ ID NO 8
<211> LENGTH: 13
<212> TYPE: PRT
<213> ORGANISM: Homo sapiens

<400> SEQUENCE: 8

Gln Asp Tyr Gly Asp Ser Gly Asp Trp Tyr Phe Asp Leu
1               5                   10

<210> SEQ ID NO 9
<211> LENGTH: 11
<212> TYPE: PRT
<213> ORGANISM: Homo sapiens

<400> SEQUENCE: 9

Gln Ser Tyr Asp Asn Ser Leu Ser Gly Glu Val
1               5                   10

<210> SEQ ID NO 10
<211> LENGTH: 248
<212> TYPE: PRT
<213> ORGANISM: Homo sapiens

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Phe Gly Ser Gly Ser Tyr Tyr Asp Leu Ala Tyr Trp Gly
            100                 105                 110

Gln Gly Thr Met Val Thr Val Ser Ser Gly Gly Gly Gly Ser Gly Gly
        115                 120                 125

Gly Gly Ser Gly Gly Gly Gly Ser Ala Asn Phe Met Leu Thr Gln Pro
    130                 135                 140

His Ser Val Ser Glu Ser Pro Gly Lys Thr Val Thr Ile Ser Cys Thr
145                 150                 155                 160

Gly Ser Ser Gly Ser Ile Ala Ser Asn Tyr Val Gln Trp Tyr Gln Gln

-continued

```
                        165                 170                 175
Arg Pro Gly Ser Ala Pro Thr Thr Val Ile Tyr Glu Asp Asn Gln Arg
            180                 185                 190

Pro Ser Gly Val Pro Asp Arg Phe Ser Gly Ser Ile Asp Ser Ser Ser
        195                 200                 205

Asn Ser Ala Ser Leu Thr Ile Ser Gly Leu Lys Thr Glu Asp Glu Ala
    210                 215                 220

Asp Tyr Tyr Cys Gln Ser Tyr Asp Ser Asn Asn His Trp Val Phe Gly
225                 230                 235                 240

Gly Gly Thr Lys Leu Thr Val Leu
                245

<210> SEQ ID NO 11
<211> LENGTH: 121
<212> TYPE: PRT
<213> ORGANISM: Homo sapiens

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Phe Gly Ser Gly Ser Tyr Tyr Asp Leu Asp Tyr Trp Gly
            100                 105                 110

Gln Gly Thr Met Val Thr Val Ser Ser
        115                 120

<210> SEQ ID NO 12
<211> LENGTH: 112
<212> TYPE: PRT
<213> ORGANISM: Homo sapiens

<400> SEQUENCE: 12

Ala Asn Phe Met Leu Thr Gln Pro His Ser Val Ser Glu Ser Pro Gly
1               5                   10                  15

Lys Thr Val Thr Ile Ser Cys Thr Gly Ser Ser Gly Ser Ile Ala Ser
            20                  25                  30

Asn Tyr Val Gln Trp Tyr Gln Gln Arg Pro Gly Ser Ala Pro Thr Thr
        35                  40                  45

Val Ile Tyr Glu Asp Asn Gln Arg Pro Ser Gly Val Pro Asp Arg Phe
    50                  55                  60

Ser Gly Ser Ile Asp Ser Ser Ser Asn Ser Ala Ser Leu Thr Ile Ser
65                  70                  75                  80

Gly Leu Lys Thr Glu Asp Glu Ala Asp Tyr Tyr Cys Gln Ser Tyr Asp
                85                  90                  95

Ser Asn Asn His Trp Val Phe Gly Gly Gly Thr Lys Leu Thr Val Leu
            100                 105                 110
```

```
<210> SEQ ID NO 13
<211> LENGTH: 6
<212> TYPE: PRT
<213> ORGANISM: Homo sapiens

<400> SEQUENCE: 13

Thr Ser Tyr Gly Ile Ser
1               5

<210> SEQ ID NO 14
<211> LENGTH: 13
<212> TYPE: PRT
<213> ORGANISM: Homo sapiens

<400> SEQUENCE: 14

Thr Gly Ser Ser Gly Ser Ile Ala Ser Asn Tyr Val Gln
1               5                   10

<210> SEQ ID NO 15
<211> LENGTH: 17
<212> TYPE: PRT
<213> ORGANISM: Homo sapiens

<400> SEQUENCE: 15

Trp Ile Ser Ala Tyr Asn Gly Asn Thr Asn Tyr Ala Gln Lys Leu Gln
1               5                   10                  15

Gly

<210> SEQ ID NO 16
<211> LENGTH: 12
<212> TYPE: PRT
<213> ORGANISM: Homo sapiens

<400> SEQUENCE: 16

Thr Val Ile Tyr Glu Asp Asn Gln Arg Pro Ser Gly
1               5                   10

<210> SEQ ID NO 17
<211> LENGTH: 12
<212> TYPE: PRT
<213> ORGANISM: Homo sapiens

<400> SEQUENCE: 17

Asp Phe Gly Ser Gly Ser Tyr Tyr Asp Leu Asp Tyr
1               5                   10

<210> SEQ ID NO 18
<211> LENGTH: 10
<212> TYPE: PRT
<213> ORGANISM: Homo sapiens

<400> SEQUENCE: 18

Gln Ser Tyr Asp Ser Asn Asn His Trp Val
1               5                   10

<210> SEQ ID NO 19
<211> LENGTH: 246
<212> TYPE: PRT
<213> ORGANISM: Homo sapiens

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                  20                  25                  30
Ala Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Lys Trp Glu Leu Val Asp Pro Tyr Asp Tyr Trp Gly Gln
                100                 105                 110

Gly Thr Met Val Thr Val Ser Ser Gly Gly Gly Ser Gly Gly Gly
                115                 120                 125

Gly Ser Gly Gly Gly Ser Ala Asn Phe Met Leu Thr Gln Pro His
            130                 135                 140

Ser Val Ser Glu Ser Pro Gly Lys Thr Ile Thr Ile Ser Cys Thr Arg
145                 150                 155                 160

Ser Ser Gly Ser Ile Ala Gly Asn Tyr Val Gln Trp Tyr Gln Gln Arg
                165                 170                 175

Pro Gly Ser Ala Pro Ile Ile Val Ile Tyr Glu Asp Asn Gln Arg Pro
                180                 185                 190

Ser Gly Val Pro Asp Arg Phe Ser Gly Ser Ile Asp Ser Ser Ser Asn
                195                 200                 205

Ser Ala Ser Leu Thr Ile Ser Arg Leu Lys Thr Glu Asp Glu Ala Asp
            210                 215                 220

Tyr Tyr Cys Gln Ser Tyr Glu Ala Ser Asn Val Val Phe Gly Gly Gly
225                 230                 235                 240

Thr Lys Leu Thr Val Leu
                245

<210> SEQ ID NO 20
<211> LENGTH: 120
<212> TYPE: PRT
<213> ORGANISM: Homo sapiens

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Lys Trp Glu Leu Val Asp Pro Tyr Asp Tyr Trp Gly Gln
                100                 105                 110

Gly Thr Met Val Thr Val Ser Ser
                115                 120

<210> SEQ ID NO 21
<211> LENGTH: 111
```

```
<212> TYPE: PRT
<213> ORGANISM: Homo sapiens

<400> SEQUENCE: 21

Ala Asn Phe Met Leu Thr Gln Pro His Ser Val Ser Glu Ser Pro Gly
1               5                   10                  15

Lys Thr Ile Thr Ile Ser Cys Thr Arg Ser Ser Gly Ser Ile Ala Gly
            20                  25                  30

Asn Tyr Val Gln Trp Tyr Gln Gln Arg Pro Gly Ser Ala Pro Ile Ile
        35                  40                  45

Val Ile Tyr Glu Asp Asn Gln Arg Pro Ser Gly Val Pro Asp Arg Phe
    50                  55                  60

Ser Gly Ser Ile Asp Ser Ser Asn Ser Ala Ser Leu Thr Ile Ser
65                  70                  75                  80

Arg Leu Lys Thr Glu Asp Glu Ala Asp Tyr Tyr Cys Gln Ser Tyr Glu
                85                  90                  95

Ala Ser Asn Val Val Phe Gly Gly Gly Thr Lys Leu Thr Val Leu
            100                 105                 110

<210> SEQ ID NO 22
<211> LENGTH: 5
<212> TYPE: PRT
<213> ORGANISM: Homo sapiens

<400> SEQUENCE: 22

Ser Tyr Ala Met Ser
1               5

<210> SEQ ID NO 23
<211> LENGTH: 13
<212> TYPE: PRT
<213> ORGANISM: Homo sapiens

<400> SEQUENCE: 23

Thr Arg Ser Ser Gly Ser Ile Ala Gly Asn Tyr Val Gln
1               5                   10

<210> SEQ ID NO 24
<211> LENGTH: 17
<212> TYPE: PRT
<213> ORGANISM: Homo sapiens

<400> SEQUENCE: 24

Ala Ile Ser Gly Ser Gly Gly Ser Thr Tyr Tyr Ala Asp Ser Val Lys
1               5                   10                  15

Gly

<210> SEQ ID NO 25
<211> LENGTH: 12
<212> TYPE: PRT
<213> ORGANISM: Homo sapiens

<400> SEQUENCE: 25

Ile Val Ile Tyr Glu Asp Asn Gln Arg Pro Ser Gly
1               5                   10

<210> SEQ ID NO 26
<211> LENGTH: 11
<212> TYPE: PRT
<213> ORGANISM: Homo sapiens

<400> SEQUENCE: 26
```

Thr Lys Trp Glu Leu Val Asp Pro Tyr Asp Tyr
1               5                   10

<210> SEQ ID NO 27
<211> LENGTH: 9
<212> TYPE: PRT
<213> ORGANISM: Homo sapiens

<400> SEQUENCE: 27

Gln Ser Tyr Glu Ala Ser Asn Val Val
1               5

<210> SEQ ID NO 28
<211> LENGTH: 247
<212> TYPE: PRT
<213> ORGANISM: Homo sapiens

<400> SEQUENCE: 28

Gln Val Gln Leu Val Gln Ser Gly Ala Glu Val Lys Lys Pro Gly Ser
1               5                   10                  15

Ser Val Glu Val Ser Cys Lys Val Ser Gly Asn Thr Val Ile Gly Tyr
            20                  25                  30

Ala Val Ser Trp Val Arg Gln Ala Pro Gly Gln Gly Pro Glu Trp Met
        35                  40                  45

Gly Arg Leu Ile Pro Ser Val Gly Leu Thr Asn Tyr Ala Gln Lys Phe
    50                  55                  60

Gln Asp Arg Leu Thr Phe Thr Ala Asp Thr Ser Thr Ser Thr Val Thr
65                  70                  75                  80

Met Ala Leu Ser Ser Leu Thr Ser Glu Asp Thr Ala Met Tyr Tyr Cys
                85                  90                  95

Ala Arg Asp Val Ser Pro Ala Val Pro Val Ser Gln Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Ala Gln Ser Val Leu Thr Gln Pro Pro
    130                 135                 140

Ser Val Ser Ala Ala Pro Gly Gln Lys Val Ile Ile Ser Cys Ser Gly
145                 150                 155                 160

Asp Ser Phe Asn Ile Gly Ser His Ser Val Ser Trp Tyr Lys Gln Leu
                165                 170                 175

Pro Gly Ser Ala Pro Lys Leu Leu Ile Tyr Glu Asn Asn Val Arg Pro
            180                 185                 190

Ser Gly Ile Pro Asp Arg Phe Ser Gly Ser Lys Ser Gly Thr Ser Ala
        195                 200                 205

Thr Leu Gly Ile Thr Gly Leu Gln Thr Arg Asp Glu Ala Asp Tyr Tyr
    210                 215                 220

Cys Gly Ala Trp Asp Ser Ser Leu Asn Gly His Trp Val Phe Gly Gly
225                 230                 235                 240

Gly Thr Gln Leu Thr Val Leu
                245

<210> SEQ ID NO 29
<211> LENGTH: 120
<212> TYPE: PRT
<213> ORGANISM: Homo sapiens

<400> SEQUENCE: 29

Gln Val Gln Leu Val Gln Ser Gly Ala Glu Val Lys Lys Pro Gly Ser
1               5                   10                  15

Ser Val Glu Val Ser Cys Lys Val Ser Gly Asn Thr Ile Gly Tyr
            20                  25                  30

Ala Val Ser Trp Val Arg Gln Ala Pro Gly Gln Gly Pro Glu Trp Met
        35                  40                  45

Gly Arg Leu Ile Pro Ser Val Gly Leu Thr Asn Tyr Ala Gln Lys Phe
    50                  55                  60

Gln Asp Arg Leu Thr Phe Thr Ala Asp Thr Ser Thr Ser Thr Val Thr
65              70                  75                  80

Met Ala Leu Ser Ser Leu Thr Ser Glu Asp Thr Ala Met Tyr Tyr Cys
            85                  90                  95

Ala Arg Asp Val Ser Pro Ala Val Pro Val Ser Gln Tyr Trp Gly Gln
            100                 105                 110

Gly Thr Leu Val Thr Val Ser Ser
            115                 120

<210> SEQ ID NO 30
<211> LENGTH: 112
<212> TYPE: PRT
<213> ORGANISM: Homo sapiens

<400> SEQUENCE: 30

Ala Gln Ser Val Leu Thr Gln Pro Pro Ser Val Ser Ala Ala Pro Gly
1               5                   10                  15

Gln Lys Val Ile Ile Ser Cys Ser Gly Asp Ser Phe Asn Ile Gly Ser
            20                  25                  30

His Ser Val Ser Trp Tyr Lys Gln Leu Pro Gly Ser Ala Pro Lys Leu
        35                  40                  45

Leu Ile Tyr Glu Asn Asn Val Arg Pro Ser Gly Ile Pro Asp Arg Phe
    50                  55                  60

Ser Gly Ser Lys Ser Gly Thr Ser Ala Thr Leu Gly Ile Thr Gly Leu
65              70                  75                  80

Gln Thr Arg Asp Glu Ala Asp Tyr Tyr Cys Gly Ala Trp Asp Ser Ser
            85                  90                  95

Leu Asn Gly His Trp Val Phe Gly Gly Thr Gln Leu Thr Val Leu
            100                 105                 110

<210> SEQ ID NO 31
<211> LENGTH: 5
<212> TYPE: PRT
<213> ORGANISM: Homo sapiens

<400> SEQUENCE: 31

Gly Tyr Ala Val Ser
1               5

<210> SEQ ID NO 32
<211> LENGTH: 13
<212> TYPE: PRT
<213> ORGANISM: Homo sapiens

<400> SEQUENCE: 32

Ser Gly Asp Ser Phe Asn Ile Gly Ser His Ser Val Ser
1               5                   10

<210> SEQ ID NO 33
<211> LENGTH: 17
<212> TYPE: PRT

<213> ORGANISM: Homo sapiens

<400> SEQUENCE: 33

Arg Leu Ile Pro Ser Val Gly Leu Thr Asn Tyr Ala Gln Lys Phe Gln
1               5                   10                  15
Asp

<210> SEQ ID NO 34
<211> LENGTH: 12
<212> TYPE: PRT
<213> ORGANISM: Homo sapiens

<400> SEQUENCE: 34

Leu Leu Ile Tyr Glu Asn Asn Val Arg Pro Ser Gly
1               5                   10

<210> SEQ ID NO 35
<211> LENGTH: 11
<212> TYPE: PRT
<213> ORGANISM: Homo sapiens

<400> SEQUENCE: 35

Asp Val Ser Pro Ala Val Pro Val Ser Gln Tyr
1               5                   10

<210> SEQ ID NO 36
<211> LENGTH: 12
<212> TYPE: PRT
<213> ORGANISM: Homo sapiens

<400> SEQUENCE: 36

Gly Ala Trp Asp Ser Ser Leu Asn Gly His Trp Val
1               5                   10

<210> SEQ ID NO 37
<211> LENGTH: 255
<212> TYPE: PRT
<213> ORGANISM: Homo sapiens

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Pro Leu Tyr Asp Ile Ser Ala Gly Phe Val Pro Ile
            100                 105                 110

Ser Tyr Tyr Leu Asp Tyr Trp Gly Gln Gly Thr Thr Val Thr Val Ser
        115                 120                 125

Ser Gly Gly Gly Gly Ser Gly Gly Gly Ser Gly Gly Gly Gly Ser
    130                 135                 140

Ala Gln Pro Val Leu Thr Gln Pro Pro Ser Ala Ser Gly Thr Pro Gly
145                 150                 155                 160

```
Gln Arg Val Thr Ile Ser Cys Ser Gly Ser Phe Ser Asn Ile Gly Ser
                165                 170                 175

Asn Tyr Val Phe Trp Tyr Gln Gln Leu Pro Gly Thr Ala Pro Lys Leu
            180                 185                 190

Leu Ile Ser Gly Asn Asn Gln Arg Pro Ser Gly Val Pro Asp Arg Phe
        195                 200                 205

Ser Gly Ser Lys Ser Gly Thr Ser Ala Ser Leu Ala Ile Ser Gly Leu
    210                 215                 220

Arg Ser Gln Asp Glu Ala Asp Tyr Tyr Cys Ala Thr Trp Asp Asp Ser
225                 230                 235                 240

Leu Arg Gly Trp Val Phe Gly Gly Gly Thr Lys Leu Thr Val Leu
            245                 250                 255

<210> SEQ ID NO 38
<211> LENGTH: 129
<212> TYPE: PRT
<213> ORGANISM: Homo sapiens

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Pro Leu Tyr Asp Ile Ser Ala Gly Phe Val Pro Ile
            100                 105                 110

Ser Tyr Tyr Leu Asp Tyr Trp Gly Gln Gly Thr Thr Val Thr Val Ser
        115                 120                 125

Ser

<210> SEQ ID NO 39
<211> LENGTH: 111
<212> TYPE: PRT
<213> ORGANISM: Homo sapiens

<400> SEQUENCE: 39

Ala Gln Pro Val Leu Thr Gln Pro Pro Ser Ala Ser Gly Thr Pro Gly
1               5                   10                  15

Gln Arg Val Thr Ile Ser Cys Ser Gly Ser Phe Ser Asn Ile Gly Ser
            20                  25                  30

Asn Tyr Val Phe Trp Tyr Gln Gln Leu Pro Gly Thr Ala Pro Lys Leu
        35                  40                  45

Leu Ile Ser Gly Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Gln Asp Glu Ala Asp Tyr Tyr Cys Ala Thr Trp Asp Asp Ser
                85                  90                  95
```

Leu Arg Gly Trp Val Phe Gly Gly Gly Thr Lys Leu Thr Val Leu
            100                 105                 110

<210> SEQ ID NO 40
<211> LENGTH: 5
<212> TYPE: PRT
<213> ORGANISM: Homo sapiens

<400> SEQUENCE: 40

Ser Tyr Ala Met Ser
1               5

<210> SEQ ID NO 41
<211> LENGTH: 13
<212> TYPE: PRT
<213> ORGANISM: Homo sapiens

<400> SEQUENCE: 41

Ser Gly Ser Phe Ser Asn Ile Gly Ser Asn Tyr Val Phe
1               5                   10

<210> SEQ ID NO 42
<211> LENGTH: 17
<212> TYPE: PRT
<213> ORGANISM: Homo sapiens

<400> SEQUENCE: 42

Ala Ile Ser Gly Ser Gly Gly Ser Thr Tyr Tyr Ala Asp Ser Val Lys
1               5                   10                  15

Gly

<210> SEQ ID NO 43
<211> LENGTH: 12
<212> TYPE: PRT
<213> ORGANISM: Homo sapiens

<400> SEQUENCE: 43

Leu Leu Ile Ser Gly Asn Asn Gln Arg Pro Ser Gly
1               5                   10

<210> SEQ ID NO 44
<211> LENGTH: 20
<212> TYPE: PRT
<213> ORGANISM: Homo sapiens

<400> SEQUENCE: 44

Asp Gly Pro Leu Tyr Asp Ile Ser Ala Gly Phe Val Pro Ile Ser Tyr
1               5                   10                  15

Tyr Leu Asp Tyr
            20

<210> SEQ ID NO 45
<211> LENGTH: 11
<212> TYPE: PRT
<213> ORGANISM: Homo sapiens

<400> SEQUENCE: 45

Ala Thr Trp Asp Asp Ser Leu Arg Gly Trp Val
1               5                   10

<210> SEQ ID NO 46
<211> LENGTH: 253
<212> TYPE: PRT
<213> ORGANISM: Homo sapiens

<400> SEQUENCE: 46

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ser Gly Ile Val Val Pro Ala Ala Ile Arg Pro Gly Tyr
            100                 105                 110

Gly Met Asp Val Trp Gly Arg Gly Thr Thr Val Thr Val Ser Ser Gly
        115                 120                 125

Gly Gly Gly Ser Gly Gly Gly Gly Ser Gly Gly Gly Gly Ser Ala Gln
130                 135                 140

Ala Val Leu Thr Gln Pro Ser Ser Val Ser Gly Ala Pro Gly Gln Arg
145                 150                 155                 160

Val Thr Ile Ser Cys Thr Gly Ser Ser Asn Ile Gly Ala Gly Tyr
            165                 170                 175

Asp Val His Trp Tyr Gln Gln Leu Pro Gly Thr Ala Pro Lys Leu Leu
        180                 185                 190

Ile Tyr Gly Asn Asn Asn Arg Pro Ser Gly Val Pro Asp Arg Phe Ser
        195                 200                 205

Gly Ser Lys Ser Gly Thr Ser Ala Ser Leu Ala Ile Thr Gly Leu Gln
    210                 215                 220

Pro Glu Asp Glu Ala Asp Tyr Tyr Cys Gln Ser Tyr Asp Phe Gly Leu
225                 230                 235                 240

Ser Arg Val Phe Gly Gly Gly Thr Lys Leu Thr Val Leu
                245                 250
```

<210> SEQ ID NO 47
<211> LENGTH: 127
<212> TYPE: PRT
<213> ORGANISM: Homo sapiens

<400> SEQUENCE: 47

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ser Gly Ile Val Val Pro Ala Ala Ile Arg Pro Gly Tyr
            100                 105                 110
```

```
Gly Met Asp Val Trp Gly Arg Gly Thr Thr Val Thr Val Ser Ser
        115                 120                 125
```

<210> SEQ ID NO 48
<211> LENGTH: 111
<212> TYPE: PRT
<213> ORGANISM: Homo sapiens

<400> SEQUENCE: 48

```
Ala Gln Ala Val Leu Thr Gln Pro Ser Ser Val Ser Gly Ala Pro Gly
1               5                   10                  15

Gln Arg Val Thr Ile Ser Cys Thr Gly Ser Ser Ser Asn Ile Gly Ala
            20                  25                  30

Gly Tyr Asp Val His Trp Tyr Gln Gln Leu Pro Gly Thr Ala Pro Lys
        35                  40                  45

Leu Leu Ile Tyr Gly Asn Asn Asn Arg Pro Ser Gly Val Pro Asp Arg
    50                  55                  60

Phe Ser Gly Ser Lys Ser Gly Thr Ser Ala Ser Leu Ala Ile Thr Gly
65                  70                  75                  80

Leu Gln Pro Glu Asp Glu Ala Asp Tyr Tyr Cys Gln Ser Tyr Asp Phe
                85                  90                  95

Gly Leu Ser Arg Val Phe Gly Gly Gly Thr Lys Leu Thr Val Leu
            100                 105                 110
```

<210> SEQ ID NO 49
<211> LENGTH: 5
<212> TYPE: PRT
<213> ORGANISM: Homo sapiens

<400> SEQUENCE: 49

```
Ser Tyr Ala Met Ser
1               5
```

<210> SEQ ID NO 50
<211> LENGTH: 14
<212> TYPE: PRT
<213> ORGANISM: Homo sapiens

<400> SEQUENCE: 50

```
Thr Gly Ser Ser Ser Asn Ile Gly Ala Gly Tyr Asp Val His
1               5                   10
```

<210> SEQ ID NO 51
<211> LENGTH: 17
<212> TYPE: PRT
<213> ORGANISM: Homo sapiens

<400> SEQUENCE: 51

```
Ala Ile Ser Gly Ser Gly Gly Ser Thr Tyr Tyr Ala Asp Ser Val Lys
1               5                   10                  15

Gly
```

<210> SEQ ID NO 52
<211> LENGTH: 12
<212> TYPE: PRT
<213> ORGANISM: Homo sapiens

<400> SEQUENCE: 52

```
Leu Leu Ile Tyr Gly Asn Asn Asn Arg Pro Ser Gly
1               5                   10
```

```
<210> SEQ ID NO 53
<211> LENGTH: 18
<212> TYPE: PRT
<213> ORGANISM: Homo sapiens

<400> SEQUENCE: 53

Ser Gly Ile Val Val Pro Ala Ala Ile Arg Pro Gly Tyr Gly Met
1               5                   10                  15
Asp Val

<210> SEQ ID NO 54
<211> LENGTH: 10
<212> TYPE: PRT
<213> ORGANISM: Homo sapiens

<400> SEQUENCE: 54

Gln Ser Tyr Asp Phe Gly Leu Ser Arg Val
1               5                   10

<210> SEQ ID NO 55
<211> LENGTH: 250
<212> TYPE: PRT
<213> ORGANISM: Homo sapiens

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Pro Thr Met Tyr Ser Ser Gly Trp Tyr Tyr Phe Asp Phe
        100                 105                 110

Trp Gly Arg Gly Thr Met Val Thr Val Ser Ser Gly Gly Gly Gly Ser
    115                 120                 125

Gly Gly Gly Gly Ser Gly Gly Gly Ser Ala Leu Ser Tyr Val Leu
        130                 135                 140

Thr Gln Pro Pro Ser Val Ser Glu Ala Pro Arg Gln Arg Val Thr Ile
145                 150                 155                 160

Ser Cys Ser Gly Ser Ser Ser Asn Ile Gly Asn Asn Ala Val Asn Trp
            165                 170                 175

Tyr Gln Gln Leu Pro Gly Lys Ala Pro Lys Leu Leu Ile Tyr Tyr Asp
        180                 185                 190

Asp Leu Leu Pro Ser Gly Val Ser Asp Arg Phe Ser Gly Ser Lys Ser
    195                 200                 205

Gly Thr Ser Ala Ser Leu Ala Ile Ser Gly Leu Gln Ser Glu Asp Glu
210                 215                 220

Ala Asp Tyr Tyr Cys Ala Thr Trp Asp Ser Leu Asn Gly Gln Val
225                 230                 235                 240

Phe Gly Thr Gly Thr Lys Leu Thr Val Leu
            245                 250
```

<210> SEQ ID NO 56
<211> LENGTH: 123
<212> TYPE: PRT
<213> ORGANISM: Homo sapiens

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Thr Met Tyr Ser Ser Gly Tyr Tyr Phe Asp Phe
            100                 105                 110

Trp Gly Arg Gly Thr Met Val Thr Val Ser Ser
        115                 120

<210> SEQ ID NO 57
<211> LENGTH: 112
<212> TYPE: PRT
<213> ORGANISM: Homo sapiens

<400> SEQUENCE: 57

Ala Leu Ser Tyr Val Leu Thr Gln Pro Pro Ser Val Ser Glu Ala Pro
1               5                   10                  15

Arg Gln Arg Val Thr Ile Ser Cys Ser Gly Ser Ser Asn Ile Gly
            20                  25                  30

Asn Asn Ala Val Asn Trp Tyr Gln Gln Leu Pro Gly Lys Ala Pro Lys
        35                  40                  45

Leu Leu Ile Tyr Tyr Asp Asp Leu Leu Pro Ser Gly Val Ser Asp Arg
    50                  55                  60

Phe Ser Gly Ser Lys Ser Gly Thr Ser Ala Ser Leu Ala Ile Ser Gly
65                  70                  75                  80

Leu Gln Ser Glu Asp Glu Ala Asp Tyr Tyr Cys Ala Thr Trp Asp Asp
                85                  90                  95

Ser Leu Asn Gly Gln Val Phe Gly Thr Gly Thr Lys Leu Thr Val Leu
            100                 105                 110

<210> SEQ ID NO 58
<211> LENGTH: 5
<212> TYPE: PRT
<213> ORGANISM: Homo sapiens

<400> SEQUENCE: 58

Ser Tyr Ala Met Ser
1               5

<210> SEQ ID NO 59
<211> LENGTH: 13
<212> TYPE: PRT
<213> ORGANISM: Homo sapiens

```
<400> SEQUENCE: 59

Ser Gly Ser Ser Ser Asn Ile Gly Asn Asn Ala Val Asn
1               5                   10

<210> SEQ ID NO 60
<211> LENGTH: 17
<212> TYPE: PRT
<213> ORGANISM: Homo sapiens

<400> SEQUENCE: 60

Ala Ile Ser Gly Ser Gly Gly Ser Thr Tyr Tyr Ala Asp Ser Val Lys
1               5                   10                  15

Gly

<210> SEQ ID NO 61
<211> LENGTH: 12
<212> TYPE: PRT
<213> ORGANISM: Homo sapiens

<400> SEQUENCE: 61

Leu Leu Ile Tyr Tyr Asp Asp Leu Leu Pro Ser Gly
1               5                   10

<210> SEQ ID NO 62
<211> LENGTH: 14
<212> TYPE: PRT
<213> ORGANISM: Homo sapiens

<400> SEQUENCE: 62

Asp Pro Thr Met Tyr Ser Ser Gly Trp Tyr Tyr Phe Asp Phe
1               5                   10

<210> SEQ ID NO 63
<211> LENGTH: 11
<212> TYPE: PRT
<213> ORGANISM: Homo sapiens

<400> SEQUENCE: 63

Ala Thr Trp Asp Asp Ser Leu Asn Gly Gln Val
1               5                   10

<210> SEQ ID NO 64
<211> LENGTH: 247
<212> TYPE: PRT
<213> ORGANISM: Homo sapiens

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Phe Tyr Tyr Asp Ser Ser Val Val Asp Tyr Trp Gly
            100                 105                 110
```

```
Arg Gly Thr Thr Val Thr Val Ser Ser Gly Gly Gly Ser Gly Gly
            115                 120                 125

Gly Gly Ser Gly Gly Gly Ser Ala Leu Asp Ile Gln Met Thr Gln
    130                 135                 140

Ser Pro Pro Thr Leu Ser Ala Ser Val Gly Asp Arg Val Thr Ile Thr
145                 150                 155                 160

Cys Arg Ala Ser Gln Arg Ile Asn Ser Trp Leu Ala Trp Tyr Lys Gln
                165                 170                 175

Gln Pro Gly Glu Ala Pro Lys Leu Leu Ile Tyr Lys Ala Ser Asn Leu
            180                 185                 190

Gln Ser Glu Val Pro Gln Arg Phe Ser Gly Ser Glu Ser Gly Thr Glu
            195                 200                 205

Phe Thr Leu Thr Ile Ser Asp Leu Gln Pro Asp Phe Ala Thr Tyr
            210                 215                 220

Tyr Cys Gln Gln Tyr Ser Glu Thr Pro Leu Thr Phe Gly Gly Gly Thr
225                 230                 235                 240

Arg Leu Glu Ile Lys Arg Ala
            245
```

<210> SEQ ID NO 65
<211> LENGTH: 121
<212> TYPE: PRT
<213> ORGANISM: Homo sapiens

<400> SEQUENCE: 65

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Phe Tyr Tyr Asp Ser Ser Val Val Asp Tyr Trp Gly
            100                 105                 110

Arg Gly Thr Thr Val Thr Val Ser Ser
        115                 120
```

<210> SEQ ID NO 66
<211> LENGTH: 111
<212> TYPE: PRT
<213> ORGANISM: Homo sapiens

<400> SEQUENCE: 66

```
Ala Leu Asp Ile Gln Met Thr Gln Ser Pro Pro Thr Leu Ser Ala Ser
1               5                   10                  15

Val Gly Asp Arg Val Thr Ile Thr Cys Arg Ala Ser Gln Arg Ile Asn
            20                  25                  30

Ser Trp Leu Ala Trp Tyr Lys Gln Gln Pro Gly Glu Ala Pro Lys Leu
        35                  40                  45

Leu Ile Tyr Lys Ala Ser Asn Leu Gln Ser Glu Val Pro Gln Arg Phe
    50                  55                  60
```

-continued

```
Ser Gly Ser Glu Ser Gly Thr Glu Phe Thr Leu Thr Ile Ser Asp Leu
65                  70                  75                  80

Gln Pro Asp Asp Phe Ala Thr Tyr Tyr Cys Gln Gln Tyr Ser Glu Thr
                85                  90                  95

Pro Leu Thr Phe Gly Gly Gly Thr Arg Leu Glu Ile Lys Arg Ala
            100                 105                 110
```

<210> SEQ ID NO 67
<211> LENGTH: 5
<212> TYPE: PRT
<213> ORGANISM: Homo sapiens

<400> SEQUENCE: 67

```
Ser Tyr Ala Met Ser
1               5
```

<210> SEQ ID NO 68
<211> LENGTH: 11
<212> TYPE: PRT
<213> ORGANISM: Homo sapiens

<400> SEQUENCE: 68

```
Arg Ala Ser Gln Arg Ile Asn Ser Trp Leu Ala
1               5                   10
```

<210> SEQ ID NO 69
<211> LENGTH: 17
<212> TYPE: PRT
<213> ORGANISM: Homo sapiens

<400> SEQUENCE: 69

```
Ala Ile Ser Gly Ser Gly Gly Ser Thr Tyr Tyr Ala Asp Ser Val Lys
1               5                   10                  15

Gly
```

<210> SEQ ID NO 70
<211> LENGTH: 12
<212> TYPE: PRT
<213> ORGANISM: Homo sapiens

<400> SEQUENCE: 70

```
Leu Leu Ile Tyr Lys Ala Ser Asn Leu Gln Ser Glu
1               5                   10
```

<210> SEQ ID NO 71
<211> LENGTH: 12
<212> TYPE: PRT
<213> ORGANISM: Homo sapiens

<400> SEQUENCE: 71

```
Asp Leu Phe Tyr Tyr Asp Ser Ser Val Val Asp Tyr
1               5                   10
```

<210> SEQ ID NO 72
<211> LENGTH: 9
<212> TYPE: PRT
<213> ORGANISM: Homo sapiens

<400> SEQUENCE: 72

```
Gln Gln Tyr Ser Glu Thr Pro Leu Thr
1               5
```

```
<210> SEQ ID NO 73
<211> LENGTH: 244
<212> TYPE: PRT
<213> ORGANISM: Homo sapiens

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Gly Gly Thr Met Phe Asp Tyr Trp Gly Arg Gly Thr
            100                 105                 110

Leu Val Thr Val Ser Ser Gly Gly Gly Ser Gly Gly Gly Gly Ser
            115                 120                 125

Gly Gly Gly Gly Ser Ala Gln Ser Val Val Thr Gln Pro Pro Ser Thr
130                 135                 140

Ser Ala Thr Pro Gly Gln Arg Val Thr Ile Ser Cys Ser Gly Ser Thr
145                 150                 155                 160

Ser Asn Ile Gly Gly Asn Thr Val Asn Trp Tyr Gln Gln Leu Pro Gly
                165                 170                 175

Thr Ala Pro Lys Leu Leu Ile Tyr Ser Asn Asn Gln Arg Pro Ser Gly
            180                 185                 190

Val Pro Asp Arg Phe Ser Ala Ser Lys Ser Gly Thr Ser Ala Ser Leu
        195                 200                 205

Ala Ile Ser Gly Leu Gln Ser Glu Asp Glu Ala Asp Tyr Tyr Cys Ala
    210                 215                 220

Ser Trp Asp Asp Ser Leu Asn Gly Trp Leu Phe Gly Gly Gly Thr Lys
225                 230                 235                 240

Leu Thr Val Leu

<210> SEQ ID NO 74
<211> LENGTH: 118
<212> TYPE: PRT
<213> ORGANISM: Homo sapiens

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Gly Ala Gly Gly Thr Met Phe Asp Tyr Trp Gly Arg Gly Thr
            100                 105                 110

Leu Val Thr Val Ser Ser
        115
```

<210> SEQ ID NO 75
<211> LENGTH: 111
<212> TYPE: PRT
<213> ORGANISM: Homo sapiens

<400> SEQUENCE: 75

```
Ala Gln Ser Val Val Thr Gln Pro Pro Ser Thr Ser Ala Thr Pro Gly
1               5                   10                  15

Gln Arg Val Thr Ile Ser Cys Ser Gly Ser Thr Ser Asn Ile Gly Gly
            20                  25                  30

Asn Thr Val Asn Trp Tyr Gln Gln Leu Pro Gly Thr Ala Pro Lys Leu
        35                  40                  45

Leu Ile Tyr Ser Asn Asn Gln Arg Pro Ser Gly Val Pro Asp Arg Phe
    50                  55                  60

Ser Ala Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ser Trp Asp Ser Ser
                85                  90                  95

Leu Asn Gly Trp Leu Phe Gly Gly Gly Thr Lys Leu Thr Val Leu
            100                 105                 110
```

<210> SEQ ID NO 76
<211> LENGTH: 5
<212> TYPE: PRT
<213> ORGANISM: Homo sapiens

<400> SEQUENCE: 76

```
Ser Tyr Ala Met Ser
1               5
```

<210> SEQ ID NO 77
<211> LENGTH: 13
<212> TYPE: PRT
<213> ORGANISM: Homo sapiens

<400> SEQUENCE: 77

```
Ser Gly Ser Thr Ser Asn Ile Gly Gly Asn Thr Val Asn
1               5                   10
```

<210> SEQ ID NO 78
<211> LENGTH: 17
<212> TYPE: PRT
<213> ORGANISM: Homo sapiens

<400> SEQUENCE: 78

```
Ala Ile Ser Gly Ser Gly Gly Ser Thr Tyr Tyr Ala Asp Ser Val Lys
1               5                   10                  15

Gly
```

<210> SEQ ID NO 79
<211> LENGTH: 12
<212> TYPE: PRT
<213> ORGANISM: Homo sapiens

<400> SEQUENCE: 79

```
Leu Leu Ile Tyr Ser Asn Asn Gln Arg Pro Ser Gly
1               5                   10
```

<210> SEQ ID NO 80
<211> LENGTH: 9
<212> TYPE: PRT
<213> ORGANISM: Homo sapiens

<400> SEQUENCE: 80

```
Gly Ala Gly Gly Thr Met Phe Asp Tyr
1               5
```

<210> SEQ ID NO 81
<211> LENGTH: 11
<212> TYPE: PRT
<213> ORGANISM: Homo sapiens

<400> SEQUENCE: 81

```
Ala Ser Trp Asp Asp Ser Leu Asn Gly Trp Leu
1               5                   10
```

<210> SEQ ID NO 82
<211> LENGTH: 246
<212> TYPE: PRT
<213> ORGANISM: Homo sapiens

<400> SEQUENCE: 82

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Lys Trp Glu Leu Val Asp Pro Phe Gly Tyr Trp Gly Gln
            100                 105                 110

Gly Thr Met Val Thr Val Ser Ser Gly Gly Gly Gly Ser Gly Gly Gly
        115                 120                 125

Gly Ser Gly Gly Gly Gly Ser Ala Asn Phe Met Leu Thr Gln Pro His
    130                 135                 140

Ser Val Ser Glu Ser Pro Gly Lys Thr Ile Thr Ile Ser Cys Thr Arg
145                 150                 155                 160

Ser Ser Gly Ser Ile Ala Gly Asn Tyr Val Gln Trp Tyr Gln Gln Arg
                165                 170                 175

Pro Gly Ser Ala Pro Ile Ile Val Ile Tyr Glu Asp Asn Gln Arg Pro
            180                 185                 190

Ser Gly Val Pro Asp Arg Phe Ser Gly Ser Ile Asp Ser Ser Ser Asn
        195                 200                 205

Ser Ala Ser Leu Thr Ile Ser Arg Leu Lys Thr Glu Asp Glu Ala Asp
    210                 215                 220

Tyr Tyr Cys Gln Ser Tyr Glu Ala Ser Asn Val Val Phe Gly Gly Gly
225                 230                 235                 240

Thr Lys Leu Thr Val Leu
```

<210> SEQ ID NO 83
<211> LENGTH: 120
<212> TYPE: PRT
<213> ORGANISM: Homo sapiens

<400> SEQUENCE: 83

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Lys Trp Glu Leu Val Asp Pro Phe Gly Tyr Trp Gly Gln
            100                 105                 110

Gly Thr Met Val Thr Val Ser Ser
        115                 120

<210> SEQ ID NO 84
<211> LENGTH: 111
<212> TYPE: PRT
<213> ORGANISM: Homo sapiens

<400> SEQUENCE: 84

Ala Asn Phe Met Leu Thr Gln Pro His Ser Val Ser Glu Ser Pro Gly
1               5                   10                  15

Lys Thr Ile Thr Ile Ser Cys Thr Arg Ser Ser Gly Ser Ile Ala Gly
            20                  25                  30

Asn Tyr Val Gln Trp Tyr Gln Gln Arg Pro Gly Ser Ala Pro Ile Ile
        35                  40                  45

Val Ile Tyr Glu Asp Asn Gln Arg Pro Ser Gly Val Pro Asp Arg Phe
    50                  55                  60

Ser Gly Ser Ile Asp Ser Ser Asn Ser Ala Ser Leu Thr Ile Ser
65                  70                  75                  80

Arg Leu Lys Thr Glu Asp Glu Ala Asp Tyr Tyr Cys Gln Ser Tyr Glu
                85                  90                  95

Ala Ser Asn Val Val Phe Gly Gly Gly Thr Lys Leu Thr Val Leu
            100                 105                 110

<210> SEQ ID NO 85
<211> LENGTH: 5
<212> TYPE: PRT
<213> ORGANISM: Homo sapiens

<400> SEQUENCE: 85

Ser Tyr Ala Met Ser
1               5

<210> SEQ ID NO 86
<211> LENGTH: 13
<212> TYPE: PRT
<213> ORGANISM: Homo sapiens

<400> SEQUENCE: 86

Thr Arg Ser Ser Gly Ser Ile Ala Gly Asn Tyr Val Gln
1               5                   10

<210> SEQ ID NO 87
<211> LENGTH: 17
<212> TYPE: PRT
<213> ORGANISM: Homo sapiens

<400> SEQUENCE: 87

Ala Ile Ser Gly Ser Gly Gly Ser Thr Tyr Tyr Ala Asp Ser Val Lys
1               5                   10                  15

Gly

<210> SEQ ID NO 88
<211> LENGTH: 12
<212> TYPE: PRT
<213> ORGANISM: Homo sapiens

<400> SEQUENCE: 88

Ile Val Ile Tyr Glu Asp Asn Gln Arg Pro Ser Gly
1               5                   10

<210> SEQ ID NO 89
<211> LENGTH: 11
<212> TYPE: PRT
<213> ORGANISM: Homo sapiens

<400> SEQUENCE: 89

Ser Lys Trp Glu Leu Val Asp Pro Phe Gly Tyr
1               5                   10

<210> SEQ ID NO 90
<211> LENGTH: 9
<212> TYPE: PRT
<213> ORGANISM: Homo sapiens

<400> SEQUENCE: 90

Gln Ser Tyr Glu Ala Ser Asn Val Val
1               5

<210> SEQ ID NO 91
<211> LENGTH: 246
<212> TYPE: PRT
<213> ORGANISM: Homo sapiens

<400> SEQUENCE: 91

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Lys Trp Glu Leu Val Asp Pro Tyr Gly Asn Trp Gly Gln

```
                100                 105                 110
Gly Thr Met Val Thr Val Ser Ser Gly Gly Gly Ser Gly Gly Gly
            115                 120                 125

Gly Ser Gly Gly Gly Ser Ala Asn Phe Met Leu Thr Gln Pro His
            130                 135                 140

Ser Val Ser Glu Ser Pro Gly Lys Thr Ile Thr Ile Ser Cys Thr Arg
145                 150                 155                 160

Ser Ser Gly Ser Ile Ala Gly Asn Tyr Val Gln Trp Tyr Gln Arg
            165                 170                 175

Pro Gly Ser Ala Pro Ile Ile Val Ile Tyr Glu Asp Asn Gln Arg Pro
                180                 185                 190

Ser Gly Val Pro Asp Arg Phe Ser Gly Ser Ile Asp Ser Ser Ser Asn
            195                 200                 205

Ser Ala Ser Leu Thr Ile Ser Arg Leu Lys Thr Glu Asp Glu Ala Asp
            210                 215                 220

Tyr Tyr Cys Gln Ser Tyr Glu Ala Ser Asn Val Val Phe Gly Gly Gly
225                 230                 235                 240

Thr Lys Leu Thr Val Leu
                245

<210> SEQ ID NO 92
<211> LENGTH: 120
<212> TYPE: PRT
<213> ORGANISM: Homo sapiens

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Lys Trp Glu Leu Val Asp Pro Tyr Gly Asn Trp Gly Gln
            100                 105                 110

Gly Thr Met Val Thr Val Ser Ser
        115                 120

<210> SEQ ID NO 93
<211> LENGTH: 111
<212> TYPE: PRT
<213> ORGANISM: Homo sapiens

<400> SEQUENCE: 93

Ala Asn Phe Met Leu Thr Gln Pro His Ser Val Ser Glu Ser Pro Gly
1               5                   10                  15

Lys Thr Ile Thr Ile Ser Cys Thr Arg Ser Ser Gly Ser Ile Ala Gly
            20                  25                  30

Asn Tyr Val Gln Trp Tyr Gln Gln Arg Pro Gly Ser Ala Pro Ile Ile
        35                  40                  45

Val Ile Tyr Glu Asp Asn Gln Arg Pro Ser Gly Val Pro Asp Arg Phe
```

-continued

```
                  50                  55                  60
Ser Gly Ser Ile Asp Ser Ser Asn Ser Ala Ser Leu Thr Ile Ser
 65                  70                  75                  80

Arg Leu Lys Thr Glu Asp Glu Ala Asp Tyr Tyr Cys Gln Ser Tyr Glu
                 85                  90                  95

Ala Ser Asn Val Val Phe Gly Gly Gly Thr Lys Leu Thr Val Leu
            100                 105                 110
```

<210> SEQ ID NO 94
<211> LENGTH: 5
<212> TYPE: PRT
<213> ORGANISM: Homo sapiens

<400> SEQUENCE: 94

```
Ser Tyr Ala Met Ser
 1               5
```

<210> SEQ ID NO 95
<211> LENGTH: 13
<212> TYPE: PRT
<213> ORGANISM: Homo sapiens

<400> SEQUENCE: 95

```
Thr Arg Ser Ser Gly Ser Ile Ala Gly Asn Tyr Val Gln
 1               5                  10
```

<210> SEQ ID NO 96
<211> LENGTH: 17
<212> TYPE: PRT
<213> ORGANISM: Homo sapiens

<400> SEQUENCE: 96

```
Ala Ile Ser Gly Ser Gly Gly Ser Thr Tyr Tyr Ala Asp Ser Val Lys
 1               5                  10                  15

Gly
```

<210> SEQ ID NO 97
<211> LENGTH: 12
<212> TYPE: PRT
<213> ORGANISM: Homo sapiens

<400> SEQUENCE: 97

```
Ile Val Ile Tyr Glu Asp Asn Gln Arg Pro Ser Gly
 1               5                  10
```

<210> SEQ ID NO 98
<211> LENGTH: 11
<212> TYPE: PRT
<213> ORGANISM: Homo sapiens

<400> SEQUENCE: 98

```
Ser Lys Trp Glu Leu Val Asp Pro Tyr Gly Asn
 1               5                  10
```

<210> SEQ ID NO 99
<211> LENGTH: 9
<212> TYPE: PRT
<213> ORGANISM: Homo sapiens

<400> SEQUENCE: 99

```
Gln Ser Tyr Glu Ala Ser Asn Val Val
 1               5
```

<210> SEQ ID NO 100
<211> LENGTH: 246
<212> TYPE: PRT
<213> ORGANISM: Homo sapiens

<400> SEQUENCE: 100

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Lys Trp Glu Leu Val Asp Pro Tyr Gly Tyr Trp Gly Gln
            100                 105                 110

Gly Thr Met Val Thr Val Ser Ser Gly Gly Gly Ser Gly Gly Gly
        115                 120                 125

Gly Ser Gly Gly Gly Ser Ala Asn Phe Met Leu Thr Gln Pro His
130                 135                 140

Ser Val Ser Glu Ser Pro Gly Lys Thr Ile Thr Ile Ser Cys Thr Arg
145                 150                 155                 160

Ser Ser Gly Ser Ile Ala Gly Asn Tyr Val Gln Trp Tyr Gln Gln Arg
                165                 170                 175

Pro Gly Ser Ala Pro Ile Ile Val Ile Tyr Glu Asp Asn Gln Arg Pro
            180                 185                 190

Ser Gly Val Pro Asp Arg Phe Ser Gly Ser Ile Asp Ser Ser Ser Asn
        195                 200                 205

Ser Ala Ser Leu Thr Ile Ser Arg Leu Lys Thr Glu Asp Glu Ala Asp
    210                 215                 220

Tyr Tyr Cys Gln Ser Tyr Glu Ala Ser Asn Val Val Phe Gly Gly Gly
225                 230                 235                 240

Thr Lys Leu Thr Val Leu
                245

<210> SEQ ID NO 101
<211> LENGTH: 120
<212> TYPE: PRT
<213> ORGANISM: Homo sapiens

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Lys Trp Glu Leu Val Asp Pro Tyr Gly Tyr Trp Gly Gln
            100                 105                 110

Gly Thr Met Val Thr Val Ser Ser
        115                 120

<210> SEQ ID NO 102
<211> LENGTH: 111
<212> TYPE: PRT
<213> ORGANISM: Homo sapiens

<400> SEQUENCE: 102

Ala Asn Phe Met Leu Thr Gln Pro His Ser Val Ser Glu Ser Pro Gly
1               5                   10                  15

Lys Thr Ile Thr Ile Ser Cys Thr Arg Ser Ser Gly Ser Ile Ala Gly
            20                  25                  30

Asn Tyr Val Gln Trp Tyr Gln Gln Arg Pro Gly Ser Ala Pro Ile Ile
        35                  40                  45

Val Ile Tyr Glu Asp Asn Gln Arg Pro Ser Gly Val Pro Asp Arg Phe
    50                  55                  60

Ser Gly Ser Ile Asp Ser Ser Asn Ser Ala Ser Leu Thr Ile Ser
65                  70                  75                  80

Arg Leu Lys Thr Glu Asp Glu Ala Asp Tyr Tyr Cys Gln Ser Tyr Glu
                85                  90                  95

Ala Ser Asn Val Val Phe Gly Gly Gly Thr Lys Leu Thr Val Leu
            100                 105                 110

<210> SEQ ID NO 103
<211> LENGTH: 5
<212> TYPE: PRT
<213> ORGANISM: Homo sapiens

<400> SEQUENCE: 103

Ser Tyr Ala Met Ser
1               5

<210> SEQ ID NO 104
<211> LENGTH: 13
<212> TYPE: PRT
<213> ORGANISM: Homo sapiens

<400> SEQUENCE: 104

Thr Arg Ser Ser Gly Ser Ile Ala Gly Asn Tyr Val Gln
1               5                   10

<210> SEQ ID NO 105
<211> LENGTH: 17
<212> TYPE: PRT
<213> ORGANISM: Homo sapiens

<400> SEQUENCE: 105

Ala Ile Ser Gly Ser Gly Gly Ser Thr Tyr Tyr Ala Asp Ser Val Lys
1               5                   10                  15

Gly

<210> SEQ ID NO 106
<211> LENGTH: 12
<212> TYPE: PRT
<213> ORGANISM: Homo sapiens

```
<400> SEQUENCE: 106

Ile Val Ile Tyr Glu Asp Asn Gln Arg Pro Ser Gly
1               5                   10

<210> SEQ ID NO 107
<211> LENGTH: 11
<212> TYPE: PRT
<213> ORGANISM: Homo sapiens

<400> SEQUENCE: 107

Ser Lys Trp Glu Leu Val Asp Pro Tyr Gly Tyr
1               5                   10

<210> SEQ ID NO 108
<211> LENGTH: 9
<212> TYPE: PRT
<213> ORGANISM: Homo sapiens

<400> SEQUENCE: 108

Gln Ser Tyr Glu Ala Ser Asn Val Val
1               5
```